US007846908B2

(12) United States Patent
Vornlocher et al.

(10) Patent No.: US 7,846,908 B2
(45) Date of Patent: Dec. 7, 2010

(54) RNAI MODULATION OF TGF-BETA AND THERAPEUTIC USES THEREOF

(75) Inventors: Hans-Peter Vornlocher, Bayreuth (DE); Pamela Tan, Kulmbach (DE); Rainer Constien, Kulmbach (DE)

(73) Assignee: Alnylam Pharmaceuticals, Inc., Cambridge, MA (US)

( * ) Notice: Subject to any disclaimer, the term of this patent is extended or adjusted under 35 U.S.C. 154(b) by 124 days.

(21) Appl. No.: 11/724,790

(22) Filed: Mar. 15, 2007

(65) Prior Publication Data

US 2008/0015161 A1    Jan. 17, 2008

Related U.S. Application Data

(60) Provisional application No. 60/782,829, filed on Mar. 16, 2006.

(51) Int. Cl.
 *A01N 43/04* (2006.01)
 *A61K 31/70* (2006.01)
 *C07H 21/04* (2006.01)
(52) U.S. Cl. ........................................ 514/44; 536/24.5
(58) Field of Classification Search ................ 536/24.5; 514/44
See application file for complete search history.

(56) References Cited

U.S. PATENT DOCUMENTS

| | | | |
|---|---|---|---|
| 5,595,760 | A | 1/1997 | Cherif-Cheikh |
| 5,672,659 | A | 9/1997 | Shalaby et al. |
| 5,756,353 | A | 5/1998 | Debs |
| 5,858,784 | A | 1/1999 | Debs et al. |
| 5,902,880 | A | 5/1999 | Thompson |
| 6,071,497 | A | 6/2000 | Steiner et al. |
| 6,146,886 | A | 11/2000 | Thompson |
| 6,294,153 | B1 | 9/2001 | Modi |
| 6,344,194 | B1 | 2/2002 | Sene et al. |
| 6,395,713 | B1 | 5/2002 | Beigelman et al. |
| 2005/0107325 | A1 | 5/2005 | Manoharan et al. |
| 2007/0031844 | A1* | 2/2007 | Khvorova et al. ............ 435/6 |

FOREIGN PATENT DOCUMENTS

| | | |
|---|---|---|
| WO | WO 93/23569 | 11/1993 |
| WO | WO 94/02595 | 2/1994 |
| WO | WO 96/10390 | 4/1996 |
| WO | WO 96/10391 | 4/1996 |
| WO | WO 96/10392 | 4/1996 |
| WO | WO 98/10796 | 3/1998 |
| WO | WO 98/31346 | 7/1998 |
| WO | WO 00/27359 | 5/2000 |
| WO | WO 00/53722 | 9/2000 |
| WO | WO 00/66206 | 11/2000 |
| WO | WO 01/54664 | 8/2001 |
| WO | WO 01/60420 | 8/2001 |
| WO | WO 02/053190 | 7/2002 |
| WO | WO 02/060412 | 8/2002 |
| WO | WO 02/066078 | 8/2002 |
| WO | WO 2004/064737 | 8/2004 |
| WO | WO 2004/080406 | 9/2004 |
| WO | WO 2004/094345 | 11/2004 |
| WO | WO 2004/094595 | 11/2004 |
| WO | WO 2005/015481 | 2/2005 |

OTHER PUBLICATIONS

NM_000660.3 ((GenBank [online] Bethesda, MD USA: United States National Library of Medicine [retrieved on Jun. 13, 2008]. Retrieved from internet using <URL: http://www.ncbi.nlm.nih.gov/entrez/viewer.fcgi?db=nuccore&id=63025221>, GenBank, Accession No. NM_000660).*
Hammond et al. Nature, 2001, vol. 2, pp. 110-119.*
Promega, retrieved from internet using <URL: http://www.promega.com/siRNADesigner/>, retrieved on Jun. 13, 2008, available 2004 to the public [online]), including search results for GenBank NM_000660 and revision history.*
Aldrian-Herrada et al., "A Peptide Nucleic Acid (PNA) is More Rapidly Internalized in Cultured Neurons When Coupled to a *Retro-Inverso* Delivery Peptide. The Antisense Activity Depresses the Target mRNA and Protein in Magnocellular Oxytocin Neurons," *Nucleic Acids Research* 26(11): 4910-4916 (1998).
Beaucage, S. and Iyer, R., "Advances in the Syntheseis of Oligonucleotides by the Phosphoramidite Approach," *Tetrahedron*, 48(12): 2223-2311 (1992).
Boado, R., "Antisense Drug Delivery Through the Blood-Brain Barrier," *Advanced Drug Delivery Reviews* 15:73-107 (1995).
Boado et al., "Drug Delivery of Antisense Molecules to the Brain for Treatment of Alzheimer's Disease and Cerebral AIDS," *Journal of Pharmaceutical Sciences*, 87(11): 1308-1315 (1998).
Chen et al., "Multitarget-Ribozyme Directed to Cleave at Up to Nine Highly Conserved HIV-1 env RNA Regions Inhibits HIV-1 Replication—Potential Effectiveness Against Most Presently Sequenced HIV-1 Isolates," *Nucleic Acids Research* 20(17): 4581-4589 (1992).
Chowrira et al., "In Vitro and In Vivo Comparison of Hammerhead, Hairpin and Hepatitis Delta Virus Self-Processing Ribozyme Cassettes," *The Journal of Biological Chemistry* 269(41): 25858-25864 (1994).
Couture et al., "Anti-Gene Therapy: The Use of Ribozymes to Inhibit Gene Function," *TIG* 12(12): 510-515 (1996).
Dropulic et al., "Functional Characterization of a U5 Ribozyme: Intracellular Suppression of Human Immunodeficiency Virus Type 1 Expression," *Journal of Virology*, 66(3): 1432-1441 (1992).
Elbashir et al., "RNA Interference is Mediated by 21- and 22-Nucleotide RNAs," *Genes & Development*, 15:188-200 (2001).
Fire et al., "Potent and Specific Genetic Interference by Double-Stranded RNA in *Caenorhabditis elegans*," *Nature* 391: 806-811 (1998).

(Continued)

*Primary Examiner*—Brian Whiteman
(74) *Attorney, Agent, or Firm*—Fenwick & West LLP

(57) ABSTRACT

The present invention concerns methods of treatment using transforming growth factor beta (TGF-beta) modulators. More specifically, the invention concerns methods of treating disorders associated with undesirable TGF-beta signaling, by administering short interfering RNA which down-regulate the expression of TGF-beta, and agents useful therein.

32 Claims, No Drawings

OTHER PUBLICATIONS

Gonzalez et al., "New Class of Polymers for the Delivery of Macromolecular Therpeutics," *Bioconjugate Chem.* 10: 1068-1074 (1999).

Good et al., "Expression of Small, Therapeutic RNAs in Human Cell Nuclei," *Gene Therapy* 4:45-54 (1997).

Izant et al., "Constitutive and Conditional Suppression of Exogenous and Endogenous Genes by Anti-Sense RNA," *Science*, 229: 345-352 (1985).

Jolliet-Riant et al., "Drug Transfer Across the Blood-Brain Barrier and Improvement of Brain Delivery," *Fundam. Clin. Pharmacol.* 13: 16-26 (1999).

Kashani-Sabet et al., "Reversal of the Malignant Phenotype by an Anti-*ras* Ribozyme," *Antisense Research and Development*, 2: 3-15 (1992).

Lasic et al., "Liposomes Revisited," *Science*, 267: 1275-1276 (1995).

Lasic et al., "The 'Stealth' Liposome: A Prototypical Biomaterial," *Chemical Reviews* 95(8):2601-2628 (1995).

Liu et al., "Cationic Liposome-Mediated Intravenous Gene Delivery," *The Journal of Biomedical Chemistry*, 270(42): 24864-24870 (1995).

McGarry et al., "Inhibition of Heat Shock Protein Synthesis by Heat-Inducible Antisense RNA," *Proc. Natl. Acad. Sci. USA* 83:399-403 (1986).

Nykanen et al., "ATP Requirements and Small Interfering RNA Structure in the RNA Interference Pathway," *Cell* 107: 309-321 (2001).

Ohkawa et al., "Activities of HIV-RNA Targeted Ribozymes Transcribed from a 'Shot-Gun' Type Ribozyme-Trimming Plasmid," ., *Nucleic Acids Symp. Ser.* 27:15-16, (1992).

Ojwang et al., "Inhibition of Human Immunodeficiency Virus Type 1 Expression by a Hairpin Ribozyme," *Proc. Natl. Acad. Sci. USA* 89: 10802-10806 (1992).

Oku et al., "Real-Time Analysis of Liposomal Trafficking in Tumor-Bearing Mice by Use of Positron Emission Tomography," *Biochimica et Biophysica Acta*, 1238:86-90 (1995).

Pardridge et al., "Vecotr-Mediated Delivery of a Polyamide ("Peptide") Nucleic Acid Analogue Through the Blood-Brain Barrier in vivo," *PNAS* 92: 5592-5596 (1995).

Sandrasagra et al., "Discovery and Development of Respirable Antisense Therapeutics for Asthma," *Antisense & Nucleic Acid Drug Development* 12: 177-181 (2002).

Sandrasagra et al., "RASONs: A Novel Antisense Oligonucleotide Therapeutic Approach for Asthma," *Expert Opin. Biol. Ther.* 1(6): 979-983 (2001).

Sarver et al., "Ribozymes as Potential Ant-HIV-1 Therapeutic Agents," *Science*, 247: 1222-1225 (1990).

Scanlon et al., "Ribozyme-Mediated Cleavage of C-FOS mRNA Reduces Gene Expression of DNA Synthesis Enzymes and Metallothionein," *Proc. Natl. Acad. Sci. USA* 88:10591-10595 (1991).

Taira et al., "Construction of a Novel RNA-Transcript-Trimming Plasmid Which Can be Used Both in vitro in Place of Run-Off and (G)-Free Transcriptions and in vivo as Multi-Sequences Transcription Vectors," *Nucleic Acids Research* 19: 5125-5130 (1991).

Templin et al., "Pharmacokinetic and Toxicity Profile of a Phosphorothioate Oligonucleotide Following Inhalation Delivery to Lung in Mice," *Antisense & Nucleic Acid Drug Development*, 10:359-368 (2000).

Thompson et al., "Improved Accumulation and Activity of Ribozymes Expressed from tRNA-Based RNA Polymerase III Promoter," *Nucleic Acids Research*, 23(12): 2259-2268 (1995).

Tyler et al., "Peptide Nucleic Acids Targeted to the Neurotensin Receptor and Administered I.P. Cross the Blood-Brain Barrier and Specifically Reduce Gene Expression," *PNAS* 96: 7053-7058 (1999).

Tyler et al., "Specific Gene Blockade Shows that Peptide Nucleic Acids Readily Enter Neuronal Cells in vivo," *FEBS Letters* 421: 280-284 (1998).

Ventura et al., "Activation of HIV-Specific Ribozyme Activity by Self-Cleavage," *Nucleic Acids Research* 21(14): 3249-3255 (1993).

Weerasinghe et al., "Resistance to Human Immunodeficiency Virus Type 1 (HIV-1) Infection in Human CD4+ Lymphocyte-Derived Cell Lines Conferred by Using Retroviral Vectors Expressing an HIV-1 RNA-Specific Ribozyme," *Journal of Virology* 65(10): 5531-5534 (1991).

Boese et al., Mechanistic Insights Aid Computational Short Interfering RNA Design, Methods in Enzymology, vol. 392 (2005), pp. 73-96.

Elbashir et al., Functional Anatomy of siRNAs for Mediating Efficient RNAi in Drosophila melanogaster Embryo Lysate, EMBO Journal, vol. 20, No. 23 (2001), pp. 6877-6888.

Ishiwata et al., Physical-Chemistry Characteristics and Biodistribution of Poly(ethylene glycol)-Coated Liposomes Using Poly(oxyethylene) Cholesteryl Ether, Chemical & Pharmaceutical Bulletin, vol. 43, No. 6 (1995) pp. 1005-1011.

Reynolds et al., Rational siRNA Design for RNA Interference, Nature Biotechnology, vol. 22, No. 3 (2004) pp. 326-330.

NM_011577 ((GenBenk [online] Bethesda, MD USA: United States National Library of Medicine [retrieved on Aug. 7, 2007]. Retrieved from internet using <URL: http://www.ncbi.nlm.nih.gov/entrez/viewer.fcgi?6755774:OLD13:239029>, GenBank Accession No. NM_011577).

NM_002046 ((GenBenk [online] Bethesda, MD USA: United States National Library of Medicine [retrieved on Aug. 7, 2007]. Retrieved from internet using <URL: http://www.ncbi.nlm.nih.gov/entrez/viewer.fcgi?83641890: NCBI:16506826>, GenBank Accession No. NM_002046).

NM_000660 ((GenBenk [online] Bethesda, MD USA: United States National Library of Medicine [retrieved on Aug. 7, 2007]. Retrieved from internet using <URL: http://www.ncbi.nlm.nih.gov/entrez/viewer.fcgi?63025221: NCBI:10049703>, GenBank Accession No. NM_000660).

PCT International Search Report and Written Opinion, PCT/US2007/006554, Oct. 7, 2008, 10 Pages.

* cited by examiner

SEQUENCE LISTING

<160> NUMBER OF SEQ ID NOS: 577

<210> SEQ ID NO 1
<211> LENGTH: 21
<212> TYPE: DNA
<213> ORGANISM: Artificial sequence
<220> FEATURE:
<223> OTHER INFORMATION: Oligonucleotide sequences of siRNAs specific
      for TGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 1
ggucacccgc gugcuaaugt t                                               21

<210> SEQ ID NO 2
<211> LENGTH: 21
<212> TYPE: DNA
<213> ORGANISM: Artificial sequence
<220> FEATURE:
<223> OTHER INFORMATION: Oligonucleotide sequences of siRNAs specific
      for TGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

```
<400> SEQUENCE: 2
cauuagcacg cgggugacct t                                              21

<210> SEQ ID NO 3
<211> LENGTH: 21
<212> TYPE: DNA
<213> ORGANISM: Artificial sequence
<220> FEATURE:
<223> OTHER INFORMATION: Oligonucleotide sequences of siRNAs specific
      for TGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 3, 4, 6, 7, 8, 10, 12, 14, 15, 18
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1, 2, 5, 9, 11, 13, 16, 17, 19
<223> OTHER INFORMATION: /mod_base = "2'-hydroxy corresponding base"

<400> SEQUENCE: 3
ggucacccgc gugcuaaugt t                                              21

<210> SEQ ID NO 4
<211> LENGTH: 21
<212> TYPE: DNA
<213> ORGANISM: Artificial sequence
<220> FEATURE:
<223> OTHER INFORMATION: Oligonucleotide sequences of siRNAs specific
      for TGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1, 4, 7
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 2, 3, 5, 6, 8, 9, 10, 11, 12, 13, 14, 15, 16, 17, 18, 19
<223> OTHER INFORMATION: /mod_base = "2'-hydroxy corresponding base"

<400> SEQUENCE: 4
cauuagcacg cgggugacct t                                              21

<210> SEQ ID NO 5
<211> LENGTH: 21
<212> TYPE: DNA
<213> ORGANISM: Artificial sequence
<220> FEATURE:
<223> OTHER INFORMATION: Oligonucleotide sequences of siRNAs specific
      for TGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 5
gaggucaccc gcgugcuaat t                                              21
```

<210> SEQ ID NO 6
<211> LENGTH: 21
<212> TYPE: DNA
<213> ORGANISM: Artificial sequence
<220> FEATURE:
<223> OTHER INFORMATION: Oligonucleotide sequences of siRNAs specific
      for TGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 6
uuagcacgcg ggugaccuct t                                              21

<210> SEQ ID NO 7
<211> LENGTH: 21
<212> TYPE: DNA
<213> ORGANISM: Artificial sequence
<220> FEATURE:
<223> OTHER INFORMATION: Oligonucleotide sequences of siRNAs specific
      for TGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 5, 6, 8, 9, 10, 12, 14, 16, 17
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1, 2, 3, 4, 7, 11, 13, 15, 18, 19
<223> OTHER INFORMATION: /mod_base = "2'-hydroxy corresponding base"

<400> SEQUENCE: 7
gaggucaccc gcgugcuaat t                                              21

<210> SEQ ID NO 8
<211> LENGTH: 21
<212> TYPE: DNA
<213> ORGANISM: Artificial sequence
<220> FEATURE:
<223> OTHER INFORMATION: Oligonucleotide sequences of siRNAs specific
      for TGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 2, 5
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1, 3, 4, 6, 7, 8, 9, 10, 11, 12, 13, 14, 15, 16, 17, 18,
      19
<223> OTHER INFORMATION: /mod_base = "2'-hydroxy corresponding base"

<400> SEQUENCE: 8
uuagcacgcg ggugaccuct t                                              21

```
<210> SEQ ID NO 9
<211> LENGTH: 21
<212> TYPE: DNA
<213> ORGANISM: Artificial sequence
<220> FEATURE:
<223> OTHER INFORMATION: Oligonucleotide sequences of siRNAs specific
      for TGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 9
agcacccgcg accgggtggt t                                              21

<210> SEQ ID NO 10
<211> LENGTH: 21
<212> TYPE: DNA
<213> ORGANISM: Artificial sequence
<220> FEATURE:
<223> OTHER INFORMATION: Oligonucleotide sequences of siRNAs specific
      for TGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 10
ccacccgguc gcgggugcut t                                              21

<210> SEQ ID NO 11
<211> LENGTH: 21
<212> TYPE: DNA
<213> ORGANISM: Artificial sequence
<220> FEATURE:
<223> OTHER INFORMATION: Oligonucleotide sequences of siRNAs specific
      for TGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 3, 5, 6, 7, 9, 12, 13, 17
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1, 2, 4, 8, 10, 11, 14, 15, 16, 18, 19
<223> OTHER INFORMATION: /mod_base = "2'-hydroxy corresponding base"

<400> SEQUENCE: 11
agcacccgcg accgggguggt t                                             21

<210> SEQ ID NO 12
<211> LENGTH: 21
<212> TYPE: DNA
<213> ORGANISM: Artificial sequence
<220> FEATURE:
<223> OTHER INFORMATION: Oligonucleotide sequences of siRNAs specific
      for TGF-beta
<220> FEATURE:
<223> OTHER INFORMATION: 5'-terminal nucleic acid is a nucleoside, i.e.
      base + sugar but lacking 5'-phosphate
<220> FEATURE:
```

```
<221> NAME/KEY: modified_base
<222> LOCATION: 2
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1, 3, 4, 5, 6, 7, 8, 9, 10, 11, 12, 13, 14, 15, 16, 17,
      18, 19
<223> OTHER INFORMATION: /mod_base = "2'-hydroxy corresponding base"

<400> SEQUENCE: 12
ccacccgguc gcgggugcut t                                               21

<210> SEQ ID NO 13
<211> LENGTH: 21
<212> TYPE: DNA
<213> ORGANISM: Artificial sequence
<220> FEATURE:
<223> OTHER INFORMATION: Oligonucleotide sequences of siRNAs specific
      for TGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 13
uccacgagcc caagggcuat t                                               21

<210> SEQ ID NO 14
<211> LENGTH: 21
<212> TYPE: DNA
<213> ORGANISM: Artificial sequence
<220> FEATURE:
<223> OTHER INFORMATION: Oligonucleotide sequences of siRNAs specific
      for TGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 14
uagcccuugg gcucguggat t                                               21

<210> SEQ ID NO 15
<211> LENGTH: 21
<212> TYPE: DNA
<213> ORGANISM: Artificial sequence
<220> FEATURE:
<223> OTHER INFORMATION: Oligonucleotide sequences of siRNAs specific
      for TGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1, 2, 3, 5, 9, 10, 11, 17, 18
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 4, 6, 7, 8, 12, 13, 14, 15, 16, 19
```

<223> OTHER INFORMATION: /mod_base = "2'-hydroxy corresponding base"

<400> SEQUENCE: 15
uccacgagcc caagggcuat t                                              21

<210> SEQ ID NO 16
<211> LENGTH: 21
<212> TYPE: DNA
<213> ORGANISM: Artificial sequence
<220> FEATURE:
<223> OTHER INFORMATION: Oligonucleotide sequences of siRNAs specific
      for TGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 2..19
<223> OTHER INFORMATION: /mod_base = "2'-hydroxy corresponding base"

<400> SEQUENCE: 16
uagcccuugg gcucguggat t                                              21

<210> SEQ ID NO 17
<211> LENGTH: 21
<212> TYPE: DNA
<213> ORGANISM: Artificial sequence
<220> FEATURE:
<223> OTHER INFORMATION: Oligonucleotide sequences of siRNAs specific
      for TGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 17
auuccggacc agcccucggt t                                              21

<210> SEQ ID NO 18
<211> LENGTH: 21
<212> TYPE: DNA
<213> ORGANISM: Artificial sequence
<220> FEATURE:
<223> OTHER INFORMATION: Oligonucleotide sequences of siRNAs specific
      for TGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 18
ccgagggcug guccggaaut t                                              21

<210> SEQ ID NO 19
<211> LENGTH: 21
<212> TYPE: DNA
<213> ORGANISM: Artificial sequence
<220> FEATURE:
<223> OTHER INFORMATION: Oligonucleotide sequences of siRNAs specific
      for TGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 2, 3, 4, 5, 9, 10, 13, 14, 15, 16, 17
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1, 6, 7, 8, 11, 12, 18, 19
<223> OTHER INFORMATION: /mod_base = "2'-hydroxy corresponding base"

<400> SEQUENCE: 19
auuccggacc agcccucggt t                                           21

<210> SEQ ID NO 20
<211> LENGTH: 21
<212> TYPE: DNA
<213> ORGANISM: Artificial sequence
<220> FEATURE:
<223> OTHER INFORMATION: Oligonucleotide sequences of siRNAs specific
      for TGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1..19
<223> OTHER INFORMATION: /mod_base = "2'-hydroxy corresponding base"

<400> SEQUENCE: 20
ccgagggcug guccggaaut t                                           21

<210> SEQ ID NO 21
<211> LENGTH: 21
<212> TYPE: DNA
<213> ORGANISM: Artificial sequence
<220> FEATURE:
<223> OTHER INFORMATION: Oligonucleotide sequences of siRNAs specific
      for TGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 21
aggucacccg cgugcuaaut t                                           21

<210> SEQ ID NO 22
<211> LENGTH: 21
<212> TYPE: DNA
<213> ORGANISM: Artificial sequence
<220> FEATURE:
<223> OTHER INFORMATION: Oligonucleotide sequences of siRNAs specific
      for TGF-beta
<220> FEATURE:
<223> OTHER INFORMATION: 5'-terminal nucleic acid is a nucleoside, i.e.
      base + sugar but lacking 5'-phosphate
<220> FEATURE:

<221> NAME/KEY: modified_base
<222> LOCATION: 1..19
<223> OTHER INFORMATION: /mod_base = "2'-hydroxy corresponding base"

<400> SEQUENCE: 22
auuagcacgc gggugaccut t                                              21

<210> SEQ ID NO 23
<211> LENGTH: 21
<212> TYPE: DNA
<213> ORGANISM: Artificial sequence
<220> FEATURE:
<223> OTHER INFORMATION: Oligonucleotide sequences of siRNAs specific
      for TGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 4, 5, 7, 8, 9, 11, 13, 15, 16, 19
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1, 2, 3, 6, 10, 12, 14, 17, 18
<223> OTHER INFORMATION: /mod_base = "2'-hydroxy corresponding base"

<400> SEQUENCE: 23
aggucacccg cgugcuaaut t                                              21

<210> SEQ ID NO 24
<211> LENGTH: 21
<212> TYPE: DNA
<213> ORGANISM: Artificial sequence
<220> FEATURE:
<223> OTHER INFORMATION: Oligonucleotide sequences of siRNAs specific
      for TGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 3, 6
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1, 2, 4, 5, 7, 8, 9, 10, 11, 12, 13, 14, 15, 16, 17, 18,
      19
<223> OTHER INFORMATION: /mod_base = "2'-hydroxy corresponding base"

<400> SEQUENCE: 24
auuagcacgc gggugaccut t                                              21

<210> SEQ ID NO 25
<211> LENGTH: 21
<212> TYPE: DNA
<213> ORGANISM: Artificial sequence
<220> FEATURE:
<223> OTHER INFORMATION: Oligonucleotide sequences of siRNAs specific
      for TGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19

```
<223> OTHER INFORMATION: /mod_base = "2'-hydroxy corresponding base"

<400> SEQUENCE: 25
uuccggacca gcccucgggt t                                              21

<210> SEQ ID NO 26
<211> LENGTH: 21
<212> TYPE: DNA
<213> ORGANISM: Artificial sequence
<220> FEATURE:
<223> OTHER INFORMATION: Oligonucleotide sequences of siRNAs specific
      for TGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 26
cccgagggcu gguccggaat t                                              21

<210> SEQ ID NO 27
<211> LENGTH: 21
<212> TYPE: DNA
<213> ORGANISM: Artificial sequence
<220> FEATURE:
<223> OTHER INFORMATION: Oligonucleotide sequences of siRNAs specific
      for TGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1, 2, 3, 4, 8, 9, 12, 13, 14, 15, 16
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 5, 6, 7, 10, 11, 17, 18, 19
<223> OTHER INFORMATION: /mod_base = "2'-hydroxy corresponding base"

<400> SEQUENCE: 27
uuccggacca gcccucgggt t                                              21

<210> SEQ ID NO 28
<211> LENGTH: 21
<212> TYPE: DNA
<213> ORGANISM: Artificial sequence
<220> FEATURE:
<223> OTHER INFORMATION: Oligonucleotide sequences of siRNAs specific
      for TGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1..19
<223> OTHER INFORMATION: /mod_base = "2'-hydroxy corresponding base"

<400> SEQUENCE: 28
cccgagggcu gguccggaat t                                              21
```

<210> SEQ ID NO 29
<211> LENGTH: 21
<212> TYPE: DNA
<213> ORGANISM: Artificial sequence
<220> FEATURE:
<223> OTHER INFORMATION: Oligonucleotide sequences of siRNAs specific
      for TGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 29
uguacaacag cacccgcgat t                                              21

<210> SEQ ID NO 30
<211> LENGTH: 21
<212> TYPE: DNA
<213> ORGANISM: Artificial sequence
<220> FEATURE:
<223> OTHER INFORMATION: Oligonucleotide sequences of siRNAs specific
      for TGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 30
ucgcgggugc uguuguacat t                                              21

<210> SEQ ID NO 31
<211> LENGTH: 21
<212> TYPE: DNA
<213> ORGANISM: Artificial sequence
<220> FEATURE:
<223> OTHER INFORMATION: Oligonucleotide sequences of siRNAs specific
      for TGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1, 3, 5, 8, 11, 13, 14, 15, 17
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 2, 4, 6, 7, 9, 10, 12, 16, 18, 19
<223> OTHER INFORMATION: /mod_base = "2'-hydroxy corresponding base"

<400> SEQUENCE: 31
uguacaacag cacccgcgat t                                              21

<210> SEQ ID NO 32
<211> LENGTH: 21
<212> TYPE: DNA
<213> ORGANISM: Artificial sequence
<220> FEATURE:
<223> OTHER INFORMATION: Oligonucleotide sequences of siRNAs specific
      for TGF-beta
<220> FEATURE:
<223> OTHER INFORMATION: 5'-terminal nucleic acid is a nucleoside, i.e.
      base + sugar but lacking 5'-phosphate
<220> FEATURE:

```
<221> NAME/KEY: modified_base
<222> LOCATION: 16, 18
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1, 2, 3, 4, 5, 6, 7, 8, 9, 10, 11, 12, 13, 14, 15, 17,
      19
<223> OTHER INFORMATION: /mod_base = "2'-hydroxy corresponding base"

<400> SEQUENCE: 32
ucgcgggugc uguuguacat t                                              21

<210> SEQ ID NO 33
<211> LENGTH: 21
<212> TYPE: DNA
<213> ORGANISM: Artificial sequence
<220> FEATURE:
<223> OTHER INFORMATION: Oligonucleotide sequences of siRNAs specific
      for TGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 33
cacccgcgug cuaauggugt t                                              21

<210> SEQ ID NO 34
<211> LENGTH: 21
<212> TYPE: DNA
<213> ORGANISM: Artificial sequence
<220> FEATURE:
<223> OTHER INFORMATION: Oligonucleotide sequences of siRNAs specific
      for TGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 34
caccauuagc acgcgggugt t                                              21

<210> SEQ ID NO 35
<211> LENGTH: 21
<212> TYPE: DNA
<213> ORGANISM: Artificial sequence
<220> FEATURE:
<223> OTHER INFORMATION: Oligonucleotide sequences of siRNAs specific
      for TGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1, 3, 4, 5, 7, 9, 11, 12, 15, 18
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 2, 6, 8, 10, 13, 14, 16, 17, 19
```

<223> OTHER INFORMATION: /mod_base = "2'-hydroxy corresponding base"

<400> SEQUENCE: 35
cacccgcgug cuaauggugt t               21

<210> SEQ ID NO 36
<211> LENGTH: 21
<212> TYPE: DNA
<213> ORGANISM: Artificial sequence
<220> FEATURE:
<223> OTHER INFORMATION: Oligonucleotide sequences of siRNAs specific
      for TGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1, 4, 7, 10
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 2, 3, 5, 6, 8, 9, 11, 12, 13, 14, 15, 16, 17, 18, 19
<223> OTHER INFORMATION: /mod_base = "2'-hydroxy corresponding base"

<400> SEQUENCE: 36
caccauuagc acgcgggugt t               21

<210> SEQ ID NO 37
<211> LENGTH: 21
<212> TYPE: DNA
<213> ORGANISM: Artificial sequence
<220> FEATURE:
<223> OTHER INFORMATION: Oligonucleotide sequences of siRNAs specific
      for TGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 37
uccggaccag cccucgggat t               21

<210> SEQ ID NO 38
<211> LENGTH: 21
<212> TYPE: DNA
<213> ORGANISM: Artificial sequence
<220> FEATURE:
<223> OTHER INFORMATION: Oligonucleotide sequences of siRNAs specific
      for TGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 38
ucccgagggc ugguccggat t               21

<210> SEQ ID NO 39
<211> LENGTH: 21
<212> TYPE: DNA
<213> ORGANISM: Artificial sequence
<220> FEATURE:
<223> OTHER INFORMATION: Oligonucleotide sequences of siRNAs specific
     for TGF-beta
<220> FEATURE:
<223> OTHER INFORMATION: 5'-terminal nucleic acid is a nucleoside, i.e.
     base + sugar but lacking 5'-phosphate
<220> FEATURE:
<221> NAME/KEY: modified_base
<222> LOCATION: 1, 2, 3, 7, 8, 11, 12, 13, 14, 15
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 4, 5, 6, 9, 10, 16, 17, 18, 19
<223> OTHER INFORMATION: /mod_base = "2'-hydroxy corresponding base"

<400> SEQUENCE: 39
uccggaccag cccucgggat t                                          21

<210> SEQ ID NO 40
<211> LENGTH: 21
<212> TYPE: DNA
<213> ORGANISM: Artificial sequence
<220> FEATURE:
<223> OTHER INFORMATION: Oligonucleotide sequences of siRNAs specific
     for TGF-beta
<220> FEATURE:
<223> OTHER INFORMATION: 5'-terminal nucleic acid is a nucleoside, i.e.
     base + sugar but lacking 5'-phosphate
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1..19
<223> OTHER INFORMATION: /mod_base = "2'-hydroxy corresponding base"

<400> SEQUENCE: 40
ucccgagggc ugguccggat t                                          21

<210> SEQ ID NO 41
<211> LENGTH: 21
<212> TYPE: DNA
<213> ORGANISM: Artificial sequence
<220> FEATURE:
<223> OTHER INFORMATION: Oligonucleotide sequences of siRNAs specific
     for TGF-beta
<220> FEATURE:
<223> OTHER INFORMATION: 5'-terminal nucleic acid is a nucleoside, i.e.
     base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 41
uggaagugga uccacgagct t                                          21

<210> SEQ ID NO 42
<211> LENGTH: 21
<212> TYPE: DNA
<213> ORGANISM: Artificial sequence
<220> FEATURE:
<223> OTHER INFORMATION: Oligonucleotide sequences of siRNAs specific
     for TGF-beta
<220> FEATURE:
<223> OTHER INFORMATION: 5'-terminal nucleic acid is a nucleoside, i.e.
     base + sugar but lacking 5'-phosphate
<220> FEATURE:

```
<221> NAME/KEY: modified_base
<222> LOCATION: 1..19
<223> OTHER INFORMATION: /mod_base = "2'-hydroxy corresponding base"

<400> SEQUENCE: 42
gcucguggau ccacuuccat t                                              21

<210> SEQ ID NO 43
<211> LENGTH: 21
<212> TYPE: DNA
<213> ORGANISM: Artificial sequence
<220> FEATURE:
<223> OTHER INFORMATION: Oligonucleotide sequences of siRNAs specific
      for TGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1, 7, 11, 12, 13, 15, 19
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 2, 3, 4, 5, 6, 8, 9, 10, 14, 16, 17, 18
<223> OTHER INFORMATION: /mod_base = "2'-hydroxy corresponding base"

<400> SEQUENCE: 43
uggaagugga uccacgagct t                                              21

<210> SEQ ID NO 44
<211> LENGTH: 21
<212> TYPE: DNA
<213> ORGANISM: Artificial sequence
<220> FEATURE:
<223> OTHER INFORMATION: Oligonucleotide sequences of siRNAs specific
      for TGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 12, 18
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1, 2, 3, 4, 5, 6, 7, 8, 9, 10, 11, 13, 14, 15, 16, 17,
      19
<223> OTHER INFORMATION: /mod_base = "2'-hydroxy corresponding base"

<400> SEQUENCE: 44
gcucguggau ccacuuccat t                                              21

<210> SEQ ID NO 45
<211> LENGTH: 21
<212> TYPE: DNA
<213> ORGANISM: Artificial sequence
<220> FEATURE:
<223> OTHER INFORMATION: Oligonucleotide sequences of siRNAs specific
      for TGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
```

```
<223> OTHER INFORMATION: /mod_base = "2'-hydroxy corresponding base"

<400> SEQUENCE: 45
ccaagggcua ccaugccaat t                                              21

<210> SEQ ID NO 46
<211> LENGTH: 21
<212> TYPE: DNA
<213> ORGANISM: Artificial sequence
<220> FEATURE:
<223> OTHER INFORMATION: Oligonucleotide sequences of siRNAs specific
      for TGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 46
uuggcauggu agcccuuggt t                                              21

<210> SEQ ID NO 47
<211> LENGTH: 21
<212> TYPE: DNA
<213> ORGANISM: Artificial sequence
<220> FEATURE:
<223> OTHER INFORMATION: Oligonucleotide sequences of siRNAs specific
      for TGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1, 2, 8, 9, 11, 12, 14, 16, 17
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 3, 4, 5, 6, 7, 10, 13, 15, 18, 19
<223> OTHER INFORMATION: /mod_base = "2'-hydroxy corresponding base"

<400> SEQUENCE: 47
ccaagggcua ccaugccaat t                                              21

<210> SEQ ID NO 48
<211> LENGTH: 21
<212> TYPE: DNA
<213> ORGANISM: Artificial sequence
<220> FEATURE:
<223> OTHER INFORMATION: Oligonucleotide sequences of siRNAs specific
      for TGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 5, 10
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1, 2, 3, 4, 6, 7, 8, 9, 11, 12, 13, 14, 15, 16, 17, 18,
      19
<223> OTHER INFORMATION: /mod_base = "2'-hydroxy corresponding base"
```

```
<400> SEQUENCE: 48
uuggcauggu agcccuuggt t                                              21

<210> SEQ ID NO 49
<211> LENGTH: 21
<212> TYPE: DNA
<213> ORGANISM: Artificial sequence
<220> FEATURE:
<223> OTHER INFORMATION: Oligonucleotide sequences of siRNAs specific
      for TGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 49
gucacccgcg ugcuaauggt t                                              21

<210> SEQ ID NO 50
<211> LENGTH: 21
<212> TYPE: DNA
<213> ORGANISM: Artificial sequence
<220> FEATURE:
<223> OTHER INFORMATION: Oligonucleotide sequences of siRNAs specific
      for TGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 50
ccauuagcac gcgggugact t                                              21

<210> SEQ ID NO 51
<211> LENGTH: 21
<212> TYPE: DNA
<213> ORGANISM: Artificial sequence
<220> FEATURE:
<223> OTHER INFORMATION: Oligonucleotide sequences of siRNAs specific
      for TGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 2, 3, 5, 6, 7, 9, 11, 13, 14, 17
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1, 4, 8, 10, 12, 15, 16, 18, 19
<223> OTHER INFORMATION: /mod_base = "2'-hydroxy corresponding base"

<400> SEQUENCE: 51
gucacccgcg ugcuaauggt t                                              21

<210> SEQ ID NO 52
<211> LENGTH: 21
<212> TYPE: DNA
<213> ORGANISM: Artificial sequence
<220> FEATURE:
<223> OTHER INFORMATION: Oligonucleotide sequences of siRNAs specific
```

```
    for TGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 2, 5, 8
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1, 3, 4, 6, 7, 9, 10, 11, 12, 13, 14, 15, 16, 17, 18, 19
<223> OTHER INFORMATION: /mod_base = "2'-hydroxy corresponding base"

<400> SEQUENCE: 52
ccauuagcac gcgggugact t                                              21

<210> SEQ ID NO 53
<211> LENGTH: 21
<212> TYPE: DNA
<213> ORGANISM: Artificial sequence
<220> FEATURE:
<223> OTHER INFORMATION: Oligonucleotide sequences of siRNAs specific
      for TGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 53
uacaacagca cccgcgacct t                                              21

<210> SEQ ID NO 54
<211> LENGTH: 21
<212> TYPE: DNA
<213> ORGANISM: Artificial sequence
<220> FEATURE:
<223> OTHER INFORMATION: Oligonucleotide sequences of siRNAs specific
      for TGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 54
ggucgcgggu gcuguuguat t                                              21

<210> SEQ ID NO 55
<211> LENGTH: 21
<212> TYPE: DNA
<213> ORGANISM: Artificial sequence
<220> FEATURE:
<223> OTHER INFORMATION: Oligonucleotide sequences of siRNAs specific
      for TGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1, 3, 6, 9, 11, 12, 13, 15, 18, 19
<223> OTHER INFORMATION: /mod_base = "2'-O-methyl corresponding base"
<220> FEATURE:
<221> NAME/KEY: modified_base
<222> LOCATION: 21
```

<223> OTHER INFORMATION: /mod_base = "5'-thio thymidine"
<220> FEATURE:
<221> NAME/KEY: modified_base
<222> LOCATION: 2, 4, 5, 7, 8, 10, 14, 16, 17
<223> OTHER INFORMATION: /mod_base = "2'-hydroxy corresponding base"

<400> SEQUENCE: 55
uacaacagca cccgcgacct t                                              21

<210> SEQ ID NO 56
<211> LENGTH: 21
<212> TYPE: DNA
<213> ORGANISM: Artificial sequence
<220> FEATURE:
<223> OTHER INFORMATION: Oligonucleotide sequences of siRNAs specific
      for TGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 18
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1, 2, 3, 4, 5, 6, 7, 8, 9, 10, 11, 12, 13, 14, 15, 16,
      17, 19
<223> OTHER INFORMATION: /mod_base = "2'-hydroxy corresponding base"

<400> SEQUENCE: 56
ggucgcgggu gcuguuguat t                                              21

<210> SEQ ID NO 57
<211> LENGTH: 21
<212> TYPE: DNA
<213> ORGANISM: Artificial sequence
<220> FEATURE:
<223> OTHER INFORMATION: Oligonucleotide sequences of siRNAs specific
      for TGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 57
gcccaagggc uaccaugcct t                                              21

<210> SEQ ID NO 58
<211> LENGTH: 21
<212> TYPE: DNA
<213> ORGANISM: Artificial sequence
<220> FEATURE:
<223> OTHER INFORMATION: Oligonucleotide sequences of siRNAs specific
      for TGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 58
ggcaugguag cccuugggct t                                              21

```
<210> SEQ ID NO 59
<211> LENGTH: 21
<212> TYPE: DNA
<213> ORGANISM: Artificial sequence
<220> FEATURE:
<223> OTHER INFORMATION: Oligonucleotide sequences of siRNAs specific
      for TGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 2, 3, 4, 10, 11, 13, 14, 16, 18, 19
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1, 5, 6, 7, 8, 9, 12, 15, 17
<223> OTHER INFORMATION: /mod_base = "2'-hydroxy corresponding base"

<400> SEQUENCE: 59
gcccaagggc uaccaugcct t                                              21

<210> SEQ ID NO 60
<211> LENGTH: 21
<212> TYPE: DNA
<213> ORGANISM: Artificial sequence
<220> FEATURE:
<223> OTHER INFORMATION: Oligonucleotide sequences of siRNAs specific
      for TGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 3, 8
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1, 2, 4, 5, 6, 7, 9, 10, 11, 12, 13, 14, 15, 16, 17, 18,
      19
<223> OTHER INFORMATION: /mod_base = "2'-hydroxy corresponding base"

<400> SEQUENCE: 60
ggcaugguag cccuugggct t                                              21

<210> SEQ ID NO 61
<211> LENGTH: 21
<212> TYPE: DNA
<213> ORGANISM: Artificial sequence
<220> FEATURE:
<223> OTHER INFORMATION: Oligonucleotide sequences of siRNAs specific
      for TGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 61
aaguggaucc acgagcccat t                                              21

<210> SEQ ID NO 62
```

-continued

```
<211> LENGTH: 21
<212> TYPE: DNA
<213> ORGANISM: Artificial sequence
<220> FEATURE:
<223> OTHER INFORMATION: Oligonucleotide sequences of siRNAs specific
      for TGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 62
ugggcucgug gauccacuut t                                              21

<210> SEQ ID NO 63
<211> LENGTH: 21
<212> TYPE: DNA
<213> ORGANISM: Artificial sequence
<220> FEATURE:
<223> OTHER INFORMATION: Oligonucleotide sequences of siRNAs specific
      for TGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 4, 8, 9, 10, 12, 16, 17, 18
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1, 2, 3, 5, 6, 7, 11, 13, 14, 15, 19
<223> OTHER INFORMATION: /mod_base = "2'-hydroxy corresponding base"

<400> SEQUENCE: 63
aaguggaucc acgagcccat t                                              21

<210> SEQ ID NO 64
<211> LENGTH: 21
<212> TYPE: DNA
<213> ORGANISM: Artificial sequence
<220> FEATURE:
<223> OTHER INFORMATION: Oligonucleotide sequences of siRNAs specific
      for TGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 15
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1, 2, 3, 4, 5, 6, 7, 8, 9, 10, 11, 12, 13, 14, 16, 17,
      18, 19
<223> OTHER INFORMATION: /mod_base = "2'-hydroxy corresponding base"

<400> SEQUENCE: 64
ugggcucgug gauccacuut t                                              21

<210> SEQ ID NO 65
<211> LENGTH: 21
<212> TYPE: DNA
```

```
<213> ORGANISM: Artificial sequence
<220> FEATURE:
<223> OTHER INFORMATION: Oligonucleotide sequences of siRNAs specific
      for TGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 65
gggaggaggg acgagcuggt t                                              21

<210> SEQ ID NO 66
<211> LENGTH: 21
<212> TYPE: DNA
<213> ORGANISM: Artificial sequence
<220> FEATURE:
<223> OTHER INFORMATION: Oligonucleotide sequences of siRNAs specific
      for TGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 66
ccagcucguc ccuccuccct t                                              21

<210> SEQ ID NO 67
<211> LENGTH: 21
<212> TYPE: DNA
<213> ORGANISM: Artificial sequence
<220> FEATURE:
<223> OTHER INFORMATION: Oligonucleotide sequences of siRNAs specific
      for TGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 12, 16, 17
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1, 2, 3, 4, 5, 6, 7, 8, 9, 10, 11, 13, 14, 15, 18, 19
<223> OTHER INFORMATION: /mod_base = "2'-hydroxy corresponding base"

<400> SEQUENCE: 67
gggaggaggg acgagcuggt t                                              21

<210> SEQ ID NO 68
<211> LENGTH: 21
<212> TYPE: DNA
<213> ORGANISM: Artificial sequence
<220> FEATURE:
<223> OTHER INFORMATION: Oligonucleotide sequences of siRNAs specific
      for TGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 2
<223> OTHER INFORMATION: /mod_base = "2'-O-methyl corresponding base"
```

```
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1, 3, 4, 5, 6, 7, 8, 9, 10, 11, 12, 13, 14, 15, 16, 17,
      18, 19
<223> OTHER INFORMATION: /mod_base = "2'-hydroxy corresponding base"

<400> SEQUENCE: 68
ccagcucguc ccuccuccct t                                              21

<210> SEQ ID NO 69
<211> LENGTH: 21
<212> TYPE: DNA
<213> ORGANISM: Artificial sequence
<220> FEATURE:
<223> OTHER INFORMATION: Oligonucleotide sequences of siRNAs specific
      for TGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 69
acaacagcac ccgcgaccgt t                                              21

<210> SEQ ID NO 70
<211> LENGTH: 21
<212> TYPE: DNA
<213> ORGANISM: Artificial sequence
<220> FEATURE:
<223> OTHER INFORMATION: Oligonucleotide sequences of siRNAs specific
      for TGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 70
cggucgcggg ugcuguugut t                                              21

<210> SEQ ID NO 71
<211> LENGTH: 21
<212> TYPE: DNA
<213> ORGANISM: Artificial sequence
<220> FEATURE:
<223> OTHER INFORMATION: Oligonucleotide sequences of siRNAs specific
      for TGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 2, 5, 8, 10, 11, 12, 14, 17, 18
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1, 3, 4, 6, 7, 9, 13, 15, 16, 19
<223> OTHER INFORMATION: /mod_base = "2'-hydroxy corresponding base"

<400> SEQUENCE: 71
```
acaacagcac ccgcgaccgt t                                              21

<210> SEQ ID NO 72
<211> LENGTH: 21
<212> TYPE: DNA
<213> ORGANISM: Artificial sequence
<220> FEATURE:
<223> OTHER INFORMATION: Oligonucleotide sequences of siRNAs specific
      for TGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1..19
<223> OTHER INFORMATION: /mod_base = "2'-hydroxy corresponding base"

<400> SEQUENCE: 72
cggucgcggg ugcuguugut t                                              21

<210> SEQ ID NO 73
<211> LENGTH: 21
<212> TYPE: DNA
<213> ORGANISM: Artificial sequence
<220> FEATURE:
<223> OTHER INFORMATION: Oligonucleotide sequences of siRNAs specific
      for TGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 73
caagggcuac caugccaact t                                              21

<210> SEQ ID NO 74
<211> LENGTH: 21
<212> TYPE: DNA
<213> ORGANISM: Artificial sequence
<220> FEATURE:
<223> OTHER INFORMATION: Oligonucleotide sequences of siRNAs specific
      for TGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 74
guuggcaugg uagcccuugt t                                              21

<210> SEQ ID NO 75
<211> LENGTH: 21
<212> TYPE: DNA
<213> ORGANISM: Artificial sequence
<220> FEATURE:
<223> OTHER INFORMATION: Oligonucleotide sequences of siRNAs specific
      for TGF-beta
<220> FEATURE:
<223> OTHER INFORMATION: 5'-terminal nucleic acid is a nucleoside, i.e.
      base + sugar but lacking 5'-phosphate
<220> FEATURE:

```
<221> NAME/KEY: modified_base
<222> LOCATION: 1, 7, 8, 10, 11, 13, 15, 16, 19
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 2, 3, 4, 5, 6, 9, 12, 14, 17, 18
<223> OTHER INFORMATION: /mod_base = "2'-hydroxy corresponding base"

<400> SEQUENCE: 75
caagggcuac caugccaact t                                              21

<210> SEQ ID NO 76
<211> LENGTH: 21
<212> TYPE: DNA
<213> ORGANISM: Artificial sequence
<220> FEATURE:
<223> OTHER INFORMATION: Oligonucleotide sequences of siRNAs specific
      for TGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 6, 11
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1, 2, 3, 4, 5, 7, 8, 9, 10, 12, 13, 14, 15, 16, 17, 18,
      19
<223> OTHER INFORMATION: /mod_base = "2'-hydroxy corresponding base"

<400> SEQUENCE: 76
guuggcaugg uagcccuugt t                                              21

<210> SEQ ID NO 77
<211> LENGTH: 21
<212> TYPE: DNA
<213> ORGANISM: Artificial sequence
<220> FEATURE:
<223> OTHER INFORMATION: Oligonucleotide sequences of siRNAs specific
      for TGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 77
ccggaccagc ccucgggagt t                                              21

<210> SEQ ID NO 78
<211> LENGTH: 21
<212> TYPE: DNA
<213> ORGANISM: Artificial sequence
<220> FEATURE:
<223> OTHER INFORMATION: Oligonucleotide sequences of siRNAs specific
      for TGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
```

<223> OTHER INFORMATION: /mod_base = "2'-hydroxy corresponding base"

<400> SEQUENCE: 78
cucccgaggg cugguccggt t                                              21

<210> SEQ ID NO 79
<211> LENGTH: 21
<212> TYPE: DNA
<213> ORGANISM: Artificial sequence
<220> FEATURE:
<223> OTHER INFORMATION: Oligonucleotide sequences of siRNAs specific
      for TGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1, 2, 6, 7, 10, 11, 12, 13, 14
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 3, 4, 5, 8, 9, 15, 16, 17, 18, 19
<223> OTHER INFORMATION: /mod_base = "2'-hydroxy corresponding base"

<400> SEQUENCE: 79
ccggaccagc ccucgggagt t                                              21

<210> SEQ ID NO 80
<211> LENGTH: 21
<212> TYPE: DNA
<213> ORGANISM: Artificial sequence
<220> FEATURE:
<223> OTHER INFORMATION: Oligonucleotide sequences of siRNAs specific
      for TGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1..19
<223> OTHER INFORMATION: /mod_base = "2'-hydroxy corresponding base"

<400> SEQUENCE: 80
cucccgaggg cugguccggt t                                              21

<210> SEQ ID NO 81
<211> LENGTH: 21
<212> TYPE: DNA
<213> ORGANISM: Artificial sequence
<220> FEATURE:
<223> OTHER INFORMATION: Oligonucleotide sequences of siRNAs specific
      for TGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 81
caacuauugc uucagcucct t                                              21

<210> SEQ ID NO 82
<211> LENGTH: 21
<212> TYPE: DNA
<213> ORGANISM: Artificial sequence
<220> FEATURE:
<223> OTHER INFORMATION: Oligonucleotide sequences of siRNAs specific
      for TGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 82
ggagcugaag caauaguugt t                                              21

<210> SEQ ID NO 83
<211> LENGTH: 21
<212> TYPE: DNA
<213> ORGANISM: Artificial sequence
<220> FEATURE:
<223> OTHER INFORMATION: Oligonucleotide sequences of siRNAs specific
      for TGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1, 4, 5, 7, 8, 10, 11, 12, 13, 16, 17, 18, 19
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 2, 3, 6, 9, 14, 15
<223> OTHER INFORMATION: /mod_base = "2'-hydroxy corresponding base"

<400> SEQUENCE: 83
caacuauugc uucagcucct t                                              21

<210> SEQ ID NO 84
<211> LENGTH: 21
<212> TYPE: DNA
<213> ORGANISM: Artificial sequence
<220> FEATURE:
<223> OTHER INFORMATION: Oligonucleotide sequences of siRNAs specific
      for TGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 11, 14
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1, 2, 3, 4, 5, 6, 7, 8, 9, 10, 12, 13, 15, 16, 17, 18,
      19
<223> OTHER INFORMATION: /mod_base = "2'-hydroxy corresponding base"

<400> SEQUENCE: 84
ggagcugaag caauaguugt t                                              21

<210> SEQ ID NO 85
<211> LENGTH: 21

```
<212> TYPE: DNA
<213> ORGANISM: Artificial sequence
<220> FEATURE:
<223> OTHER INFORMATION: Oligonucleotide sequences of siRNAs specific
      for TGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 85
gugcggcagc uguacauugt t                                              21

<210> SEQ ID NO 86
<211> LENGTH: 21
<212> TYPE: DNA
<213> ORGANISM: Artificial sequence
<220> FEATURE:
<223> OTHER INFORMATION: Oligonucleotide sequences of siRNAs specific
      for TGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 86
caauguacag cugccgcact t                                              21

<210> SEQ ID NO 87
<211> LENGTH: 21
<212> TYPE: DNA
<213> ORGANISM: Artificial sequence
<220> FEATURE:
<223> OTHER INFORMATION: Oligonucleotide sequences of siRNAs specific
      for TGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 2, 4, 7, 10, 11, 13, 15, 17, 18
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1, 3, 5, 6, 8, 9, 12, 14, 16, 19
<223> OTHER INFORMATION: /mod_base = "2'-hydroxy corresponding base"

<400> SEQUENCE: 87
gugcggcagc uguacauugt t                                              21

<210> SEQ ID NO 88
<211> LENGTH: 21
<212> TYPE: DNA
<213> ORGANISM: Artificial sequence
<220> FEATURE:
<223> OTHER INFORMATION: Oligonucleotide sequences of siRNAs specific
      for TGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1, 6, 8, 17
```

```
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 2, 3, 4, 5, 7, 9, 10, 11, 12, 13, 14, 15, 16, 18, 19
<223> OTHER INFORMATION: /mod_base = "2'-hydroxy corresponding base"

<400> SEQUENCE: 88
caauguacag cugccgcact t                                              21

<210> SEQ ID NO 89
<211> LENGTH: 21
<212> TYPE: DNA
<213> ORGANISM: Artificial sequence
<220> FEATURE:
<223> OTHER INFORMATION: Oligonucleotide sequences of siRNAs specific
      for TGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 89
ggaaguggau ccacgagcct t                                              21

<210> SEQ ID NO 90
<211> LENGTH: 21
<212> TYPE: DNA
<213> ORGANISM: Artificial sequence
<220> FEATURE:
<223> OTHER INFORMATION: Oligonucleotide sequences of siRNAs specific
      for TGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 90
ggcucgugga uccacuucct t                                              21

<210> SEQ ID NO 91
<211> LENGTH: 21
<212> TYPE: DNA
<213> ORGANISM: Artificial sequence
<220> FEATURE:
<223> OTHER INFORMATION: Oligonucleotide sequences of siRNAs specific
      for TGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 6, 10, 11, 12, 14, 18, 19
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1, 2, 3, 4, 5, 7, 8, 9, 13, 15, 16, 17
<223> OTHER INFORMATION: /mod_base = "2'-hydroxy corresponding base"

<400> SEQUENCE: 91
```
ggaaguggau ccacgagcct t               21

<210> SEQ ID NO 92
<211> LENGTH: 21
<212> TYPE: DNA
<213> ORGANISM: Artificial sequence
<220> FEATURE:
<223> OTHER INFORMATION: Oligonucleotide sequences of siRNAs specific
      for TGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 13
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1, 2, 3, 4, 5, 6, 7, 8, 9, 10, 11, 12, 14, 15, 16, 17,
      18, 19
<223> OTHER INFORMATION: /mod_base = "2'-hydroxy corresponding base"

<400> SEQUENCE: 92
ggcucgugga uccacuucct t               21

<210> SEQ ID NO 93
<211> LENGTH: 21
<212> TYPE: DNA
<213> ORGANISM: Artificial sequence
<220> FEATURE:
<223> OTHER INFORMATION: Oligonucleotide sequences of siRNAs specific
      for TGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 93
gaaguggauc cacgagccct t               21

<210> SEQ ID NO 94
<211> LENGTH: 21
<212> TYPE: DNA
<213> ORGANISM: Artificial sequence
<220> FEATURE:
<223> OTHER INFORMATION: Oligonucleotide sequences of siRNAs specific
      for TGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 94
gggcucgugg auccacuuct t               21

<210> SEQ ID NO 95
<211> LENGTH: 21
<212> TYPE: DNA
<213> ORGANISM: Artificial sequence
<220> FEATURE:
<223> OTHER INFORMATION: Oligonucleotide sequences of siRNAs specific for TGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 5, 9, 10, 11, 13, 17, 18, 19
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1, 2, 3, 4, 6, 7, 8, 12, 14, 15, 16
<223> OTHER INFORMATION: /mod_base = "2'-hydroxy corresponding base"

<400> SEQUENCE: 95
gaaguggauc cacgagcccu t                                              21

<210> SEQ ID NO 96
<211> LENGTH: 21
<212> TYPE: DNA
<213> ORGANISM: Artificial sequence
<220> FEATURE:
<223> OTHER INFORMATION: Oligonucleotide sequences of siRNAs specific
      for TGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 14
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1, 2, 3, 4, 5, 6, 7, 8, 9, 10, 11, 12, 13, 15, 16, 17,
      18, 19
<223> OTHER INFORMATION: /mod_base = "2'-hydroxy corresponding base"

<400> SEQUENCE: 96
gggcucgugg auccacuuct t                                              21

<210> SEQ ID NO 97
<211> LENGTH: 21
<212> TYPE: DNA
<213> ORGANISM: Artificial sequence
<220> FEATURE:
<223> OTHER INFORMATION: Oligonucleotide sequences of siRNAs specific
      for TGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 97
ccacgagccc aagggcuact t                                              21

<210> SEQ ID NO 98
<211> LENGTH: 21
<212> TYPE: DNA
<213> ORGANISM: Artificial sequence
<220> FEATURE:
<223> OTHER INFORMATION: Oligonucleotide sequences of siRNAs specific
      for TGF-beta
<220> FEATURE:

-continued

```
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 98
guagcccuug ggcucguggt t                                              21

<210> SEQ ID NO 99
<211> LENGTH: 21
<212> TYPE: DNA
<213> ORGANISM: Artificial sequence
<220> FEATURE:
<223> OTHER INFORMATION: Oligonucleotide sequences of siRNAs specific
      for TGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1, 2, 4, 8, 9, 10, 16, 17, 19
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 3, 5, 6, 7, 11, 12, 13, 14, 15, 18
<223> OTHER INFORMATION: /mod_base = "2'-hydroxy corresponding base"

<400> SEQUENCE: 99
ccacgagccc aagggcuact t                                              21

<210> SEQ ID NO 100
<211> LENGTH: 21
<212> TYPE: DNA
<213> ORGANISM: Artificial sequence
<220> FEATURE:
<223> OTHER INFORMATION: Oligonucleotide sequences of siRNAs specific
      for TGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 2
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1, 3, 4, 5, 6, 7, 8, 9, 10, 11, 12, 13, 14, 15, 16, 17,
      18, 19
<223> OTHER INFORMATION: /mod_base = "2'-hydroxy corresponding base"

<400> SEQUENCE: 100
guagcccuug ggcucguggt t                                              21

<210> SEQ ID NO 101
<211> LENGTH: 21
<212> TYPE: DNA
<213> ORGANISM: Artificial sequence
<220> FEATURE:
<223> OTHER INFORMATION: Oligonucleotide sequences of siRNAs specific
      for TGF-beta
<220> FEATURE:
<223> OTHER INFORMATION: 5'-terminal nucleic acid is a nucleoside, i.e.
      base + sugar but lacking 5'-phosphate
```

```
<220> FEATURE:
<221> NAME/KEY: modified_base
<222> LOCATION: 1..19
<223> OTHER INFORMATION: /mod_base = "2'-hydroxy corresponding base"

<400> SEQUENCE: 101
gagcccaagg gcuaccaugt t                                              21

<210> SEQ ID NO 102
<211> LENGTH: 21
<212> TYPE: DNA
<213> ORGANISM: Artificial sequence
<220> FEATURE:
<223> OTHER INFORMATION: Oligonucleotide sequences of siRNAs specific
      for TGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 102
caugguagcc cuugggcuct t                                              21

<210> SEQ ID NO 103
<211> LENGTH: 21
<212> TYPE: DNA
<213> ORGANISM: Artificial sequence
<220> FEATURE:
<223> OTHER INFORMATION: Oligonucleotide sequences of siRNAs specific
      for TGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 4, 5, 6, 12, 13, 15, 16, 18
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1, 2, 3, 7, 8, 9, 10, 11, 14, 17, 19
<223> OTHER INFORMATION: /mod_base = "2'-hydroxy corresponding base"

<400> SEQUENCE: 103
gagcccaagg gcuaccaugt t                                              21

<210> SEQ ID NO 104
<211> LENGTH: 21
<212> TYPE: DNA
<213> ORGANISM: Artificial sequence
<220> FEATURE:
<223> OTHER INFORMATION: Oligonucleotide sequences of siRNAs specific
      for TGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1, 6
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 2, 3, 4, 5, 7, 8, 9, 10, 11, 12, 13, 14, 15, 16, 17, 18,
```

19
<223> OTHER INFORMATION: /mod_base = "2'-hydroxy corresponding base"

<400> SEQUENCE: 104
caugguagcc cuugggcuct t                                              21

<210> SEQ ID NO 105
<211> LENGTH: 21
<212> TYPE: DNA
<213> ORGANISM: Artificial sequence
<220> FEATURE:
<223> OTHER INFORMATION: Oligonucleotide sequences of siRNAs specific
      for TGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 105
agcccaaggg cuaccaugct t                                              21

<210> SEQ ID NO 106
<211> LENGTH: 21
<212> TYPE: DNA
<213> ORGANISM: Artificial sequence
<220> FEATURE:
<223> OTHER INFORMATION: Oligonucleotide sequences of siRNAs specific
      for TGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 106
gcaugguagc ccuugggcut t                                              21

<210> SEQ ID NO 107
<211> LENGTH: 21
<212> TYPE: DNA
<213> ORGANISM: Artificial sequence
<220> FEATURE:
<223> OTHER INFORMATION: Oligonucleotide sequences of siRNAs specific
      for TGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 3, 4, 5, 11, 12, 14, 15, 17, 19
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1, 2, 6, 7, 8, 9, 10, 13, 16, 18
<223> OTHER INFORMATION: /mod_base = "2'-hydroxy corresponding base"

<400> SEQUENCE: 107
agcccaaggg cuaccaugct t                                              21

<210> SEQ ID NO 108
<211> LENGTH: 21
<212> TYPE: DNA

<213> ORGANISM: Artificial sequence
<220> FEATURE:
<223> OTHER INFORMATION: Oligonucleotide sequences of siRNAs specific
for TGF-beta
<220> FEATURE:
<223> OTHER INFORMATION: 5'-terminal nucleic acid is a nucleoside, i.e.
base + sugar but lacking 5'-phosphate
<220> FEATURE:
<221> NAME/KEY: modified_base
<222> LOCATION: 2, 7
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1, 3, 4, 5, 6, 8, 9, 10, 11, 12, 13, 14, 15, 16, 17, 18,
19
<223> OTHER INFORMATION: /mod_base = "2'-hydroxy corresponding base"

<400> SEQUENCE: 108
gcaugguagc ccuugggcut t         21

<210> SEQ ID NO 109
<211> LENGTH: 21
<212> TYPE: DNA
<213> ORGANISM: Artificial sequence
<220> FEATURE:
<223> OTHER INFORMATION: Oligonucleotide sequences of siRNAs specific
for TGF-beta
<220> FEATURE:
<223> OTHER INFORMATION: 5'-terminal nucleic acid is a nucleoside, i.e.
base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 109
cgugcugcgu gccgcaggct t         21

<210> SEQ ID NO 110
<211> LENGTH: 21
<212> TYPE: DNA
<213> ORGANISM: Artificial sequence
<220> FEATURE:
<223> OTHER INFORMATION: Oligonucleotide sequences of siRNAs specific
for TGF-beta
<220> FEATURE:
<223> OTHER INFORMATION: 5'-terminal nucleic acid is a nucleoside, i.e.
base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 110
gccugcggca cgcagcacgt t         21

<210> SEQ ID NO 111
<211> LENGTH: 21
<212> TYPE: DNA
<213> ORGANISM: Artificial sequence
<220> FEATURE:
<223> OTHER INFORMATION: Oligonucleotide sequences of siRNAs specific
for TGF-beta
<220> FEATURE:
<223> OTHER INFORMATION: 5'-terminal nucleic acid is a nucleoside, i.e.
base + sugar but lacking 5'-phosphate
<220> FEATURE:
<221> NAME/KEY: modified_base
<222> LOCATION: 1, 3, 5, 6, 8, 10, 12, 13, 15, 19

-continued

```
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 2, 4, 7, 9, 11, 14, 16, 17, 18
<223> OTHER INFORMATION: /mod_base = "2'-hydroxy corresponding base"

<400> SEQUENCE: 111
cgugcugcgu gccgcaggct t                                              21

<210> SEQ ID NO 112
<211> LENGTH: 21
<212> TYPE: DNA
<213> ORGANISM: Artificial sequence
<220> FEATURE:
<223> OTHER INFORMATION: Oligonucleotide sequences of siRNAs specific
      for TGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 9, 13, 16
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1, 2, 3, 4, 5, 6, 7, 8, 10, 11, 12, 14, 15, 17, 18, 19
<223> OTHER INFORMATION: /mod_base = "2'-hydroxy corresponding base"

<400> SEQUENCE: 112
gccugcggca cgcagcacgt t                                              21

<210> SEQ ID NO 113
<211> LENGTH: 41
<212> TYPE: DNA
<213> ORGANISM: Artificial sequence
<220> FEATURE:
<223> OTHER INFORMATION: TGF-beta-specific probes detecting hsTGF-beta1
      (Genbank accession no. NM_000660.3)

<400> SEQUENCE: 113
gggctccggt tctgcactct tttttctctt ggaaagaaag t                        41

<210> SEQ ID NO 114
<211> LENGTH: 39
<212> TYPE: DNA
<213> ORGANISM: Artificial sequence
<220> FEATURE:
<223> OTHER INFORMATION: TGF-beta-specific probes detecting hsTGF-beta1
      (Genbank accession no. NM_000660.3)

<400> SEQUENCE: 114
cgcgggtgac ctccttggtt tttctcttgg aaagaaagt                           39

<210> SEQ ID NO 115
<211> LENGTH: 39
<212> TYPE: DNA
<213> ORGANISM: Artificial sequence
<220> FEATURE:
<223> OTHER INFORMATION: TGF-beta-specific probes detecting hsTGF-beta1
      (Genbank accession no. NM_000660.3)

<400> SEQUENCE: 115
```

```
gcagctctgc ccgggagatt tttctcttgg aaagaaagt                              39
```

<210> SEQ ID NO 116
<211> LENGTH: 44
<212> TYPE: DNA
<213> ORGANISM: Artificial sequence
<220> FEATURE:
<223> OTHER INFORMATION: TGF-beta-specific probes detecting hsTGF-beta1
      (Genbank accession no. NM_000660.3)

<400> SEQUENCE: 116

```
ttttaacttg agcctcagca gacttttttct cttggaaaga aagt                       44
```

<210> SEQ ID NO 117
<211> LENGTH: 41
<212> TYPE: DNA
<213> ORGANISM: Artificial sequence
<220> FEATURE:
<223> OTHER INFORMATION: TGF-beta-specific probes detecting hsTGF-beta1
      (Genbank accession no. NM_000660.3)

<400> SEQUENCE: 117

```
ggttgctgag gtatcgccag ttttttctctt ggaaagaaag t                          41
```

<210> SEQ ID NO 118
<211> LENGTH: 38
<212> TYPE: DNA
<213> ORGANISM: Artificial sequence
<220> FEATURE:
<223> OTHER INFORMATION: TGF-beta-specific probes detecting hsTGF-beta1
      (Genbank accession no. NM_000660.3)

<400> SEQUENCE: 118

```
gctgggtgcc agcagccttt ttctcttgga aagaaagt                               38
```

<210> SEQ ID NO 119
<211> LENGTH: 46
<212> TYPE: DNA
<213> ORGANISM: Artificial sequence
<220> FEATURE:
<223> OTHER INFORMATION: TGF-beta-specific probes detecting hsTGF-beta1
      (Genbank accession no. NM_000660.3)

<400> SEQUENCE: 119

```
cgtagtagtc ggcctcaggc tcttttttagg cataggaccc gtgtct                     46
```

<210> SEQ ID NO 120
<211> LENGTH: 45
<212> TYPE: DNA
<213> ORGANISM: Artificial sequence
<220> FEATURE:
<223> OTHER INFORMATION: TGF-beta-specific probes detecting hsTGF-beta1
      (Genbank accession no. NM_000660.3)

<400> SEQUENCE: 120

```
tgtgggtttc caccattagc attttttaggc ataggacccg tgtct                      45
```

<210> SEQ ID NO 121
<211> LENGTH: 46
<212> TYPE: DNA
<213> ORGANISM: Artificial sequence
<220> FEATURE:
<223> OTHER INFORMATION: TGF-beta-specific probes detecting hsTGF-beta1
      (Genbank accession no. NM_000660.3)

<400> SEQUENCE: 121

```
gcttctcgga gctctgatgt gttttttagg cataggaccc gtgtct                      46
```

<210> SEQ ID NO 122
<211> LENGTH: 44
<212> TYPE: DNA
<213> ORGANISM: Artificial sequence
<220> FEATURE:
<223> OTHER INFORMATION: TGF-beta-specific probes detecting hsTGF-beta1
      (Genbank accession no. NM_000660.3)

<400> SEQUENCE: 122
gcaacacggg ttcaggtacc tttttaggca taggacccgt gtct                    44

<210> SEQ ID NO 123
<211> LENGTH: 49
<212> TYPE: DNA
<213> ORGANISM: Artificial sequence
<220> FEATURE:
<223> OTHER INFORMATION: TGF-beta-specific probes detecting hsTGF-beta1
      (Genbank accession no. NM_000660.3)

<400> SEQUENCE: 123
gaattgttgc tgtatttctg gtacattttt aggcatagga cccgtgtct               49

<210> SEQ ID NO 124
<211> LENGTH: 25
<212> TYPE: DNA
<213> ORGANISM: Artificial sequence
<220> FEATURE:
<223> OTHER INFORMATION: TGF-beta-specific probes detecting hsTGF-beta1
      (Genbank accession no. NM_000660.3)

<400> SEQUENCE: 124
tgcttgaact tgtcatagat ttcgt                                         25

<210> SEQ ID NO 125
<211> LENGTH: 29
<212> TYPE: DNA
<213> ORGANISM: Artificial sequence
<220> FEATURE:
<223> OTHER INFORMATION: TGF-beta-specific probes detecting hsTGF-beta1
      (Genbank accession no. NM_000660.3)

<400> SEQUENCE: 125
tgaagaacat atatatgctg tgtgtactc                                     29

<210> SEQ ID NO 126
<211> LENGTH: 19
<212> TYPE: DNA
<213> ORGANISM: Artificial sequence
<220> FEATURE:
<223> OTHER INFORMATION: TGF-beta-specific probes detecting hsTGF-beta1
      (Genbank accession no. NM_000660.3)

<400> SEQUENCE: 126
gctccacgtg ctgctccac                                                19

<210> SEQ ID NO 127
<211> LENGTH: 41
<212> TYPE: DNA
<213> ORGANISM: Artificial sequence
<220> FEATURE:
<223> OTHER INFORMATION: GAPDH-specific probes detecting hsGAPDH
      (Genbank accession no. NM_002046.2)

<400> SEQUENCE: 127
gaatttgcca tgggtggaat tttttctctt ggaaagaaag t                       41

```
<210> SEQ ID NO 128
<211> LENGTH: 41
<212> TYPE: DNA
<213> ORGANISM: Artificial sequence
<220> FEATURE:
<223> OTHER INFORMATION: GAPDH-specific probes detecting hsGAPDH
      (Genbank accession no. NM_002046.2)

<400> SEQUENCE: 128
ggagggatct cgctcctgga tttttctctt ggaaagaaag t                41

<210> SEQ ID NO 129
<211> LENGTH: 40
<212> TYPE: DNA
<213> ORGANISM: Artificial sequence
<220> FEATURE:
<223> OTHER INFORMATION: GAPDH-specific probes detecting hsGAPDH
      (Genbank accession no. NM_002046.2)

<400> SEQUENCE: 129
ccccagcctt ctccatggtt tttctcttg gaaagaaagt                   40

<210> SEQ ID NO 130
<211> LENGTH: 40
<212> TYPE: DNA
<213> ORGANISM: Artificial sequence
<220> FEATURE:
<223> OTHER INFORMATION: GAPDH-specific probes detecting hsGAPDH
      (Genbank accession no. NM_002046.2)

<400> SEQUENCE: 130 gctccccct gcaaatgagt tttctcttg gaaagaaagt                    40

<210> SEQ ID NO 131
<211> LENGTH: 42
<212> TYPE: DNA
<213> ORGANISM: Artificial sequence
<220> FEATURE:
<223> OTHER INFORMATION: GAPDH-specific probes detecting hsGAPDH
      (Genbank accession no. NM_002046.2)

<400> SEQUENCE: 131
agccttgacg gtgccatgtt tttaggcata ggacccgtgt ct               42

<210> SEQ ID NO 132
<211> LENGTH: 45
<212> TYPE: DNA
<213> ORGANISM: Artificial sequence
<220> FEATURE:
<223> OTHER INFORMATION: GAPDH-specific probes detecting hsGAPDH
      (Genbank accession no. NM_002046.2)

<400> SEQUENCE: 132
gatgacaagc ttcccgttct cttttaggc ataggacccg tgtct             45

<210> SEQ ID NO 133
<211> LENGTH: 46
<212> TYPE: DNA
<213> ORGANISM: Artificial sequence
<220> FEATURE:
<223> OTHER INFORMATION: GAPDH-specific probes detecting hsGAPDH
      (Genbank accession no. NM_002046.2)

<400> SEQUENCE: 133
agatggtgat gggatttcca ttttttagg cataggaccc gtgtct            46
```

<210> SEQ ID NO 134
<211> LENGTH: 44
<212> TYPE: DNA
<213> ORGANISM: Artificial sequence
<220> FEATURE:
<223> OTHER INFORMATION: GAPDH-specific probes detecting hsGAPDH
      (Genbank accession no. NM_002046.2)

<400> SEQUENCE: 134
gcatcgcccc acttgatttt tttttaggca taggacccgt gtct                44

<210> SEQ ID NO 135
<211> LENGTH: 43
<212> TYPE: DNA
<213> ORGANISM: Artificial sequence
<220> FEATURE:
<223> OTHER INFORMATION: GAPDH-specific probes detecting hsGAPDH
      (Genbank accession no. NM_002046.2)

<400> SEQUENCE: 135
cacgacgtac tcagcgccat ttttaggcat aggacccgtg tct                 43

<210> SEQ ID NO 136
<211> LENGTH: 46
<212> TYPE: DNA
<213> ORGANISM: Artificial sequence
<220> FEATURE:
<223> OTHER INFORMATION: GAPDH-specific probes detecting hsGAPDH
      (Genbank accession no. NM_002046.2)

<400> SEQUENCE: 136
ggcagagatg atgacccttt tgtttttagg cataggaccc gtgtct              46

<210> SEQ ID NO 137
<211> LENGTH: 21
<212> TYPE: DNA
<213> ORGANISM: Artificial sequence
<220> FEATURE:
<223> OTHER INFORMATION: GAPDH-specific probes detecting hsGAPDH
      (Genbank accession no. NM_002046.2)

<400> SEQUENCE: 137
ggtgaagacg ccagtggact c                                         21

<210> SEQ ID NO 138
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 138
aauuccuggc gauaccucat t                                         21

<210> SEQ ID NO 139
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.

-continued

```
     base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 139
ugagguaucg ccaggaauut t                                          21

<210> SEQ ID NO 140
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 140
ucgcgcccau cuagguuaut t                                          21

<210> SEQ ID NO 141
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 141
auaaccuaga ugggcgcgat t                                          21

<210> SEQ ID NO 142
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 142
ggucacccgc gugcuaaugt t                                          21

<210> SEQ ID NO 143
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
```

-continued

<222> LOCATION: 1..19
<223> OTHER INFORMATION: /mod_base = "2'-hydroxy corresponding base"

<400> SEQUENCE: 143
cauuagcacg cgggugacct t         21

<210> SEQ ID NO 144
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
    base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 144
aggucacccg cgugcuaaut t         21

<210> SEQ ID NO 145
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
    base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 145
auuagcacgc gggugaccut t         21

<210> SEQ ID NO 146
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
    base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 146
cacccgcgug cuauggugt t         21

<210> SEQ ID NO 147
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
    base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

```
<400> SEQUENCE: 147
caccauuagc acgcgggugt t                                              21

<210> SEQ ID NO 148
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 148
uacaaccagc auaacccggt t                                              21

<210> SEQ ID NO 149
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 149
ccggguuaug cugguuguat t                                              21

<210> SEQ ID NO 150
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 150
aucgcgccca ucuagguuat t                                              21

<210> SEQ ID NO 151
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 151
uaaccuagau gggcgcgaut t                                              21
```

```
<210> SEQ ID NO 152
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 152
guaccagauc gcgcccauct t                                              21

<210> SEQ ID NO 153
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 153
gaugggcgcg aucugguact t                                              21

<210> SEQ ID NO 154
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 154
agacggaucu cucuccgact t                                              21

<210> SEQ ID NO 155
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 155
gucggagaga gauccgucut t                                              21

<210> SEQ ID NO 156
```

```
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 156
cgcgcccauc uagguuauut t                                              21

<210> SEQ ID NO 157
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 157
aauaaccuag augggcgcgt t                                              21

<210> SEQ ID NO 158
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 158
cccgcgcauc cuagacccut t                                              21

<210> SEQ ID NO 159
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 159
agggucuagg augcgcgggt t                                              21

<210> SEQ ID NO 160
<211> LENGTH: 21
<212> TYPE: DNA
<213> ORGANISM: Artificial sequence
```

```
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 160
gcgcccaucu agguuauuut t                                              21

<210> SEQ ID NO 161
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 161
aaauaaccua gaugggcgct t                                              21

<210> SEQ ID NO 162
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 162
uccgugggau acugagacat t                                              21

<210> SEQ ID NO 163
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 163
ugucucagua ucccacggat t                                              21

<210> SEQ ID NO 164
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
```

```
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 164
cuuucgccuu agcgcccact t                                                    21

<210> SEQ ID NO 165
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 165
gugggcgcua aggcgaaagt t                                                    21

<210> SEQ ID NO 166
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 166
acccgcgugc uaaugguggt t                                                    21

<210> SEQ ID NO 167
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 167
ccaccauuag cacgcgggut t                                                    21

<210> SEQ ID NO 168
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
```

```
<221> NAME/KEY: modified_base
<222> LOCATION: 1..19
<223> OTHER INFORMATION: /mod_base = "2'-hydroxy corresponding base"

<400> SEQUENCE: 168
gcaacaauuc cuggcgauat t                                            21

<210> SEQ ID NO 169
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 169
uaucgccagg aauuguugct t                                            21

<210> SEQ ID NO 170
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 170
aacggguuca cuaccggcct t                                            21

<210> SEQ ID NO 171
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 171
ggccgguagu gaacccguut t                                            21

<210> SEQ ID NO 172
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"
```

<400> SEQUENCE: 172
cggguucacu accggccgct t                                              21

<210> SEQ ID NO 173
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 173
gcggccggua gugaacccgt t                                              21

<210> SEQ ID NO 174
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 174
cuguauuuaa ggacacccgt t                                              21

<210> SEQ ID NO 175
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 175
cggguguccu uaaauacagt t                                              21

<210> SEQ ID NO 176
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 176

-continued agguuauuuc cgugggauat t    21

<210> SEQ ID NO 177
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 177
uaucccacgg aaauaaccut t    21

<210> SEQ ID NO 178
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 178
cccucgggag ucgccgacct t    21

<210> SEQ ID NO 179
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 179
ggucggcgac ucccgagggt t    21

<210> SEQ ID NO 180
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 180
ugugcggcag ugguugagct t    21

```
<210> SEQ ID NO 181
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 181
gcucaaccac ugccgcacat t                                              21

<210> SEQ ID NO 182
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 182
caaccagcau aacccgggct t                                              21

<210> SEQ ID NO 183
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 183
gcccggguua ugcugguugt t                                              21

<210> SEQ ID NO 184
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 184
uuuugagacu uuuccguugt t                                              21

<210> SEQ ID NO 185
<211> LENGTH: 21
<212> TYPE: DNA
```

```
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 185
caacggaaaa gucucaaaat t                                             21

<210> SEQ ID NO 186
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 186
uuugagacuu uuccguugct t                                             21

<210> SEQ ID NO 187
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 187
gcaacggaaa agucucaaat t                                             21

<210> SEQ ID NO 188
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 188
cucuuggcgc gacgcugcct t                                             21

<210> SEQ ID NO 189
<211> LENGTH: 21
<212> TYPE: DNA
<213> ORGANISM: Artificial sequence
<220> FEATURE:
<223> OTHER INFORMATION: Additional RNAi agents targeting hTGF-beta
```

```
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 189
ggcagcgucg cgccaagagt t                                               21

<210> SEQ ID NO 190
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 190
ucugguacca gaucgcgcct t                                               21

<210> SEQ ID NO 191
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 191
ggcgcgaucu gguaccagat t                                               21

<210> SEQ ID NO 192
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 192
acaccagccc uguucgcgct t                                               21

<210> SEQ ID NO 193
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
```

```
<220> FEATURE:
<221> NAME/KEY: modified_base
<222> LOCATION: 1..19
<223> OTHER INFORMATION: /mod_base = "2'-hydroxy corresponding base"

<400> SEQUENCE: 193
gcgcgaacag ggcuggugut t                                              21

<210> SEQ ID NO 194
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 194
cggccggccg cgggacuaut t                                              21

<210> SEQ ID NO 195
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 195
auagucccgc ggccggccgt t                                              21

<210> SEQ ID NO 196
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 196
gguaccugaa cccguguugt t                                              21

<210> SEQ ID NO 197
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
```

<223> OTHER INFORMATION: /mod_base = "2'-hydroxy corresponding base"

<400> SEQUENCE: 197
caacacgggu ucagguacct t                                               21

<210> SEQ ID NO 198
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 198
guaccugaac ccguguugct t                                               21

<210> SEQ ID NO 199
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 199
gcaacacggg uucagguact t                                               21

<210> SEQ ID NO 200
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 200
auuccuggcg auaccucagt t                                               21

<210> SEQ ID NO 201
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 201
cugagguauc gccaggaaut t                                                    21

<210> SEQ ID NO 202
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 202
auugagggcu uucgccuuat t                                                    21

<210> SEQ ID NO 203
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 203
uaaggcgaaa gcccucaaut t                                                    21

<210> SEQ ID NO 204
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 204
acaaccagca uaacccgggt t                                                    21

<210> SEQ ID NO 205
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 205
cccggguuau gcugguugut t                                                    21

<210> SEQ ID NO 206
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 206
uguauuuaag gacacccgut t                                            21

<210> SEQ ID NO 207
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 207 acggugucc uuaaauacat t                                             21

<210> SEQ ID NO 208
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 208
gaggacugcg gaucucugut t                                            21

<210> SEQ ID NO 209
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 209
acagagaucc gcaguccuct t                                            21

<210> SEQ ID NO 210
<211> LENGTH: 21

```
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 210
gggaacacua cuguaguuat t                                               21

<210> SEQ ID NO 211
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 211
uaacuacagu aguguuccct t                                               21

<210> SEQ ID NO 212
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 212
accagcccug uucgcgcuct t                                               21

<210> SEQ ID NO 213
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 213
gagcgcgaac agggcuggut t                                               21

<210> SEQ ID NO 214
<211> LENGTH: 21
<212> TYPE: DNA
<213> ORGANISM: Artificial sequence
<220> FEATURE:
```

<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 214
agaggacugc ggaucucugt t                                              21

<210> SEQ ID NO 215
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 215
cagagauccg caguccucut t                                              21

<210> SEQ ID NO 216
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 216
guacuacgug ggccgcaagt t                                              21

<210> SEQ ID NO 217
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 217
cuugcggccc acguaguact t                                              21

<210> SEQ ID NO 218
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.

base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 218
gaucgcgccc aucuagguut t                                              21

<210> SEQ ID NO 219
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 219
aaccuagaug ggcgcgauct t                                              21

<210> SEQ ID NO 220
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 220
aacgaaaucu augacaagut t                                              21

<210> SEQ ID NO 221
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 221
acuugucaua gauuucguut t                                              21

<210> SEQ ID NO 222
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base

```
<222> LOCATION: 1..19
<223> OTHER INFORMATION: /mod_base = "2'-hydroxy corresponding base"

<400> SEQUENCE: 222
uucgccuuag cgcccacugt t                                              21

<210> SEQ ID NO 223
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 223
cagugggcgc uaaggcgaat t                                              21

<210> SEQ ID NO 224
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 224
aucaacgggu ucacuaccgt t                                              21

<210> SEQ ID NO 225
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 225
cgguagugaa cccguugaut t                                              21

<210> SEQ ID NO 226
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"
```

```
<400> SEQUENCE: 226
ccgcgcaucc uagacccuut t                                              21

<210> SEQ ID NO 227
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 227
aagggucuag gaugcgcggt t                                              21

<210> SEQ ID NO 228
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 228
gcgcauccua gacccuuuct t                                              21

<210> SEQ ID NO 229
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 229 gaaaggucu aggaugcgct t                                               21

<210> SEQ ID NO 230
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 230
uuucgccuua gcgcccacut t                                              21
```

```
<210> SEQ ID NO 231
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 231
agugggcgcu aaggcgaaat t                                              21

<210> SEQ ID NO 232
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 232
cugguaccag aucgcgccct t                                              21

<210> SEQ ID NO 233
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 233
gggcgcgauc ugguaccagt t                                              21

<210> SEQ ID NO 234
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 234
cagaucgcgc ccaucuaggt t                                              21

<210> SEQ ID NO 235
```

```
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 235
ccuagauggg cgcgaucugt t                                              21

<210> SEQ ID NO 236
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 236
uccuaccuuu ugccgggagt t                                              21

<210> SEQ ID NO 237
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 237 cuccccggcaa aagguaggat t                                             21

<210> SEQ ID NO 238
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 238
cccuguucgc gcucucggct t                                              21

<210> SEQ ID NO 239
<211> LENGTH: 21
<212> TYPE: DNA
<213> ORGANISM: Artificial sequence
```

```
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 239
gccgagagcg cgaacagggt t                                            21

<210> SEQ ID NO 240
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 240
ccuguucgcg cucucggcat t                                            21

<210> SEQ ID NO 241
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 241
ugccgagagc gcgaacaggt t                                            21

<210> SEQ ID NO 242
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 242
cuguucgcgc ucucggcagt t                                            21

<210> SEQ ID NO 243
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
```

```
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 243
cugccgagag cgcgaacagt t                                              21

<210> SEQ ID NO 244
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 244
aagacuaucg acauggagct t                                              21

<210> SEQ ID NO 245
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 245
gcuccauguc gauagucuut t                                              21

<210> SEQ ID NO 246
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 246
cccgcgugcu aaugguggat t                                              21

<210> SEQ ID NO 247
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
```

<221> NAME/KEY: modified_base
<222> LOCATION: 1..19
<223> OTHER INFORMATION: /mod_base = "2'-hydroxy corresponding base"

<400> SEQUENCE: 247
uccaccauua gcacgcgggt t						21

<210> SEQ ID NO 248
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 248
cgugcuaaug guggaaacct t						21

<210> SEQ ID NO 249
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 249
gguuuccacc auuagcacgt t						21

<210> SEQ ID NO 250
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 250
ccggaguugu gcggcagugt t						21

<210> SEQ ID NO 251
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 251
cacugccgca caacuccggt t        21

<210> SEQ ID NO 252
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 252
gcuuucgccu uagcgcccat t        21

<210> SEQ ID NO 253
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 253
ugggcgcuaa ggcgaaagct t        21

<210> SEQ ID NO 254
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 254
agggauaaca cacugcaagt t        21

<210> SEQ ID NO 255
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 255
cuugcagugu guuaucccut t         21

<210> SEQ ID NO 256
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 256
caucaacggg uucacuacct t         21

<210> SEQ ID NO 257
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 257
gguagugaac ccguugaugt t         21

<210> SEQ ID NO 258
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 258
uuuaaggaca cccgugccct t         21

<210> SEQ ID NO 259
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 259
gggcacgggu guccuuaaat t         21

```
<210> SEQ ID NO 260
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 260
gacuuuuccg uugccgcugt t                                           21

<210> SEQ ID NO 261
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 261
cagcggcaac ggaaaaguct t                                           21

<210> SEQ ID NO 262
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 262
uuuuccguug ccgcugggat t                                           21

<210> SEQ ID NO 263
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 263
ucccagcggc aacggaaaat t                                           21

<210> SEQ ID NO 264
<211> LENGTH: 21
<212> TYPE: DNA
```

<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 264
gggaccucuu ggcgcgacgt t                                              21

<210> SEQ ID NO 265
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 265
cgucgcgcca agagguccct t                                              21

<210> SEQ ID NO 266
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 266
ggaccucuug gcgcgacgct t                                              21

<210> SEQ ID NO 267
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 267
gcgucgcgcc aagagguccu t                                              21

<210> SEQ ID NO 268
<211> LENGTH: 21
<212> TYPE: DNA
<213> ORGANISM: Artificial sequence
<220> FEATURE:
<223> OTHER INFORMATION: Additional RNAi agents targeting hTGF-beta

```
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 268
gaccucuugg cgcgacgcut t                                              21

<210> SEQ ID NO 269
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 269
agcgucgcgc caagagguct t                                              21

<210> SEQ ID NO 270
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 270
ccuacacggc gucccucagt t                                              21

<210> SEQ ID NO 271
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 271
cugagggacg ccguguaggt t                                              21

<210> SEQ ID NO 272
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
```

```
<220> FEATURE:
<221> NAME/KEY: modified_base
<222> LOCATION: 1..19
<223> OTHER INFORMATION: /mod_base = "2'-hydroxy corresponding base"

<400> SEQUENCE: 272
cgcgcauccu agacccuuut t                                              21

<210> SEQ ID NO 273
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 273
aaagggucua ggaugcgcgt t                                              21

<210> SEQ ID NO 274
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 274
cauccuagac ccuuucucct t                                              21

<210> SEQ ID NO 275
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 275
ggagaaaggg ucuaggaugt t                                              21

<210> SEQ ID NO 276
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
```

```
<223> OTHER INFORMATION: /mod_base = "2'-hydroxy corresponding base"

<400> SEQUENCE: 276
ugguaccaga ucgcgcccat t                                              21

<210> SEQ ID NO 277
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 277
ugggcgcgau cugguaccat t                                              21

<210> SEQ ID NO 278
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 278
uaccagaucg cgcccaucut t                                              21

<210> SEQ ID NO 279
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 279 agauggg cgc gaucugguat t                                             21

<210> SEQ ID NO 280
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 280
```
agaucgcgcc caucuaggut t                                    21

<210> SEQ ID NO 281
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 281
accuagaugg gcgcgaucut t                                    21

<210> SEQ ID NO 282
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 282
gcccaucuag guuauuucct t                                    21

<210> SEQ ID NO 283
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 283
ggaaauaacc uagaugggct t                                    21

<210> SEQ ID NO 284
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 284
cuaccuuuug ccgggagact t                                    21

```
<210> SEQ ID NO 285
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 285
gucucccggc aaaagguagt t                                              21

<210> SEQ ID NO 286
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 286
guucgcgcuc ucggcagugt t                                              21

<210> SEQ ID NO 287
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 287
cacugccgag agcgcgaact t                                              21

<210> SEQ ID NO 288
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 288
uucgcgcucu cggcagugct t                                              21

<210> SEQ ID NO 289
<211> LENGTH: 21
```

```
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 289
gcacugccga gagcgcgaat t                                              21

<210> SEQ ID NO 290
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 290
accugcaaga cuaucgacat t                                              21

<210> SEQ ID NO 291
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 291
ugucgauagu cuugcaggut t                                              21

<210> SEQ ID NO 292
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 292
cugcaagacu aucgacaugt t                                              21

<210> SEQ ID NO 293
<211> LENGTH: 21
<212> TYPE: DNA
<213> ORGANISM: Artificial sequence
<220> FEATURE:
```

<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 293 cagucgaua gucuugcagt t                                          21

<210> SEQ ID NO 294
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 294
gcaagacuau cgacauggat t                                         21

<210> SEQ ID NO 295
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 295
uccaugucga uagucuugct t                                         21

<210> SEQ ID NO 296
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 296
caagacuauc gacauggagt t                                         21

<210> SEQ ID NO 297
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.

-continued

```
    base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 297
cuccaugucg auagucuugt t                                              21

<210> SEQ ID NO 298
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
    base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 298
uguacaacag cacccgcgat t                                              21

<210> SEQ ID NO 299
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
    base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 299
ucgcgggugc uguuguacat t                                              21

<210> SEQ ID NO 300
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
    base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 300
ugaggccgac uacuacgcct t                                              21

<210> SEQ ID NO 301
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
    base + sugar but lacking 5'-phosphate
<220> FEATURE:
<221> NAME/KEY: modified_base
```

```
<222> LOCATION: 1..19
<223> OTHER INFORMATION: /mod_base = "2'-hydroxy corresponding base"

<400> SEQUENCE: 301
ggcguaguag ucggccucat t                                              21

<210> SEQ ID NO 302
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 302
aaacccacaa cgaaaucuat t                                              21

<210> SEQ ID NO 303
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 303
uagauuucgu uguggguuut t                                              21

<210> SEQ ID NO 304
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 304
ccacaacgaa aucuaugact t                                              21

<210> SEQ ID NO 305
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"
```

```
<400> SEQUENCE: 305
gucauagauu ucguuguggt t                                              21

<210> SEQ ID NO 306
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 306
aguacacaca gcauauauat t                                              21

<210> SEQ ID NO 307
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 307
uauauaugcu guguguacut t                                              21

<210> SEQ ID NO 308
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 308
cgguaccuga acccguguut t                                              21

<210> SEQ ID NO 309
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 309
aacacggguu cagguaccgt t                                              21
```

<210> SEQ ID NO 310
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
       base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 310
uaccugaacc cguguugcut t                                              21

<210> SEQ ID NO 311
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
       base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 311
agcaacacgg guucagguat t                                              21

<210> SEQ ID NO 312
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
       base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 312
cccguguugc ucucccgggt t                                              21

<210> SEQ ID NO 313
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
       base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 313
cccgggagag caacacgggt t                                              21

<210> SEQ ID NO 314

<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 314
cugcgucugc ugaggcucat t                                              21

<210> SEQ ID NO 315
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 315
ugagccucag cagacgcagt t                                              21

<210> SEQ ID NO 316
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 316
aggcucaagu uaaaaguggt t                                              21

<210> SEQ ID NO 317
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 317
ccacuuuuaa cuugagccut t                                              21

<210> SEQ ID NO 318
<211> LENGTH: 21
<212> TYPE: DNA
<213> ORGANISM: Artificial sequence

```
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 318 caacaauuccc uggcgauact t                                              21

<210> SEQ ID NO 319
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 319
guaucgccag gaauuguugt t                                               21

<210> SEQ ID NO 320
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 320
aacaauuccu ggcgauacct t                                               21

<210> SEQ ID NO 321
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 321
gguaucgcca ggaauuguut t                                               21

<210> SEQ ID NO 322
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
```

```
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 322
uggcgauacc ucagcaacct t                                              21

<210> SEQ ID NO 323
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 323
gguugcugag guaucgccat t                                              21

<210> SEQ ID NO 324
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 324
cgauaccuca gcaaccggct t                                              21

<210> SEQ ID NO 325
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 325
gccgguugcu gagguaucgt t                                              21

<210> SEQ ID NO 326
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
```

<221> NAME/KEY: modified_base
<222> LOCATION: 1..19
<223> OTHER INFORMATION: /mod_base = "2'-hydroxy corresponding base"

<400> SEQUENCE: 326
gauaccucag caaccggcut t                                                    21

<210> SEQ ID NO 327
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 327
agccgguugc ugagguauct t                                                    21

<210> SEQ ID NO 328
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 328
cuggcaccca gcgacucgct t                                                    21

<210> SEQ ID NO 329
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 329
gcgagucgcu gggugccagt t                                                    21

<210> SEQ ID NO 330
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 330
gacucgccag agugguuaut t                                              21

<210> SEQ ID NO 331
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 331
auaaccacuc uggcgaguct t                                              21

<210> SEQ ID NO 332
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 332
acucgccaga gugguuauct t                                              21

<210> SEQ ID NO 333
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 333
gauaaccacu cuggcgagut t                                              21

<210> SEQ ID NO 334
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 334

-continued

```
ugucaccgga guugugcggt t                                              21

<210> SEQ ID NO 335
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 335
ccgcacaacu ccggugacat t                                              21

<210> SEQ ID NO 336
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 336
caccggaguu gugcggcagt t                                              21

<210> SEQ ID NO 337
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 337
cugccgcaca acuccggugt t                                              21

<210> SEQ ID NO 338
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 338
accggaguug ugcggcagut t                                              21
```

```
<210> SEQ ID NO 339
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 339
acugccgcac aacuccggut t                                          21

<210> SEQ ID NO 340
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 340
aaauugaggg cuuucgccut t                                          21

<210> SEQ ID NO 341
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 341
aggcgaaagc ccucaauuut t                                          21

<210> SEQ ID NO 342
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 342
uugagggcuu ucgccuuagt t                                          21

<210> SEQ ID NO 343
<211> LENGTH: 21
<212> TYPE: DNA
```

```
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 343
cuaaggcgaa agcccucaat t                                              21

<210> SEQ ID NO 344
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 344
gggcuuucgc cuuagcgcct t                                              21

<210> SEQ ID NO 345
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 345
ggcgcuaagg cgaaagccct t                                              21

<210> SEQ ID NO 346
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 346
ccuuagcgcc cacugcucct t                                              21

<210> SEQ ID NO 347
<211> LENGTH: 21
<212> TYPE: DNA
<213> ORGANISM: Artificial sequence
<220> FEATURE:
<223> OTHER INFORMATION: Additional RNAi agents targeting hTGF-beta
```

```
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 347
ggagcagugg gcgcuaaggt t                                              21

<210> SEQ ID NO 348
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 348
aaguggacau caacgggutt t                                              21

<210> SEQ ID NO 349
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 349
aacccguuga uguccacuut t                                              21

<210> SEQ ID NO 350
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 350
caacggguuc acuaccggct t                                              21

<210> SEQ ID NO 351
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
```

```
<220> FEATURE:
<221> NAME/KEY: modified_base
<222> LOCATION: 1..19
<223> OTHER INFORMATION: /mod_base = "2'-hydroxy corresponding base"

<400> SEQUENCE: 351
gccgguagug aacccguugt t                                              21

<210> SEQ ID NO 352
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 352
cuaccggccg ccgaggugat t                                              21

<210> SEQ ID NO 353
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 353
ucaccucggc ggccgguagt t                                              21

<210> SEQ ID NO 354
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 354
caucugcaaa gcucccggct t                                              21

<210> SEQ ID NO 355
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
```

```
<223> OTHER INFORMATION: /mod_base = "2'-hydroxy corresponding base"

<400> SEQUENCE: 355
gccgggagcu uugcagaugt t                                              21

<210> SEQ ID NO 356
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 356
cguguacuac gugggccgct t                                              21

<210> SEQ ID NO 357
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 357
gcggcccacg uaguacacgt t                                              21

<210> SEQ ID NO 358
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 358
caacaugauc gugcgcucct t                                              21

<210> SEQ ID NO 359
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 359
```

```
ggagcgcacg aucauguugt t                                          21

<210> SEQ ID NO 360
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 360
cugugucauu gggcgccugt t                                          21

<210> SEQ ID NO 361
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 361
caggcgccca augacacagt t                                          21

<210> SEQ ID NO 362
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 362
ugccugucug cacuauucct t                                          21

<210> SEQ ID NO 363
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 363
ggaauagugc agacaggcat t                                          21
```

```
<210> SEQ ID NO 364
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 364
cacuauuccu uugcccggct t                                              21

<210> SEQ ID NO 365
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 365
gccgggcaaa ggaauagugt t                                              21

<210> SEQ ID NO 366
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 366
aacacuacug uaguuagaut t                                              21

<210> SEQ ID NO 367
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 367
aucuaacuac aguaguguut t                                              21

<210> SEQ ID NO 368
<211> LENGTH: 21
```

```
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 368
acacuacugu aguuagauct t                                              21

<210> SEQ ID NO 369
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 369
gaucuaacua caguagugut t                                              21

<210> SEQ ID NO 370
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 370
gucugagacg agccgccgct t                                              21

<210> SEQ ID NO 371
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 371
gcggcggcuc gucucagact t                                              21

<210> SEQ ID NO 372
<211> LENGTH: 21
<212> TYPE: DNA
<213> ORGANISM: Artificial sequence
<220> FEATURE:
```

```
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 372
cccuacacgg cgucccucat t                                              21

<210> SEQ ID NO 373
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 373
ugagggacgc cguguagggt t                                              21

<210> SEQ ID NO 374
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 374
acggaucucu cuccgaccut t                                              21

<210> SEQ ID NO 375
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 375
aggucggaga gagauccgut t                                              21

<210> SEQ ID NO 376
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
```

-continued base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 376
ggccggccgc gggacuauct t                                              21

<210> SEQ ID NO 377
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
    base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 377
gauagucccg cggccggcct t                                              21

<210> SEQ ID NO 378
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
    base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 378
cgcggccaga uccuguccat t                                              21

<210> SEQ ID NO 379
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
    base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 379
uggacaggau cuggccgcgt t                                              21

<210> SEQ ID NO 380
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
    base + sugar but lacking 5'-phosphate
<220> FEATURE:
<221> NAME/KEY: modified_base

```
<222> LOCATION: 1..19
<223> OTHER INFORMATION: /mod_base = "2'-hydroxy corresponding base"

<400> SEQUENCE: 380
ggaaacccac aacgaaauct t                                              21

<210> SEQ ID NO 381
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 381
gauuucguug uggguuucct t                                              21

<210> SEQ ID NO 382
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 382
acaauuccug gcgauaccut t                                              21

<210> SEQ ID NO 383
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 383
agguaucgcc aggaauugut t                                              21

<210> SEQ ID NO 384
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"
```

```
<400> SEQUENCE: 384
agucugagac gagccgccgt t                                           21

<210> SEQ ID NO 385
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 385
cggcggcucg ucucagacut t                                           21

<210> SEQ ID NO 386
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 386
cacggcgucc cucaggcgct t                                           21

<210> SEQ ID NO 387
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 387
gcgccugagg gacgccgugt t                                           21

<210> SEQ ID NO 388
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 388
acggcguccc ucaggcgcct t                                           21
```

<210> SEQ ID NO 389
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 389
ggcgccugag ggacgccgut t                                             21

<210> SEQ ID NO 390
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 390
accagcccuc gggagucgct t                                             21

<210> SEQ ID NO 391
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 391
gcgacucccg agggcuggut t                                             21

<210> SEQ ID NO 392
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 392
gcauccuaga cccuuucuct t                                             21

<210> SEQ ID NO 393

```
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 393
gagaaagggu cuaggaugct t                                              21

<210> SEQ ID NO 394
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 394
gacggaucuc ucuccgacct t                                              21

<210> SEQ ID NO 395
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 395
ggucggagag agauccguct t                                              21

<210> SEQ ID NO 396
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 396
gguaccagau cgcgcccaut t                                              21

<210> SEQ ID NO 397
<211> LENGTH: 21
<212> TYPE: DNA
<213> ORGANISM: Artificial sequence
```

```
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 397
augggcgcga ucugguacct t                                                 21

<210> SEQ ID NO 398
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 398
uagguuauuu ccgugggaut t                                                 21

<210> SEQ ID NO 399
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 399
aucccacgga aauaaccuat t                                                 21

<210> SEQ ID NO 400
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 400
accuuuugcc gggagaccct t                                                 21

<210> SEQ ID NO 401
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
```

<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 401
gggucucccg gcaaaaggut t                                               21

<210> SEQ ID NO 402
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 402
ucgcgcucuc ggcagugcct t                                               21

<210> SEQ ID NO 403
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 403
ggcacugccg agagcgcgat t                                               21

<210> SEQ ID NO 404
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 404
uauccaccug caagacuaut t                                               21

<210> SEQ ID NO 405
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:

```
<221> NAME/KEY: modified_base
<222> LOCATION: 1..19
<223> OTHER INFORMATION: /mod_base = "2'-hydroxy corresponding base"

<400> SEQUENCE: 405
auagucuugc agguggauau t                                              21

<210> SEQ ID NO 406
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 406
ccgcggccag auccugucct t                                              21

<210> SEQ ID NO 407
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 407
ggacaggauc uggccgcggt t                                              21

<210> SEQ ID NO 408
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 408
aacccacaac gaaaucuaut t                                              21

<210> SEQ ID NO 409
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"
```

-continued

<400> SEQUENCE: 409
auagauuucg uugugguut t                                                21

<210> SEQ ID NO 410
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 410
agcgguaccu gaacccgugt t                                               21

<210> SEQ ID NO 411
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 411
cacgggurca gguaccgcut t                                               21

<210> SEQ ID NO 412
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 412
uggcacccag cgacucgcct t                                               21

<210> SEQ ID NO 413
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 413
ggcgagucgc ugggugccat t                                                    21

<210> SEQ ID NO 414
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 414
cucgccagag ugguuaucut t                                                    21

<210> SEQ ID NO 415
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 415
agauaaccac ucuggcgagt t                                                    21

<210> SEQ ID NO 416
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 416
cggcaguggu ugagccgugt t                                                    21

<210> SEQ ID NO 417
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 417
cacggcucaa ccacugccgt t                                                    21

```
<210> SEQ ID NO 418
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 418
gugguugagc cguggagggt t                                              21

<210> SEQ ID NO 419
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 419
cccuccacgg cucaaccact t                                              21

<210> SEQ ID NO 420
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 420
gagggcuuuc gccuuagcgt t                                              21

<210> SEQ ID NO 421
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 421
cgcuaaggcg aaagcccuct t                                              21

<210> SEQ ID NO 422
<211> LENGTH: 21
<212> TYPE: DNA
```

```
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 422
agggcuuucg ccuuagcgct t                                              21

<210> SEQ ID NO 423
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 423
gcgcuaaggc gaaagcccut t                                              21

<210> SEQ ID NO 424
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 424
ggugaccugg ccaccauuct t                                              21

<210> SEQ ID NO 425
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 425
gaaugguggc caggucacct t                                              21

<210> SEQ ID NO 426
<211> LENGTH: 21
<212> TYPE: DNA
<213> ORGANISM: Artificial sequence
<220> FEATURE:
<223> OTHER INFORMATION: Additional RNAi agents targeting hTGF-beta
```

```
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 426
accauucaug gcaugaacct t                                              21

<210> SEQ ID NO 427
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 427
gguucaugcc augaauggut t                                              21

<210> SEQ ID NO 428
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 428
cauggcauga accggccuut t                                              21

<210> SEQ ID NO 429
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 429
aaggccgguu caugccaugt t                                              21

<210> SEQ ID NO 430
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
```

-continued

```
<220> FEATURE:
<221> NAME/KEY: modified_base
<222> LOCATION: 1..19
<223> OTHER INFORMATION: /mod_base = "2'-hydroxy corresponding base"

<400> SEQUENCE: 430
ccaacuauug cuucagcuct t                                              21

<210> SEQ ID NO 431
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 431
gagcugaagc aauaguuggt t                                              21

<210> SEQ ID NO 432
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 432
gaacugcugc gugcggcagt t                                              21

<210> SEQ ID NO 433
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 433
cugccgcacg cagcaguuct t                                              21

<210> SEQ ID NO 434
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
```

```
<223> OTHER INFORMATION: /mod_base = "2'-hydroxy corresponding base"

<400> SEQUENCE: 434
gcccuguaca accagcauat t                                              21

<210> SEQ ID NO 435
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 435
uaugcugguu guacagggct t                                              21

<210> SEQ ID NO 436
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 436
cuguacaacc agcauaacct t                                              21

<210> SEQ ID NO 437
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 437
gguuaugcug guuguacagt t                                              21

<210> SEQ ID NO 438
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 438
```

-continued guacaaccag cauaacccgt t                21

<210> SEQ ID NO 439
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 439 cgggduuaugc ugguuguact t                21

<210> SEQ ID NO 440
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 440
cuauuccuuu gcccggcaut t                21

<210> SEQ ID NO 441
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 441
augccgggca aaggaauagt t                21

<210> SEQ ID NO 442
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 442
agcggaggaa ggagucgcct t                21

<210> SEQ ID NO 443
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 443
ggcgacuccu uccuccgcut t                                              21

<210> SEQ ID NO 444
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 444
ggaggaagga gucgccgagt t                                              21

<210> SEQ ID NO 445
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 445
cucggcgacu ccuuccucct t                                              21

<210> SEQ ID NO 446
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 446 acuuugaga cuuuccgut t                                                21

<210> SEQ ID NO 447
<211> LENGTH: 21

```
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 447
acggaaaagu cucaaaagut t                                             21

<210> SEQ ID NO 448
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 448
uugagacuuu uccguugcct t                                             21

<210> SEQ ID NO 449
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 449
ggcaacggaa aagucucaat t                                             21

<210> SEQ ID NO 450
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 450
accucuuggc gcgacgcugt t                                             21

<210> SEQ ID NO 451
<211> LENGTH: 21
<212> TYPE: DNA
<213> ORGANISM: Artificial sequence
<220> FEATURE:
```

<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 451
cagcgucgcg ccaagaggut t                                          21

<210> SEQ ID NO 452
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 452
gacccggccu cccgcaaagt t                                          21

<210> SEQ ID NO 453
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 453
cuuugcggga ggccggguct t                                          21

<210> SEQ ID NO 454
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 454
cccggccucc cgcaaagact t                                          21

<210> SEQ ID NO 455
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.

-continued

```
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 455 gcuuugcgg gaggccgggt t                                              21

<210> SEQ ID NO 456
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 456
cuccuccagg agacggauct t                                             21

<210> SEQ ID NO 457
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 457
gauccgucuc cuggaggagt t                                             21

<210> SEQ ID NO 458
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 458
caccuucugg uaccagauct t                                             21

<210> SEQ ID NO 459
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
```

```
<222> LOCATION: 1..19
<223> OTHER INFORMATION: /mod_base = "2'-hydroxy corresponding base"

<400> SEQUENCE: 459 gaucuggua cagaaggugt t                                                    21

<210> SEQ ID NO 460
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 460
cuucugguac cagaucgcgt t                                                   21

<210> SEQ ID NO 461
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 461
cgcgaucugg uaccagaagt t                                                   21

<210> SEQ ID NO 462
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 462
uucugguacc agaucgcgct t                                                   21

<210> SEQ ID NO 463
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"
```

```
<400> SEQUENCE: 463
gcgcgaucug guaccagaat t                                              21

<210> SEQ ID NO 464
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 464
gguuauuucc gugggauact t                                              21

<210> SEQ ID NO 465
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 465
guaucccacg gaaauaacct t                                              21

<210> SEQ ID NO 466
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 466
accucagcuu ucccucgagt t                                              21

<210> SEQ ID NO 467
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 467
cucgagggaa agcugaggut t                                              21
```

<210> SEQ ID NO 468
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 468
ccucagcuuu cccucgaggt t                                             21

<210> SEQ ID NO 469
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 469
ccucgaggga aagcugaggt t                                             21

<210> SEQ ID NO 470
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 470
uaccuuuugc cgggagacct t                                             21

<210> SEQ ID NO 471
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 471
ggucucccgg caaaagguat t                                             21

<210> SEQ ID NO 472

```
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 472
ccaugccgcc cuccgggcut t                                              21

<210> SEQ ID NO 473
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 473
agcccggagg gcggcauggt t                                              21

<210> SEQ ID NO 474
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 474
acuauccacc ugcaagacut t                                              21

<210> SEQ ID NO 475
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 475
agucuugcag guggauagut t                                              21

<210> SEQ ID NO 476
<211> LENGTH: 21
<212> TYPE: DNA
<213> ORGANISM: Artificial sequence
```

-continued

```
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 476
cuauccaccu gcaagacuat t                                               21

<210> SEQ ID NO 477
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 477
uagucuugca gguggauagt t                                               21

<210> SEQ ID NO 478
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 478
guccaagcug cggcucgcct t                                               21

<210> SEQ ID NO 479
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 479
ggcgagccgc agcuuggact t                                               21

<210> SEQ ID NO 480
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
```

```
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 480
cgagccugag gccgacuact t                                              21

<210> SEQ ID NO 481
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 481
guagucggcc ucaggcucgt t                                              21

<210> SEQ ID NO 482
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 482
ugguggaaac ccacaacgat t                                              21

<210> SEQ ID NO 483
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 483
ucguuguggg uuuccaccat t                                              21

<210> SEQ ID NO 484
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
```

```
<221> NAME/KEY: modified_base
<222> LOCATION: 1..19
<223> OTHER INFORMATION: /mod_base = "2'-hydroxy corresponding base"

<400> SEQUENCE: 484
acccacaacg aaaucuaugt t                                              21

<210> SEQ ID NO 485
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 485
cauagauuuc guugugggut t                                              21

<210> SEQ ID NO 486
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 486
ucaagcagag uacacacagt t                                              21

<210> SEQ ID NO 487
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 487
cuguguguac ucugcuugat t                                              21

<210> SEQ ID NO 488
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"
```

-continued

<400> SEQUENCE: 488
cagaguacac acagcauaut t                                          21

<210> SEQ ID NO 489
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 489
auaugcugug uguacucugt t                                          21

<210> SEQ ID NO 490
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 490
ucuucaacac aucagagcut t                                          21

<210> SEQ ID NO 491
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 491
agcucugaug uguugaagat t                                          21

<210> SEQ ID NO 492
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 492
gcgguaccug aacccgugut t                    21

<210> SEQ ID NO 493
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 493
acacggguuc agguaccgct t                    21

<210> SEQ ID NO 494
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 494
cugcugaggc ucaaguuaat t                    21

<210> SEQ ID NO 495
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 495
uuaacuugag ccucagcagt t                    21

<210> SEQ ID NO 496
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 496
gcgauaccuc agcaaccggt t                    21

```
<210> SEQ ID NO 497
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 497
ccgguugcug agguaucgct t                                              21

<210> SEQ ID NO 498
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 498
ggcacccagc gacucgccat t                                              21

<210> SEQ ID NO 499
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 499
uggcgagucg cugggugcct t                                              21

<210> SEQ ID NO 500
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 500
ccagcgacuc gccagagugt t                                              21

<210> SEQ ID NO 501
<211> LENGTH: 21
<212> TYPE: DNA
```

```
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 501
cacucuggcg agucgcuggt t                                              21

<210> SEQ ID NO 502
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 502
gagugguuau cuuugaugt t                                               21

<210> SEQ ID NO 503
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 503
caucaaaaga uaaccacuct t                                              21

<210> SEQ ID NO 504
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 504
uugugcggca gugguugagt t                                              21

<210> SEQ ID NO 505
<211> LENGTH: 21
<212> TYPE: DNA
<213> ORGANISM: Artificial sequence
<220> FEATURE:
<223> OTHER INFORMATION: Additional RNAi agents targeting hTGF-beta
```

```
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 505
cucaaccacu gccgcacaat t                                              21

<210> SEQ ID NO 506
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 506
ugugacagca gggauaacat t                                              21

<210> SEQ ID NO 507
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 507
uguuaucccu gcugucacat t                                              21

<210> SEQ ID NO 508
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 508
acagcaggga uaacacacut t                                              21

<210> SEQ ID NO 509
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
```

```
<220> FEATURE:
<221> NAME/KEY: modified_base
<222> LOCATION: 1..19
<223> OTHER INFORMATION: /mod_base = "2'-hydroxy corresponding base"

<400> SEQUENCE: 509
aguguguuau cccugcugut t                                              21

<210> SEQ ID NO 510
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 510
cagcagggau aacacacugt t                                              21

<210> SEQ ID NO 511
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 511
caguguguua ucccugcugt t                                              21

<210> SEQ ID NO 512
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 512
uaacacacug caaguggact t                                              21

<210> SEQ ID NO 513
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
```

-continued

```
<223> OTHER INFORMATION: /mod_base = "2'-hydroxy corresponding base"

<400> SEQUENCE: 513
guccacuugc aguguguuat t                                              21

<210> SEQ ID NO 514
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 514
guucacuacc ggccgccgat t                                              21

<210> SEQ ID NO 515
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 515
ucggcggccg guagugaact t                                              21

<210> SEQ ID NO 516
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 516
uggccaccau ucauggcaut t                                              21

<210> SEQ ID NO 517
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 517
```
augccaugaa ugguggccat t                           21

<210> SEQ ID NO 518
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 518
cauucauggc augaaccggt t                           21

<210> SEQ ID NO 519
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 519
ccgguucaug ccaugaaugt t                           21

<210> SEQ ID NO 520
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 520
cagcaucugc aaagcuccct t                           21

<210> SEQ ID NO 521
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 521
gggagcuuug cagaugcugt t                           21

<210> SEQ ID NO 522
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 522
gcaaagcucc cggcaccgct t                                              21

<210> SEQ ID NO 523
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 523
gcggugccgg gagcuuugct t                                              21

<210> SEQ ID NO 524
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 524
ggagaagaac ugcugcgugt t                                              21

<210> SEQ ID NO 525
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 525
cacgcagcag uucuucucct t                                              21

<210> SEQ ID NO 526
<211> LENGTH: 21

```
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 526
gaagaacugc ugcgugcggt t                                              21

<210> SEQ ID NO 527
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 527
ccgcacgcag caguucuuct t                                              21

<210> SEQ ID NO 528
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 528
gcuggaagug gauccacgat t                                              21

<210> SEQ ID NO 529
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 529
ucguggaucc acuuccagct t                                              21

<210> SEQ ID NO 530
<211> LENGTH: 21
<212> TYPE: DNA
<213> ORGANISM: Artificial sequence
<220> FEATURE:
```

-continued

<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 530
uuuggagccu ggacacgcat t                                              21

<210> SEQ ID NO 531
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 531
ugcgugucca ggcuccaaat t                                              21

<210> SEQ ID NO 532
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 532
uuggagccug gacacgcagt t                                              21

<210> SEQ ID NO 533
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 533
cugcgugucc aggcuccaat t                                              21

<210> SEQ ID NO 534
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.

-continued

```
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 534
gccgugcugc gugccgcagt t                                              21

<210> SEQ ID NO 535
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 535
cugcggcacg cagcacggct t                                              21

<210> SEQ ID NO 536
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 536
uguccaacau gaucgugcgt t                                              21

<210> SEQ ID NO 537
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 537
cgcacgauca uguuggacat t                                              21

<210> SEQ ID NO 538
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
```

<222> LOCATION: 1..19
<223> OTHER INFORMATION: /mod_base = "2'-hydroxy corresponding base"

<400> SEQUENCE: 538
cugcggaucu cugugucaut t                                              21

<210> SEQ ID NO 539
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 539
augacacaga gauccgcagt t                                              21

<210> SEQ ID NO 540
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 540
gcacuauucc uuugcccggt t                                              21

<210> SEQ ID NO 541
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 541
ccgggcaaag gaauagugct t                                              21

<210> SEQ ID NO 542
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

-continued

```
<400> SEQUENCE: 542
ccggccuccc gcaaagacut t                                              21

<210> SEQ ID NO 543
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 543
agucuuugcg ggaggccggt t                                              21

<210> SEQ ID NO 544
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 544
cuacuggugc ugacgccugt t                                              21

<210> SEQ ID NO 545
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 545
caggcgucag caccaguagt t                                              21

<210> SEQ ID NO 546
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 546
auucauggca ugaaccggct t                                              21
```

<210> SEQ ID NO 547
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 547
gccgguucau gccaugaaut t                                              21

<210> SEQ ID NO 548
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 548
aacugcugcg ugcggcagct t                                              21

<210> SEQ ID NO 549
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 549
gcugccgcac gcagcaguut t                                              21

<210> SEQ ID NO 550
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 550
cggaggaagg agucgccgat t                                              21

<210> SEQ ID NO 551

```
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 551
ucggcgacuc cuuccuccgt t                                          21

<210> SEQ ID NO 552
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 552
ggagcgggag gagggacgat t                                          21

<210> SEQ ID NO 553
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 553
ucgucccucc ucccgcucct t                                          21

<210> SEQ ID NO 554
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 554
gcccucggga gucgccgact t                                          21

<210> SEQ ID NO 555
<211> LENGTH: 21
<212> TYPE: DNA
<213> ORGANISM: Artificial sequence
```

```
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 555
gucggcgacu cccgagggct t                                              21

<210> SEQ ID NO 556
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 556
uuucuccucc aggagacggt t                                              21

<210> SEQ ID NO 557
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 557
ccgucuccug gaggagaaat t                                              21

<210> SEQ ID NO 558
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 558
ucgaggcccu ccuaccuuut t                                              21

<210> SEQ ID NO 559
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
```

```
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 559
aaagguagga gggccucgat t                                              21

<210> SEQ ID NO 560
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 560
uacuggugcu gacgccuggt t                                              21

<210> SEQ ID NO 561
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 561
ccaggcguca gcaccaguat t                                              21

<210> SEQ ID NO 562
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 562
gacuauccac cugcaagact t                                              21

<210> SEQ ID NO 563
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
```

<221> NAME/KEY: modified_base
<222> LOCATION: 1..19
<223> OTHER INFORMATION: /mod_base = "2'-hydroxy corresponding base"

<400> SEQUENCE: 563
gucuugcagg uggauaguct t                                              21

<210> SEQ ID NO 564
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 564
uacaacagca cccgcgacct t                                              21

<210> SEQ ID NO 565
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 565
ggucgcgggu gcuguuguat t                                              21

<210> SEQ ID NO 566
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 566
ugcugaggcu caaguuaaat t                                              21

<210> SEQ ID NO 567
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

-continued

<400> SEQUENCE: 567
uuuaacuuga gccucagcat t                                              21

<210> SEQ ID NO 568
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 568
ccugugacag cagggauaat t                                              21

<210> SEQ ID NO 569
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 569
uuaucccugc ugucacaggt t                                              21

<210> SEQ ID NO 570
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 570
auaacacacu gcaaguggat t                                              21

<210> SEQ ID NO 571
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 571

```
uccacuugca guguguuaut t                                              21

<210> SEQ ID NO 572
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 572
uauugcuuca gcuccacggt t                                              21

<210> SEQ ID NO 573
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 573
ccguggagcu gaagcaauat t                                              21

<210> SEQ ID NO 574
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 574
gcuguccaac augaucgugt t                                              21

<210> SEQ ID NO 575
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 575
cacgaucaug uuggacagct t                                              21
```

```
-continued
<210> SEQ ID NO 576
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 576
gucuccaucc cugacguuct t                                                 21

<210> SEQ ID NO 577
<211> LENGTH: 21
<212> TYPE: DNA
<213> ORGANISM: Artificial sequence
<220> FEATURE:
<223> OTHER INFORMATION: Additional RNAi agents targeting hTGF-beta
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 577
gaacgucagg gauggagact t                                                 21
```

RNAI MODULATION OF TGF-BETA AND THERAPEUTIC USES THEREOF

CROSS-REFERENCE TO RELATED APPLICATION

This application claims the benefit of U.S. Provisional Application No. 60/782,829, filed Mar. 16, 2006, which is hereby incorporated by reference in its entirety.

TECHNICAL FIELD

The present invention concerns methods of treatment using transforming growth factor beta (TGF-beta) modulators. More specifically, the invention concerns methods of treating disorders associated with undesirable TGF-beta signaling, by administering short interfering RNA which down-regulate the expression of TGF-beta, and agents useful therein.

BACKGROUND

RNA interference or "RNAi" is a term initially coined by Fire and co-workers to describe the observation that double-stranded RNA (dsRNA) can block gene expression when it is introduced into worms (Fire et al., Nature 391:806-811, 1998). Short dsRNA directs gene-specific, post-transcriptional silencing in many organisms, including vertebrates, and has provided a new tool for studying gene function. RNAi has been suggested as a method of developing a new class of therapeutic agents. However, to date, these have remained mostly as suggestions with no demonstrate proof that RNAi can be used therapeutically.

Transforming growth factor-beta (TGF-beta) isoforms (−1, −2, & −3) are potent cytokines that act in autocrine and paracrine fashion to effect a broad spectrum of biological processes, including proliferation, differentiation, apoptosis, and extracellular matrix production. TGF-beta exerts its biological effects via binding to TGF-beta receptors (types I, II, & III). The local over-expression of TGF-beta in the kidney, liver, or lung mediates the pathophysiology observed in diabetic nephropathy, chronic liver disease, and pulmonary fibrosis, respectively. TGF-beta1 is up-regulated in patients with diabetic nephropathy (for both type 1 or type 2 diabetes) and in animal models of the disease. Antibodies to TGF-beta have been shown to prevent disease in a mouse genetic model of type 2 diabetes (db/db mouse) and antisense targeting a conserved sequence in TGF-beta RNA has been shown to prevent disease in a streptozotocin-diabetic mouse model.

About 100,000 diabetic patients per year are treated for kidney disease in U.S. with health costs of $5.1 billion per year in the U.S. Diabetic nephropathy is the leading cause of end-stage renal disease in the industrialized world. Almost 40% of all new patients with renal failure admitted to renal replacement programs in the U.S have diabetic kidney disease. Albuminuria, proteinuria, serum creatinine, as well as circulating TGF-beta1 plasma levels, can be used as markers for efficacy determination in therapeutic evaluation.

Liver disease affects all age groups and both genders. The condition can be acute or chronic. The major causes of liver diseases in the United States are viruses (hepatitis A, B, C) and alcohol abuse. However, congenital, autoimmune and drug-induced causes are also significant contributors to the origin of liver diseases. Liver diseases disturb hepatic functions as a result of destruction of functional liver tissue and development of fibrosis (scarring), which blocks blood flow through the liver and causes portal hypertension (pressure in the portal vein). Blood flow then seeks an alternative route, leading to dilated swollen veins (varices) in the esophagus that may hemorrhage. Liver disease and portal hypertension also alter kidney function by causing retention of salt and water (ascites), and can induce renal failure (hepatorenal syndrome) and altered mental state (coma). The primary cytokine involved in tissue scaring in chronic liver disease is TGF-beta1. Recently it has been shown in a rat model of liver fibrosis that blocking TGF-beta1 can lead to improvement in liver histology. Further, in chronic Hepatitis C patients who have responded to interferon alpha, decreased levels of TGF-beta1 are associated with improvements in liver fibrosis.

TGF-beta1 has also been implicated in Idiopathic Pulmonary Fibrosis. Similar to liver disease, the mechanisms of action of TGF-beta1 in pulmonary fibrosis involves both induction and inhibition of the degradation of extracellular matrix proteins, leading to the formation of scar tissue. TGF-beta1 mediated cell signaling, primarily at the local site of connective tissue, is anabolic and leads to pulmonary fibrosis and angiogenesis, strongly indicating that TGF-beta1 may be involved in the repair of tissue injury caused by burns, trauma, or surgery. Pulmonary fibrosis, also called Interstitial Lung Disease (ILD), is a broad category of lung diseases that includes more than 130 disorders which are characterized by scarring of the lungs. ILD accounts for 15% of the cases seen by pulmonologists. Some of the interstitial lung disorders include: Idiopathic pulmonary fibrosis, Hypersensitivity pneumonitis, Sarcoidosis, Eosinophilic granuloma, Wegener's granulomatosis, Idiopathic pulmonary hemosiderosis, and Bronchiolitis obliterans. In ILD, scarring or fibrosis occurs as a result of either an injury or an autoimmune process. Approximately 70% of ILD have no identifiable cause and are therefore termed "idiopathic pulmonary fibrosis." Some of the known causes include occupational and environmental exposure, dust (silica, hard metal dusts), organic dust (bacteria, animal proteins), gases and fumes, drugs, poisons, chemotherapy medications, radiation therapy, infections, connective tissue disease, systemic lupus erythematosus, and rheumatoid arthritis. In its severest form, ILD can lead to death, which is often caused by respiratory failure due to hypoxemia, right-heart failure, heart attack, stroke, blood clot (embolism) in the lungs, or lung infection brought on by the disease.

The use of small interfering nucleic acid molecules targeting transforming growth factor beta (TGF-beta) genes provides a class of novel therapeutic agents that can be used in the treatment of various diseases and conditions associated with undesired TGF-beta signaling, including diabetic nephropathy, chronic liver disease, pulmonary fibrosis, hematopoietic reconstitution, and any other inflammatory, respiratory, autoimmune, and/or proliferative disease, condition, or trait that responds to the level of TGF-beta in a cell, subject or organism, and particularly idiopathic pulmonary fibrosis.

SUMMARY

The present invention is based on the in vitro demonstration that TGF-beta expression can be inhibited by iRNA agents, and the identification of potent iRNA agents from the TGF-beta gene that can reduce RNA levels and protein levels of TGF-beta in cells, and particularly in an organism. Based on these findings, the present invention provides specific compositions and methods that are useful in reducing TGF-beta mRNA levels and TGF-beta protein levels in cells in vitro as well as in a subject in vivo, e.g., a mammal, such as a human. These compositions are particularly useful in the manufacturing of pharmaceutical compositions for the treatment of, and ultimately in methods to treat, subjects having or at risk of developing a disease or disorder associated with undesired TGF-beta signaling such as, for example, idiopathic pulmonary fibrosis.

The present invention specifically provides methods of reducing the levels of a TGF-beta mRNA in a cell of a subject, or of TGF-beta protein secreted by a cell of a subject, comprising the step of administering an iRNA agent to said subject, wherein the iRNA agent comprises an antisense strand consisting of 15 to 30 nucleotides and having at least 15 or more contiguous nucleotides complementary to a mammalian TGF-beta mRNA, and a sense strand consisting of 15 to 30 nucleotides and having at least 15 or more contiguous nucleotides complementary to said antisense strand. Said iRNA agent may mediate the cleavage of a TGF-beta mRNA within the target sequence of an iRNA agent selected from the group of: AL-DP-6837 to AL-DP-6864 and AD-14419 to AD-14638. In one embodiment, said iRNA agent comprises 15 or more contiguous nucleotides from an iRNA agent selected from the group of: AL-DP-6837 to AL-DP-6864, AL-DP-6140 to AL-DP-6151, AL-DP-6262 to AL-DP-6277 and AD-14419 to AD-14638. In a further embodiment, said iRNA agent is one of the iRNA agents selected from the group of: AL-DP-6837 to AL-DP-6864, AL-DP-6140 to AL-DP-6151, AL-DP-6262 to AL-DP-6277 and AD-14419 to AD-14638. In further embodiments, the iRNA agents mediates the cleavage of a TGF-beta mRNA within the target sequence of an iRNA agent, comprises 15 or more contiguous nucleotides from an iRNA agent, or is an iRNA agent, selected from one of the following groups: the 20%-group, the 30%-group, the 40%-group, the 50%-group, the 60%-group, the 70%-group, the 80%-group, or the 90%-group, as defined below. Said iRNA agent may be administered to a subject, wherein administration may comprise pulmonary administration. As a result of the inventive method, the level of TGF-beta protein and/or TGF-beta mRNA may be reduced by at least 20%.

In another aspect, the invention provides isolated iRNA agents, comprising an antisense strand consisting of 15 to 30 nucleotides and having at least 15 or more contiguous nucleotides complementary to a mammalian TGF-beta mRNA, and a sense strand consisting of 15 to 30 nucleotides and having at least 15 or more contiguous nucleotides complementary to said antisense strand. In one embodiment, said iRNA agent mediates the cleavage of a TGF-beta mRNA within the target sequence of an iRNA agent selected from one of the following groups: the group of AL-DP-6837 to AL-DP-6864 and AD-14419 to AD-14638, the 20%-group, the 30%-group, the 40%-group, the 50%-group, the 60%-group, the 70%-group, the 80%-group, or the 90%-group, as defined below. In a further embodiment, said iRNA agent comprises 15 or more contiguous nucleotides from an iRNA agent selected from one of the following groups: the group of AL-DP-6837 to AL-DP-6864, AL-DP-6140 to AL-DP-6151, AL-DP-6262 to AL-DP-6277 and AD-14419 to AD-14638 the 20%-group, the 30%-group, the 40%-group, the 50%-group, the 60%-group, the 70%-group, the 80%-group, or the 90%-group, as defined below. More specifically, said iRNA agent may be an iRNA agent selected from one of the following groups of: AL-DP-6837 to AL-DP-6864, AL-DP-6140 to AL-DP-6151, AL-DP-6262 to AL-DP-6277 and AD-14419 to AD-14638; the 20%-group, the 30%-group, the 40%-group, the 50%-group, the 60%-group, the 70%-group, the 80%-group, or the 90%-group, as defined below. The iRNA agent may further comprise a non-nucleotide moiety. Furthermore, the sense and/or antisense strand may be stabilized against nucleolytic degradation. The iRNA agent may further comprise at least one 3'-overhang, wherein said 3'-overhang comprises from 1 to 6 nucleotides. Also, the iRNA agent may comprise a phosphorothioate at the first internucleotide linkage at the 5' end of the antisense and/or sense sequence, and optionally a further phosphorothioate at the first internucleotide linkage at the 3' end of the antisense and/or sense sequence. The iRNA agent may comprise a 2'-modified nucleotide, preferably selected from the group consisting of: 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), and 2'-O—N-methylacetamido (2'-O—NMA).

In another aspect, the instant invention features a method of reducing the levels of a TGF-beta mRNA in a cell, or of TGF-beta protein secreted by a cell, comprising contacting the cell with an iRNA agent of the invention.

In yet another aspect, the instant invention provides a vector encoding an iRNA agent of the invention.

In yet another aspect, the instant invention provides a cell comprising an iRNA agent or a vector of the invention.

In yet another aspect, the a method of making an iRNA agent of the invention is provided, the method comprising the synthesis of the iRNA agent, wherein the sense and antisense strands comprise at least one modification that stabilizes the iRNA agent against nucleolytic degradation.

In yet another aspect, the instant invention provides a pharmaceutical composition comprising an iRNA agent of the invention and a pharmaceutically acceptable carrier.

In yet another aspect, the instant invention provides a method of treating a human diagnosed as having or at risk for developing a disease or disorder associated with undesired TGF-beta signaling, comprising administering to a subject in need of such treatment a therapeutically effective amount of an iRNA agent of the invention. In one embodiment, the human is diagnosed as having or at risk for having idiopathic pulmonary fibrosis, diabetic nephropathy or chronic liver disease.

Table 1 provides exemplary iRNA agents of the invention.

TABLE 1

Oligonucleotide sequences of siRNAs specific for TGF-beta

| Position of target sequence in NM_000660.3 | Duplex identifier | sense strand sequence[1] | SEQ ID NO: | antisense strand sequence[1] | SEQ ID NO: |
|---|---|---|---|---|---|
| 1186-1208 | AL-DP-6837 | ggucacccgcgugcuaaugTT | 1 | cauuagcacgcgggugaccTT | 2 |
| 1186-1208 | AL-DP-6140 | ggumcmacmcmcmgcmgumgcmumaaumgTT | 3 | cmauumagcmacgcgggugaccTT | 4 |
| 1184-1206 | AL-DP-6838 | gaggucacccgcgugcuaaTT | 5 | uuagcacgcgggugaccucTT | 6 |

TABLE 1-continued

Oligonucleotide sequences of siRNAs specific for TGF-beta

| Position of target sequence in NM_000660.3 | Duplex identifier | sense strand sequence[1] | SEQ ID NO: | antisense strand sequence[1] | SEQ ID NO: |
|---|---|---|---|---|---|
| 1184-1206 | AL-DP-6141 | gaggumcmacmcmcmgcmgumgcmumaaTT | 7 | uumagcmacgcgggugaccucTT | 8 |
| 1112-1134 | AL-DP-6839 | agcacccgcgaccggguggTT | 9 | ccacccggucgcgggugcuTT | 10 |
| 1112-1134 | AL-DP-6142 | agcmacmcmcmgcmgacmcmgggumggTT | 11 | ccmacccggucgcgggugcuTT | 12 |
| 1797-1819 | AL-DP-6840 | uccacgagcccaagggcuaTT | 13 | uagcccuugggcucguggaTT | 14 |
| 1797-1819 | AL-DP-6143 | umcmcmacmgagcmcmcmaagggcmumaTT | 15 | umagcccuugggcucguggaTT | 16 |
| 444-466 | AL-DP-6841 | auuccggaccagcccucggTT | 17 | ccgagggcugguccggaauTT | 18 |
| 444-466 | AL-DP-6144 | aumumcmcmggacmcmagcmcmcmumcmggTT | 19 | ccgagggcugguccggaauTT | 20 |
| 1185-1207 | AL-DP-6842 | aggucacccgcgugcuaauTT | 21 | auuagcacgcgggugaccuTT | 22 |
| 1185-1207 | AL-DP-6145 | aggumcmacmcmcmgcmgumgcmumaaumTT | 23 | auumagcmacgcgggugaccuTT | 24 |
| 445-467 | AL-DP-6843 | uuccggaccagcccucgggTT | 25 | cccgagggcugguccggaaTT | 26 |
| 445-467 | AL-DP-6146 | umumcmcmggacmcmagcmcmcmumcmgggTT | 27 | cccgagggcugguccggaaTT | 28 |
| 1104-1126 | AL-DP-6844 | uguacaacagcacccgcgaTT | 29 | ucgcgggugcuguuguacaTT | 30 |
| 1104-1126 | AL-DP-6147 | umgumacmaacmagcmacmcmcmgcmgaTT | 31 | ucgcgggugcuguugumacmaTT | 32 |
| 1189-1211 | AL-DP-6845 | cacccgcgugcuaauggugTT | 33 | caccauuagcacgcgggugTT | 34 |
| 1189-1211 | AL-DP-6148 | cmacmcmcmgcmgumgcmumaaumggumgTT | 35 | cmaccmauumagcmacgcgggugTT | 36 |
| 446-468 | AL-DP-6846 | uccggaccagcccucgggaTT | 37 | ucccgagggcugguccggaTT | 38 |
| 446-468 | AL-DP-6149 | umcmcmggacmcmagcmcmcmumcmgggaTT | 39 | ucccgagggcugguccggaTT | 40 |
| 1787-1809 | AL-DP-6847 | uggaaguggauccacagcTT | 41 | gcucguggauccacuuccaTT | 42 |
| 1787-1809 | AL-DP-6150 | umggaagumggaumcmcmacmgagcmTT | 43 | gcucguggauccmacuuccmaTT | 44 |
| 1806-1828 | AL-DP-6848 | ccaagggcuaccaugccaaTT | 45 | uuggcauggguagcccuuggTT | 46 |
| 1806-1828 | AL-DP-6151 | cmcmaagggcmumacmcmaumgcmcmaaTT | 47 | uuggcmauggumagcccuuggTT | 48 |
| 1187-1209 | AL-DP-6849 | gucacccgcgugcuaauggTT | 49 | ccauuagcacgcgggugacTT | 50 |
| 1187-1209 | AL-DP-6262 | gumcmacmcmcmgcmgumgcmumaaumggTT | 51 | ccmauumagcmacgcgggugacTT | 52 |
| 1106-1128 | AL-DP-6850 | uacaacagcacccgcgaccTT | 53 | ggucgcgggugcuguuguaTT | 54 |
| 1106-1128 | AL-DP-6263 | umacmaacmagcmacmcmcmgcmgacmcmTT | 55 | ggucgcgggugcuguugumaTT | 56 |
| 1804-1826 | AL-DP-6851 | gcccaagggcuaccaugccTT | 57 | ggcaugguagcccuugggcTT | 58 |
| 1804-1826 | AL-DP-6264 | gcmcmcmaagggcmumacmcmaumgcmcmTT | 59 | ggcmaugguumagcccuugggcTT | 60 |
| 1790-1812 | AL-DP-6852 | aaguggauccacgagcccaTT | 61 | ugggcucguggauccacuuTT | 62 |
| 1790-1812 | AL-DP-6265 | aagumggaumcmcmacmgagcmcmcmaTT | 63 | ugggcucguggauccmacuuTT | 64 |
| 239-261 | AL-DP-6853 | gggaggagggacgagcuggTT | 65 | ccagcucgucccucuccccTT | 66 |
| 239-261 | AL-DP-6266 | gggaggagggacmgagcmumggTT | 67 | ccmagcucgucccucuccccTT | 68 |
| 1107-1129 | AL-DP-6854 | acaacagcacccgcgaccgTT | 69 | cggucgcgggugcuguuguTT | 70 |
| 1107-1129 | AL-DP-6267 | acmaacmagcmacmcmcmgcmgacmcmgTT | 71 | cggucgcgggugcuguuguTT | 72 |
| 1807-1829 | AL-DP-6855 | caagggcuaccaugccaacTT | 73 | guuggcauggguagcccuugTT | 74 |
| 1807-1829 | AL-DP-6268 | cmaagggcmumacmcmaumgcmcmaacmTT | 75 | guuggcmauggumagcccuugTT | 76 |
| 447-469 | AL-DP-6856 | ccggaccagcccucgggagTT | 77 | cucccgagggcugguccggTT | 78 |

TABLE 1-continued

Oligonucleotide sequences of siRNAs specific for TGF-beta

| Position of target sequence in NM_000660.3 | Duplex identifier | sense strand sequence[1] | SEQ ID NO: | antisense strand sequence[1] | SEQ ID NO: |
|---|---|---|---|---|---|
| 447-469 | AL-DP-6269 | cmcmggacmcmagcmcmcmumcmgggagTT | 79 | cucccgagggcugguccggTT | 80 |
| 1711-1733 | AL-DP-6857 | caacuauugcuucagcuccTT | 81 | ggagcugaagcaauaguugTT | 82 |
| 1711-1733 | AL-DP-6270 | cmaacmumaumumgcmumummagcmumcmcmTT | 83 | ggagcugaagcmaaumaguugTT | 84 |
| 1748-1770 | AL-DP-6858 | gugcggcagcuguacauugTT | 85 | caauguacagcugccgcacTT | 86 |
| 1748-1770 | AL-DP-6271 | gumgcmggcmagcmumgumacmaumumgTT | 87 | cmaaugumacmagcugccgcmacTT | 88 |
| 1788-1810 | AL-DP-6859 | ggaaguggauccacgagccTT | 89 | ggcucguggauccacuuccTT | 90 |
| 1788-1810 | AL-DP-6272 | ggaagumggaumcmcmacmgagcmcmcmTT | 91 | ggcucguggauccmacuuccTT | 92 |
| 1789-1811 | AL-DP-6860 | gaaguggauccacgagcccTT | 93 | gggcucguggauccacuucTT | 94 |
| 1789-1811 | AL-DP-6273 | gaagumggaumcmcmacmgagcmcmcmcmTT | 95 | gggcucguggauccmacuucTT | 96 |
| 1798-1820 | AL-DP-6861 | ccacgagcccaagggcuacTT | 97 | guagcccuugggcucguggTT | 98 |
| 1798-1820 | AL-DP-6274 | cmcmacmgagcmcmcmaagggcmumacmTT | 99 | gumagcccuugggcucguggTT | 100 |
| 1802-1824 | AL-DP-6862 | gagcccaagggcuaccaugTT | 101 | cauggguagcccuugggcucTT | 102 |
| 1802-1824 | AL-DP-6275 | gagcmcmcmaagggcmumacmcmaumgTT | 103 | cmauggumagcccuugggcucTT | 104 |
| 1803-1825 | AL-DP-6863 | agcccaagggcuaccaugcTT | 105 | gcauggguagcccuugggcuTT | 106 |
| 1803-1825 | AL-DP-6276 | agcmcmcmaagggcmumacmcmaumgcmTT | 107 | gcmauggumagcccuugggcuTT | 108 |
| 1926-1948 | AL-DP-6864 | cgugcugcgugccgcaggcTT | 109 | gccugcggcacgcagcacgTT | 110 |
| 1926-1948 | AL-DP-6277 | cmgumgcmumgcmgumgcmcmgcmaggcmTT | 111 | gccugcggcmacgcmagcmacgTT | 112 |

[1]a, g, c, u: ribonucleotide 5'-monophosphates (except where in 5'-most position, see below); cm: 2'-O-methyl-cytidine-5'-monophosphate (except where in 5'-most position, see below); um: 2'-O-methyl-uridine-5'-monophosphate (except where in 5'-most position, see below); T: deoxythymidine 5'-monophosphate; T: deoxythymidine 5'-monothiophosphate; all sequences given 5' → 3'; due to synthesis procedures, the 5'-most nucleic acid is anucleoside, i.e. does not bear a 5'-monophosate group The iRNA agents of the invention can either contain only naturally occurring ribonucleotide subunits, or can be synthesized so as to contain one or more modifications to the base, the sugar or the phosphate group of one or more of the ribonucleotide 5'-monophosphate subunits that is included in the agent. The iRNA agent can be further modified so as to be attached to a ligand that is selected to improve stability, distribution or cellular uptake of the agent, e.g. cholesterol. The iRNA agents can further be in isolated form or can be part of a pharmaceutical composition used for the methods described herein, particularly as a pharmaceutical composition formulated for delivery to the lung or formulated for parenteral administration. The pharmaceutical compositions can contain one or more iRNA agents, and in some embodiments, will contain two or more iRNA agents, each one directed to a different segment of a TGF-beta gene or a different TGF-beta gene.

In a preferred embodiment, an iRNA agent of the invention reduces the level of TGF-beta protein secreted by, and/or TGF-beta mRNA found inside, a cell by at least 20% or more. Thus, the iRNA agent may preferably be chosen from the group of AD-14501, AD-14503, AD-14507, AD-14554, AD-14594, AD-14597, AD-14633, AL-DP-6858, AL-DP-6857, AL-DP-6859, AL-DP-6848, AL-DP-6862, AD-14419, AD-14420, AD-14421, AD-14422, AD-14423, AD-14428, AD-14430, AD-14434, AD-14438, AD-14449, AD-14453, AD-14459, AD-14460, AD-14464, AD-14469, AD-14470, AD-14473, AD-14474, AD-14476, AD-14486, AD-14490, AD-14495, AD-14496, AD-14497, AD-14509, AD-14515, AD-14522, AD-14526, AD-14540, AD-14552, AD-14555, AD-14557, AD-14565, AD-14567, AD-14568, AD-14582, AD-14588, AD-14590, AD-14592, AD-14598, AD-14600, AD-14601, AD-14603, AD-14604, AD-14608, AD-14610, AD-14612, AD-14614, AD-14622, AD-14634, AD-14635, AL-DP-6845, AL-DP-6852, AL-DP-6838, AL-DP-6855, AL-DP-6264, AL-DP-6851, AL-DP-6842, AL-DP-6837, AD-14425, AD-14426, AD-14427, AD-14429, AD-14431, AD-14436, AD-14437, AD-14441, AD-14448, AD-14458, AD-14463, AD-14467, AD-14477, AD-14482, AD-14483, AD-14491, AD-14502, AD-14505, AD-14508, AD-14512, AD-14513, AD-14519, AD-14524, AD-14537, AD-14546, AD-14548, AD-14549, AD-14559, AD-14563, AD-14564, AD-14569, AD-14578, AD-14579, AD-14587, AD-14595, AD-14599, AD-14607, AD-14609, AD-14629, AD-14631, AD-14637, AL-DP-6840, AL-DP-6860, AL-DP-6861, AL-DP-6849, AL-DP-6272, AL-DP-6271, AL-DP-6847, AL-DP-6863, AD-14447, AD-14451, AD-14471, AD-14484, AD-14487, AD-14498, AD-14523, AD-14527, AD-14529, AD-14539, AD-14541, AD-14558, AD-14561, AD-14573, AD-14589, AD-14596, AD-14605, AD-14615, AD-14626, AD-14630, AL-DP-6846, AL-DP-6853, AL-DP-6856, AL-DP-6864, AL-DP-6844, AL-DP-6143, AD-14432, AD-14480, AD-14485, AD-14488, AD-14499, AD-14504, AD-14516, AD-14518, AD-14520, AD-14547, AD-14572, AD-14577, AD-14580, AD-14583, AD-14584, AD-14618, AD-14621, AD-14625, AL-DP-6276, AD-14435, AD-14445, AD-14450, AD-14456, AD-14466, AD-14475, AD-14489, AD-14492, AD-14511, AD-14535, AD-14536, AD-14538, AD-14553, AD-14560, AD-14562, AD-14576, AD-14581, AD-14586, AD-14627, AL-DP-6150 AL-DP-6850, AD-14433, AD-14472, AD-14478, AD-14493, AD-14510, AD-14544, AD-14566, AD-14570, AD-14575, AD-14593, AD-14613, AL-DP-6269, AL-DP-6270, AL-DP-6147, AL-DP-6262, AL-DP-6841, AL-DP-6274, AL-DP-6843, AL-DP-6145, AD-14424, AD-14442, AD-14444, AD-14446, AD-14454, AD-14525, AD-14543, AD-14571, AD-14606, AD-14611, AD-14616, AD-14617, AD-14619, and AD-14638 (the "20% group").

More preferably, an iRNA agent of the invention reduces the level of TGF-beta protein secreted by, and/or TGF-beta mRNA found inside, a cell by at least 30% or more. Thus, the iRNA agent may preferably be chosen from the group of AD-14501, AD-14503, AD-14507, AD-14554, AD-14594, AD-14597, AD-14633, AL-DP-6858, AL-DP-6857, AL-DP-6859, AL-DP-6848, AL-DP-6862, AD-14419, AD-14420, AD-14421, AD-14422, AD-14423, AD-14428, AD-14430, AD-14434, AD-14438, AD-14449, AD-14453, AD-14459, AD-14460, AD-14464, AD-14469, AD-14470, AD-14473, AD-14474, AD-14476, AD-14486, AD-14490, AD-14495, AD-14496, AD-14497, AD-14509, AD-14515, AD-14522, AD-14526, AD-14540, AD-14552, AD-14555, AD-14557, AD-14565, AD-14567, AD-14568, AD-14582, AD-14588, AD-14590, AD-14592, AD-14598, AD-14600, AD-14601, AD-14603, AD-14604, AD-14608, AD-14610, AD-14612, AD-14614, AD-14622, AD-14634, AD-14635, AL-DP-6845, AL-DP-6852, AL-DP-6838, AL-DP-6855, AL-DP-6264, AL-DP-6851, AL-DP-6842, AL-DP-6837, AD-14425, AD-14426, AD-14427, AD-14429, AD-14431, AD-14436, AD-14437, AD-14441, AD-14448, AD-14458, AD-14463, AD-14467, AD-14477, AD-14482, AD-14483, AD-14491, AD-14502, AD-14505, AD-14508, AD-14512, AD-14513, AD-14519, AD-14524, AD-14537, AD-14546, AD-14548, AD-14549, AD-14559, AD-14563, AD-14564, AD-14569, AD-14578, AD-14579, AD-14587, AD-14595, AD-14599, AD-14607, AD-14609, AD-14629, AD-14631, AD-14637, AL-DP-6840, AL-DP-6860, AL-DP-6861, AL-DP-6849, AL-DP-6272, AL-DP-6271, AL-DP-6847, AL-DP-6863, AD-14447, AD-14451, AD-14471, AD-14484, AD-14487, AD-14498, AD-14523, AD-14527, AD-14529, AD-14539, AD-14541, AD-14558, AD-14561, AD-14573, AD-14589, AD-14596, AD-14605, AD-14615, AD-14626, AD-14630, AL-DP-6846, AL-DP-6853, AL-DP-6856, AL-DP-6864, AL-DP-6844, AL-DP-6143, AD-14432, AD-14480, AD-14485, AD-14488, AD-14499, AD-14504, AD-14516, AD-14518, AD-14520, AD-14547, AD-14572, AD-14577, AD-14580, AD-14583, AD-14584, AD-14618, AD-14621, AD-14625, AL-DP-6276, AD-14435, AD-14445, AD-14450, AD-14456, AD-14466, AD-14475, AD-14489, AD-14492, AD-14511, AD-14535, AD-14536, AD-14538, AD-14553, AD-14560, AD-14562, AD-14576, AD-14581, AD-14586, AD-14627, AL-DP-6150 AL-DP-6850, AD-14433, AD-14472, AD-14478, AD-14493, AD-14510, AD-14544, AD-14566, AD-14570, AD-14575, AD-14593, and AD-14613 (the "30% group").

More preferably, an iRNA agent of the invention reduces the level of TGF-beta protein secreted by, and/or TGF-beta mRNA found inside, a cell by at least 40% or more. Thus, the iRNA agent may preferably be chosen from the group of AD-14501, AD-14503, AD-14507, AD-14554, AD-14594, AD-14597, AD-14633, AL-DP-6858, AL-DP-6857, AL-DP-6859, AL-DP-6848, AL-DP-6862, AD-14419, AD-14420, AD-14421, AD-14422, AD-14423, AD-14428, AD-14430, AD-14434, AD-14438, AD-14449, AD-14453, AD-14459, AD-14460, AD-14464, AD-14469, AD-14470, AD-14473, AD-14474, AD-14476, AD-14486, AD-14490, AD-14495, AD-14496, AD-14497, AD-14509, AD-14515, AD-14522, AD-14526, AD-14540, AD-14552, AD-14555, AD-14557, AD-14565, AD-14567, AD-14568, AD-14582, AD-14588, AD-14590, AD-14592, AD-14598, AD-14600, AD-14601, AD-14603, AD-14604, AD-14608, AD-14610, AD-14612, AD-14614, AD-14622, AD-14634, AD-14635, AL-DP-6845, AL-DP-6852, AL-DP-6838, AL-DP-6855, AL-DP-6264, AL-DP-6851, AL-DP-6842, AL-DP-6837, AD-14425, AD-14426, AD-14427, AD-14429, AD-14431, AD-14436, AD-14437, AD-14441, AD-14448, AD-14458, AD-14463, AD-14467, AD-14477, AD-14482, AD-14483, AD-14491, AD-14502, AD-14505, AD-14508, AD-14512, AD-14513, AD-14519, AD-14524, AD-14537, AD-14546, AD-14548, AD-14549, AD-14559, AD-14563, AD-14564, AD-14569, AD-14578, AD-14579, AD-14587, AD-14595, AD-14599, AD-14607, AD-14609, AD-14629, AD-14631, AD-14637, AL-DP-6840, AL-DP-6860, AL-DP-6861, AL-DP-6849, AL-DP-6272, AL-DP-6271, AL-DP-6847, AL-DP-6863, AD-14447, AD-14451, AD-14471, AD-14484, AD-14487, AD-14498, AD-14523, AD-14527, AD-14529, AD-14539, AD-14541, AD-14558, AD-14561, AD-14573, AD-14589, AD-14596, AD-14605, AD-14615, AD-14626, AD-14630, AL-DP-6846, AL-DP-6853, AL-DP-6856, AL-DP-6864, AL-DP-6844, AL-DP-6143, AD-14432, AD-14480, AD-14485, AD-14488, AD-14499, AD-14504, AD-14516, AD-14518, AD-14520, AD-14547, AD-14572, AD-14577, AD-14580, AD-14583, AD-14584, AD-14618, AD-14621, AD-14625, AL-DP-6276, AD-14435, AD-14445, AD-14450, AD-14456, AD-14466, AD-14475, AD-14489, AD-14492, AD-14511, AD-14535, AD-14536, AD-14538, AD-14553, AD-14560, AD-14562, AD-14576, AD-14581, AD-14586, and AD-14627 (the "40% group").

More preferably, an iRNA agent of the invention reduces the level of TGF-beta protein secreted by, and/or TGF-beta mRNA found inside, a cell by at least 50% or more. Thus, the iRNA agent may preferably be chosen from the group of AD-14501, AD-14503, AD-14507, AD-14554, AD-14594, AD-14597, AD-14633, AL-DP-6858, AL-DP-6857, AL-DP-6859, AL-DP-6848, AL-DP-6862, AD-14419, AD-14420, AD-14421, AD-14422, AD-14423, AD-14428, AD-14430, AD-14434, AD-14438, AD-14449, AD-14453, AD-14459, AD-14460, AD-14464, AD-14469, AD-14470, AD-14473, AD-14474, AD-14476, AD-14486, AD-14490, AD-14495, AD-14496, AD-14497, AD-14509, AD-14515, AD-14522, AD-14526, AD-14540, AD-14552, AD-14555, AD-14557, AD-14565, AD-14567, AD-14568, AD-14582, AD-14588, AD-14590, AD-14592, AD-14598, AD-14600, AD-14601, AD-14603, AD-14604, AD-14608, AD-14610, AD-14612, AD-14614, AD-14622, AD-14634, AD-14635, AL-DP-6845, AL-DP-6852, AL-DP-6838, AL-DP-6855, AL-DP-6264, AL-DP-6851, AL-DP-6842, AL-DP-6837, AD-14425, AD-14426, AD-14427, AD-14429, AD-14431, AD-14436, AD-14437, AD-14441, AD-14448, AD-14458, AD-14463, AD-14467, AD-14477, AD-14482, AD-14483, AD-14491, AD-14502, AD-14505, AD-14508, AD-14512, AD-14513, AD-14519, AD-14524, AD-14537, AD-14546, AD-14548, AD-14549, AD-14559, AD-14563, AD-14564, AD-14569, AD-14578, AD-14579, AD-14587, AD-14595, AD-14599, AD-14607, AD-14609, AD-14629, AD-14631, AD-14637, AL-DP-6840, AL-DP-6860, AL-DP-6861, AL-DP-6849, AL-DP-6272, AL-DP-6271, AL-DP-6847, AL-DP-6863, AD-14447, AD-14451, AD-14471, AD-14484, AD-14487, AD-14498, AD-14523, AD-14527, AD-14529, AD-14539, AD-14541, AD-14558, AD-14561, AD-14573, AD-14589, AD-14596, AD-14605, AD-14615, AD-14626, AD-14630, AL-DP-6846, AL-DP-6853, AL-DP-6856, AL-DP-6864, AL-DP-6844, AL-DP-6143, AD-14432, AD-14480, AD-14485, AD-14488, AD-14499, AD-14504, AD-14516, AD-14518, AD-14520, AD-14547, AD-14572, AD-14577, AD-14580, AD-14583, AD-14584, AD-14618, AD-14621, and AD-14625 (the "50% group").

Yet more preferably, an iRNA agent of the invention reduces the level of TGF-beta protein secreted by, and/or TGF-beta mRNA found inside, a cell by at least 60% or more. Thus, the iRNA agent may preferably be chosen from the group of AD-14501, AD-14503, AD-14507, AD-14554, AD-14594, AD-14597, AD-14633, AL-DP-6858, AL-DP-6857, AL-DP-6859, AL-DP-6848, AL-DP-6862, AD-14419, AD-14420, AD-14421, AD-14422, AD-14423, AD-14428, AD-14430, AD-14434, AD-14438, AD-14449, AD-14453, AD-14459, AD-14460, AD-14464, AD-14469, AD-14470, AD-14473, AD-14474, AD-14476, AD-14486, AD-14490, AD-14495, AD-14496, AD-14497, AD-14509, AD-14515, AD-14522, AD-14526, AD-14540, AD-14552, AD-14555, AD-14557, AD-14565, AD-14567, AD-14568, AD-14582, AD-14588, AD-14590, AD-14592, AD-14598, AD-14600, AD-14601, AD-14603, AD-14604, AD-14608, AD-14610, AD-14612, AD-14614, AD-14622, AD-14634, AD-14635, AL-DP-6845, AL-DP-6852, AL-DP-6838, AL-DP-6855, AL-DP-6264, AL-DP-6851, AL-DP-6842, AL-DP-6837, AD-14425, AD-14426, AD-14427, AD-14429, AD-14431, AD-14436, AD-14437, AD-14441, AD-14448, AD-14458, AD-14463, AD-14467, AD-14477, AD-14482, AD-14483, AD-14491, AD-14502, AD-14505, AD-14508, AD-14512, AD-14513, AD-14519, AD-14524, AD-14537, AD-14546, AD-14548, AD-14549, AD-14559, AD-14563, AD-14564, AD-14569, AD-14578, AD-14579, AD-14587, AD-14595, AD-14599, AD-14607, AD-14609, AD-14629, AD-14631, AD-14637, AL-DP-6840, AL-DP-6860, AL-DP-6861, AL-DP-6849, AL-DP-6272, AL-DP-6271, AL-DP-6847, AL-DP-6863, AD-14447, AD-14451, AD-14471, AD-14484, AD-14487, AD-14498, AD-14523, AD-1.4527, AD-14529, AD-14539, AD-14541, AD-14558, AD-14561, AD-14573, AD-14589, AD-14596, AD-14605, AD-14615, AD-14626, and AD-14630 (the "60% group").

Yet more preferably, an iRNA agent of the invention reduces the level of TGF-beta protein secreted by, and/or TGF-beta mRNA found inside, a cell by at least 70% or more. Thus, the iRNA agent may preferably be chosen from the group of AD-14501, AD-14503, AD-14507, AD-14554, AD-14594, AD-14597, AD-14633, AL-DP-6858, AL-DP-6857, AL-DP-6859, AL-DP-6848, AL-DP-6862, AD-14419, AD-14420, AD-14421, AD-14422, AD-14423, AD-14428, AD-14430, AD-14434, AD-14438, AD-14449, AD-14453, AD-14459, AD-14460, AD-14464, AD-14469, AD-14470, AD-14473, AD-14474, AD-14476, AD-14486, AD-14490, AD-14495, AD-14496, AD-14497, AD-14509, AD-14515, AD-14522, AD-14526, AD-14540, AD-14552, AD-14555, AD-14557, AD-14565, AD-14567, AD-14568, AD-14582, AD-14588, AD-14590, AD-14592, AD-14598, AD-14600, AD-14601, AD-14603, AD-14604, AD-14608, AD-14610, AD-14612, AD-14614, AD-14622, AD-14634, AD-14635, AL-DP-6845, AL-DP-6852, AL-DP-6838, AL-DP-6855, AL-DP-6264, AL-DP-6851, AL-DP-6842, AL-DP-6837, AD-14425, AD-14426, AD-14427, AD-14429, AD-14431, AD-14436, AD-14437, AD-14441, AD-14448, AD-14458, AD-14463, AD-14467, AD-14477, AD-14482, AD-14483, AD-14491, AD-14502, AD-14505, AD-14508, AD-14512, AD-14513, AD-14519, AD-14524, AD-14537, AD-14546, AD-14548, AD-14549, AD-14559, AD-14563, AD-14564, AD-14569, AD-14578, AD-14579, AD-14587, AD-14595, AD-14599, AD-14607, AD-14609, AD-14629, AD-14631, and AD-14637 (the "70% group").

Yet more preferably, an iRNA agent of the invention reduces the level of TGF-beta protein secreted by, and/or TGF-beta mRNA found inside, a cell by at least 80% or more. Thus, the iRNA agent may preferably be chosen from the group of AD-14501, AD-14503, AD-14507, AD-14554, AD-14594, AD-14597, AD-14633, AL-DP-6858, AL-DP-6857, AL-DP-6859, AL-DP-6848, AL-DP-6862, AD-14419, AD-14420, AD-14421, AD-14422, AD-14423, AD-14428, AD-14430, AD-14434, AD-14438, AD-14449, AD-14453, AD-14459, AD-14460, AD-14464, AD-14469, AD-14470, AD-14473, AD-14474, AD-14476, AD-14486, AD-14490, AD-14495, AD-14496, AD-14497, AD-14509, AD-14515, AD-14522, AD-14526, AD-14540, AD-14552, AD-14555, AD-14557, AD-14565, AD-14567, AD-14568, AD-14582, AD-14588, AD-14590, AD-14592, AD-14598, AD-14600, AD-14601, AD-14603, AD-14604, AD-14608, AD-14610, AD-14612, AD-14614, AD-14622, AD-14634, and AD-14635 (the "80% group").

Yet more preferably, an iRNA agent of the invention reduces the level of TGF-beta protein secreted by, and/or TGF-beta mRNA found inside, a cell by at least 90% or more. Thus, the iRNA agent may preferably be chosen from the group of AD-14501, AD-14503, AD-14507, AD-14554, AD-14594, AD-14597, and AD-14633 (the "90% group").

The present invention provides methods for reducing the level of TGF-beta protein and TGF-beta mRNA in a cell. Such methods optionally comprise the step of administering one of the iRNA agents of the present invention to a subject as further described below. The present methods utilize the cellular mechanisms involved in RNA interference to selectively degrade the TGF-beta mRNA in a cell and are comprised of the step of contacting a cell with one of the TGF-beta iRNA agents of the present invention. Such methods can be performed directly on a cell or can be performed on a mammalian subject by administering to a subject one of the iRNA agents/pharmaceutical compositions of the present invention. Reduction of TGF-beta mRNA in a cell results in a reduction in the amount of TGF-beta protein produced, and in an organism (as shown in the Examples).

The methods and compositions of the invention, e.g., the methods and iRNA agent compositions can be used with any dosage and/or formulation described herein, as well as with any route of administration described herein.

In another aspect, the invention features a method for treating or preventing a disease or condition associated with undesired TGF-beta signaling in a subject. The method can include administering to the subject a composition of the invention under conditions suitable for the treatment or prevention of the disease or condition associated with undesired TGF-beta signaling in the subject, alone or in conjunction with one or more other therapeutic compounds.

In one embodiment, the iRNA agent is administered at or near the site of undesired TGF-beta signaling, e.g., direct injection at the site, or by a catheter or other placement device (e.g., an implant including a porous, non-porous, or gelatinous material). In another embodiment the iRNA agent is administered via pulmonary delivery, e.g. by inhalation, which may be nasal and/or oral.

In one embodiment, an iRNA agent is administered repeatedly. Administration of an iRNA agent can be carried out over a range of time periods. It can be administered hourly, daily, once every few days, weekly, or monthly. The timing of administration can vary from patient to patient, depending upon such factors as the severity of a patient's symptoms. For example, an effective dose of an iRNA agent can be administered to a patient once a month for an indefinite period of time, or until the patient no longer requires therapy. In addition, sustained release compositions containing an iRNA agent can be used to maintain a relatively constant dosage in the area of the target TGF-beta nucleotide sequences.

In another embodiment, an iRNA agent is delivered at a dosage on the order of about 0.00001 mg to about 3 mg per kg body weight of the subject to be treated, or preferably about 0.0001-0.001 mg per kg body weight, about 0.03-3.0 mg per kg body weight, about 0.1-3.0 mg per kg body weight or about 0.3-3.0 mg per kg body weight.

In another embodiment, an iRNA agent is administered prophylactically such as to prevent or slow the onset of a disease or disorder or condition associated with undesired TGF-beta signaling. For example, an iRNA can be administered to a patient who is susceptible to or otherwise at risk for such a disease or disorder.

In another aspect, a method of inhibiting TGF-beta expression is provided. One such method includes administering an effective amount of an iRNA agent including sense and antisense sequences capable of forming an RNA duplex. The sense sequence of the iRNA agent can include a nucleotide sequence substantially identical to a target sequence of about 19 to 23 nucleotides of TGF-beta mRNA, and the antisense sequence can include a nucleotide sequence complementary to a target sequence of about 19-23 nucleotides of TGF-beta mRNA.

In one aspect, methods of treating any disease or disorder associated with undesired TGF-beta signaling are provided.

In another aspect, a method of treating idiopathic pulmonary fibrosis is provided. One such method includes administering a therapeutically effective amount of an iRNA agent that includes sense and antisense sequences capable of forming an RNA duplex. The sense sequence can include a nucleotide sequence substantially identical to a target sequence of about 19 to 23 nucleotides of TGF-beta mRNA. The antisense sequence can include a nucleotide sequence complementary to a target sequence of about 19 to 23 nucleotides of TGF-beta mRNA.

In one embodiment, a human has been diagnosed with a disease or disorder associated with undesired TGF-beta signaling. In one embodiment, said disease or disorder is Interstitial Lung Disease (ILD). In a preferred embodiment, the human has been diagnosed with one of: Idiopathic pulmonary fibrosis, Hypersensitivity pneumonitis, Sarcoidosis, Eosinophilic granuloma, Wegener's granulomatosis, Idiopathic pulmonary hemosiderosis, and Bronchiolitis obliterans. In a particularly preferred embodiment, the human has been diagnosed with idiopathic pulmonary fibrosis.

In another aspect, the invention features a kit containing an iRNA agent of the invention. The iRNA agent of the kit can be chemically modified and can be useful for modulating the expression of a TGF-beta target gene in a cell, tissue or organism. In one embodiment, the kit contains more than one iRNA agent of the invention.

The details of one or more embodiments of the invention are set forth in the description below. Other features, objects, and advantages of the invention will be apparent from this description and from the claims. This application incorporates all cited references, patents, and patent applications by references in their entirety for all purposes.

DETAILED DESCRIPTION

For ease of exposition the term "nucleotide" or "ribonucleotide" is sometimes used herein in reference to one or more monomeric subunits of an RNA agent. It will be understood that the usage of the term "ribonucleotide" or "nucleotide" herein can, in the case of a modified RNA or nucleotide surrogate, also refer to a modified nucleotide, or surrogate replacement moiety, as further described below, at one or more positions.

An "RNA agent" as used herein, is an unmodified RNA, modified RNA, or nucleoside surrogate, all of which are described herein or are well known in the RNA synthetic art. While numerous modified RNAs and nucleoside surrogates are described, preferred examples include those which have greater resistance to nuclease degradation than do unmodified RNAs. Examples include those that have a 2' sugar modification, a modification in a single strand overhang, such as a 3' single strand overhang, or, particularly if single stranded, a 5'-modification which includes one or more phosphate groups or one or more analogs of a phosphate group.

An "iRNA agent" (abbreviation for "interfering RNA agent") as used herein, is an RNA agent, which can downregulate the expression of a target gene, e.g., a TGF-beta gene, and preferably a human TGF-beta gene. While not wishing to be bound by theory, an iRNA agent may act by one or more of a number of mechanisms, including post-transcriptional cleavage of a target mRNA sometimes referred to in the art as RNA interference or RNAi, or pre-transcriptional or pre-translational mechanisms. An iRNA agent can be a double stranded (ds) iRNA agent.

A "ds iRNA agent" (abbreviation for "double stranded iRNA agent"), as used herein, is an iRNA agent which includes more than one, and preferably two, strands in which interchain hybridization can form a region of duplex structure. A "strand" herein refers to a contiguous sequence of nucleotides (including non-naturally occurring or modified nucleotides). The two or more strands may be, or each form a part of, separate molecules, or they may be covalently interconnected, e.g. by a linker, e.g. a polyethylene glycol linker, to form but one molecule. At least one strand can include a region which is sufficiently complementary to a target RNA. Such strand is termed the "antisense strand". A second strand comprised in the dsRNA agent that comprises a region complementary to the antisense strand is termed the "sense strand". However, a ds iRNA agent can also be formed from a single RNA molecule which is, at least partly; self-complementary, forming, e.g., a hairpin or panhandle structure, including a duplex region. In such case, the term "strand" refers to one of the regions of the RNA molecule that is complementary to another region of the same RNA molecule.

Although, in mammalian cells, long ds iRNA agents can induce the interferon response which is frequently deleterious, short ds iRNA agents do not trigger the interferon response, at least not to an extent that is deleterious to the cell and/or host. The iRNA agents of the present invention include molecules which are sufficiently short that they do not trigger a deleterious interferon response in mammalian cells. Thus, the administration of a composition of an iRNA agent (e.g., formulated as described herein) to a mammalian cell can be used to silence expression of an TGF-beta gene while circumventing a deleterious interferon response. Molecules that are short enough that they do not trigger a deleterious interferon response are termed siRNA agents or siRNAs herein. "siRNA agent" or "siRNA" as used herein, refers to an iRNA agent, e.g., a ds iRNA agent, that is sufficiently short that it does not induce a deleterious interferon response in a human cell, e.g., it has a duplexed region of less than 60 but preferably less than 50, 40, or 30 nucleotide pairs.

The isolated iRNA agents described herein, including ds iRNA agents and siRNA agents, can mediate silencing of a gene, e.g., by RNA degradation. For convenience, such RNA is also referred to herein as the RNA to be silenced, or target RNA. Such a gene is also referred to as a target gene. Preferably, the RNA to be silenced is a gene product of a TGF-beta gene.

As used herein, the phrases "mediate RNAi", "silence a TGF-beta gene", "reducing the level of TGF-beta mRNA" and/or "reducing the level of TGF-beta protein" all refer to the at least partial suppression of the expression of the TGF-beta gene, as manifested, e.g., by a reduction of the amount of mRNA transcribed from the TGF-beta gene which may be isolated from a first cell or group of cells in which the TGF-beta gene is transcribed and which has or have been treated such that the expression of the TGF-beta gene is inhibited, as compared to a second cell or group of cells substantially identical to the first cell or group of cells but which has or have not been so treated (control cells). Alternatively, the degree of inhibition may be given in terms of a reduction of a parameter that is functionally linked to TGF-beta gene transcription, e.g. the amount of protein encoded by the TGF-beta gene which is secreted by a cell, or the number of cells displaying a certain phenotype associated with TGF-beta signalling. The degree of inhibition is usually expressed in terms of $$\frac{(mRNA \text{ in control cells}) - (mRNA \text{ in treated cells})}{(mRNA \text{ in control cells})} \cdot 100\%$$

("mRNA" may be replaced by another parameter used to assess TGF-beta gene expression, where applicable)

For example, in certain instances, expression of the TGF-beta gene is suppressed by at least about 20%, 25%, 35%, or 50% by administration of the double-stranded oligonucleotide of the invention. In a preferred embodiment, the TGF-beta gene is suppressed by at least about 60%, 70%, or 80% by administration of the double-stranded oligonucleotide of the invention. In a more preferred embodiment, the TGF-beta gene is suppressed by at least about 85%, 90%, or 95% by administration of the double-stranded oligonucleotide of the invention. In a most preferred embodiment, the TGF-beta gene is suppressed by at least about 98%, 99% or more by administration of the double-stranded oligonucleotide of the invention.

In principle, TGF-beta gene silencing may be determined in any cell expressing the target, either constitutively or by genomic engineering, and by any appropriate assay. However, when a reference is needed in order to determine whether a given siRNA inhibits the expression of the TGF-beta gene by a certain degree and therefore is encompassed by the instant invention, the assay provided in the Examples below shall serve as such reference.

As used herein, and unless otherwise indicated, the term "complementary," when used to describe a first nucleotide sequence in relation to a second nucleotide sequence, refers to the ability of an oligonucleotide or polynucleotide comprising the first nucleotide sequence to hybridize and form a duplex structure under certain conditions with an oligonucleotide or polynucleotide comprising the second nucleotide sequence, as will be understood by the skilled person. Such conditions can, for example, be stringent conditions, where stringent conditions may include: 400 mM NaCl, 40 mM PIPES pH 6.4, 1 mM EDTA, 50° C. or 70° C. for 12-16 hours followed by washing. Other conditions, such as physiologically relevant conditions as may be encountered inside an organism, can apply. The skilled person will be able to determine the set of conditions most appropriate for a test of complementarity of two sequences in accordance with the ultimate application of the hybridized nucleotides.

This includes base-pairing of the oligonucleotide or polynucleotide comprising the first nucleotide sequence to the oligonucleotide or polynucleotide comprising the second nucleotide sequence over the entire length of the first and second nucleotide sequence. Such sequences can be referred to as "fully complementary" with respect to each other herein. However, where a first sequence is referred to as "substantially complementary" with respect to a second sequence herein, the two sequences can be fully complementary, or they may form one or more, but preferably not more than 4, 3 or 2 mismatched base pairs upon hybridization, while retaining the ability to hybridize under the conditions most relevant to their ultimate application. However, where two oligonucleotides are designed to form, upon hybridization, one or more single stranded overhangs, such overhangs shall not be regarded as mismatches with regard to the determination of complementarity. For example, a dsRNA comprising one oligonucleotide 21 nucleotides in length and another oligonucleotide 23 nucleotides in length, wherein the longer oligonucleotide comprises a sequence of 21 nucleotides that is fully complementary to the shorter oligonucleotide, may yet be referred to as "fully complementary" for the purposes of the invention.

"Complementary" sequences, as used herein, may also include, or be formed entirely from, non-Watson-Crick base pairs and/or base pairs formed from non-natural and modified nucleotides, in as far as the above requirements with respect to their ability to hybridize are fulfilled.

The terms "complementary", "fully complementary" and "substantially complementary" herein may be used with respect to the base matching between the sense strand and the antisense strand of a dsRNA, or between the antisense strand of a dsRNA and a target sequence, as will be understood from the context of their use.

As used herein, "essentially identical" when used referring to a first nucleotide sequence in comparison to a second nucleotide sequence means that the first nucleotide sequence is identical to the second nucleotide sequence except for up to one, two or three nucleotide substitutions (e.g. adenosine replaced by uracil).

As used herein, a "subject" refers to a mammalian organism undergoing treatment for a disorder associated with undesired TGF-beta signaling, such as undergoing treatment prophylactically or therapeutically to prevent TGF-beta production. The subject can be any mammal, such as a primate, cow, horse, mouse, rat, dog, pig, goat. In the preferred embodiment, the subject is a human.

As used herein, "target sequence" refers to a contiguous portion of the nucleotide sequence of an mRNA molecule formed during the transcription of a TGF-beta gene, including mRNA that is a product of RNA processing of a primary transcription product.

As used herein, treating a disorder associated with undesired TGF-beta signaling refers to the amelioration of any biological or pathological endpoints that 1) is mediated in part by the unwanted expression or over expression of TGF-beta in the subject and 2) whose outcome can be affected by reducing the level of TGF-beta gene products present.

As used herein, the phrases "therapeutically effective amount" and "prophylactically effective amount" refer to an amount that provides a therapeutic benefit in the treatment, prevention, or management of pain or an overt symptom of pain. The specific amount that is therapeutically effective can be readily determined by ordinary medical practitioner, and may vary depending on factors known in the art, such as, e.g. the type of pain, the patient's history and age, the stage of pain, and the administration of other anti-pain agents.

As used herein, a "pharmaceutical composition" comprises a pharmacologically effective amount of a dsRNA and a pharmaceutically acceptable carrier. As used herein, "pharmacologically effective amount," "therapeutically effective amount" or simply "effective amount" refers to that amount of an RNA effective to produce the intended pharmacological, therapeutic or preventive result. For example, if a given clinical treatment is considered effective when there is at least a 25% reduction in a measurable parameter associated with a disease or disorder, a therapeutically effective amount of a drug for the treatment of that disease or disorder is the amount necessary to effect at least a 25% reduction in that parameter.

The term "pharmaceutically acceptable carrier" refers to a carrier for administration of a therapeutic agent. Such carriers include, but are not limited to, saline, buffered saline, dextrose, water, glycerol, ethanol, and combinations thereof. The term specifically excludes cell culture medium. For drugs administered orally, pharmaceutically acceptable carriers include, but are not limited to pharmaceutically acceptable excipients such as inert diluents, disintegrating agents, binding agents, lubricating agents, sweetening agents, flavoring agents, coloring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract.

As used herein, a "transformed cell" is a cell into which a vector has been introduced from which a dsRNA molecule may be expressed.

Design and Selection of iRNA Agents

The present invention is based on the demonstration of target gene silencing of the TGF-beta gene in vitro following administration of an iRNA agent results in reducing TGF-beta signaling.

Based on these results, the invention specifically provides an iRNA agent that can be used in reducing TGF-beta levels in a cell or organism, particularly for use in reducing undesired TGF-beta signaling, in isolated form and as a pharmaceutical composition described below. Such agents will include a sense strand having at least 15 or more contiguous nucleotides that are complementary to a TGF-beta gene and an antisense strand having at least 15 or more contiguous nucleotides that are complementary to the sense strand sequence. Particularly useful are iRNA agents that comprise a nucleotide sequence from the TGF-beta gene as provided in Table 1 and Table 5.

Other candidate iRNA agents can be designed by performing, for example, a gene walk analysis of the TGF-beta gene that will serve as the iRNA target. Overlapping, adjacent, or closely spaced candidate agents corresponding to all or some of the transcribed region can be generated and tested. Each of the iRNA agents can be tested and evaluated for the ability to down regulate the target gene expression (see below, "Evaluation of Candidate iRNA agents").

Preferably, the iRNA agents of the present invention are based on and comprise at least 15 or more contiguous nucleotides from one of the iRNA agents shown to be active in Table 1 and Table 5. In such agents, the agent can comprise the entire sequence provided in the table or can comprise 15 or more contiguous residues along with additional nucleotides from contiguous regions of the target gene. Alternatively, an iRNA agent of the instant invention may effect the cleavage of a TGF-beta mRNA within a sequence on the TGF-beta mRNA that is the target sequence of one of the iRNA agents provided in Table 1 and Table 5. The target sequences of the iRNA agents in Table 5 is expressly provided therein, the target sequence of the iRNA agents provided in Table 1 is equal to the sense strand sequence of these agents, minus the 5'-terminal deoxythymidines (and, where applicable, replacing 2'-O-methyl ribonucleotides by ribonucleotides). The skilled person is well aware of how an iRNA agent that cleaves a target mRNA within a given mRNA sequence may be designed. Cleavage of a target mRNA occurs between the two nucleotides hybrized to those in positions 10 and 11, counting 5' to 3', of the iRNA agent's antisense strand (Elbashir, S., et al., EMBO J. 2001, 23:6877). Therefore, an iRNA agent may be designed to cleave at a given site by including a sequence in its antisense strand sufficiently complementary to the target mRNA to hybridize to the target mRNA such that 10 nucleotides of the antisense strand are hybridized 3' to the intended cleavage site on the mRNA, the remainder being hybridized to a sequence 5' on the target mRNA.

An iRNA agent can be rationally designed based on sequence information and desired characteristics and the information provided in Table 1 and Table 5. For example, an iRNA agent can be designed according to the relative melting temperature of the candidate duplex. Generally, the duplex should have a lower melting temperature at the 5' end of the antisense strand than at the 3' end of the antisense strand.

The skilled person is well aware that dsRNAs comprising a duplex structure of between 20 and 23, but specifically 21, base pairs have been hailed as particularly effective in inducing RNA interference (Elbashir et al., EMBO 2001, 20:6877-6888). However, others have found that shorter or longer dsRNAs can be effective as well. In the embodiments described above, by virtue of the nature of the oligonucleotide sequences provided in Table 1 and Table 5, the dsRNAs of the invention can comprise at least one strand of a length of minimally 21 nt. It can be reasonably expected that shorter dsRNAs comprising one of the sequences of Table 1 and Table 5 minus only a few nucleotides on one or both ends may be similarly effective as compared to the dsRNAs described above. Hence, dsRNAs comprising a partial sequence from one of the sequences of Table 1 and Table 5, and differing in their ability to inhibit the expression of a TGF-beta gene in an assay as described herein below by not more than 5, 10, 15, 20, 25, or 30% inhibition from a dsRNA comprising the full sequence, are contemplated by the invention.

Accordingly, the present invention provides iRNA agents comprising a sense strand and antisense strand each comprising a sequence of at least 15, 16, 17, 18, 19, 20, 21 or 23 nucleotides which is essentially identical to, as defined above, a portion of the TGF-beta gene. Exemplified iRNA agents include those that comprise 15 or more contiguous nucleotides from one of the agents provided in Table 1 and Table 5.

The antisense strand of an iRNA agent should be equal to or at least, 15, 16, 17, 18, 19, 25, 29, 40, or 50 nucleotides in length. It should be equal to or less than 50, 40, or 30, nucleotides in length. Preferred ranges are 15-30, 17 to 25, 19 to 23, and 19 to 21 nucleotides in length. Exemplified iRNA agents include those that comprise 15 or more nucleotides from one of the agents in Table 1 and Table 5.

The sense strand of an iRNA agent should be equal to or at least 15, 16, 17, 18, 19, 25, 29, 40, or 50 nucleotides in length. It should be equal to or less than 50, 40, or 30 nucleotides in length. Preferred ranges are 15-30, 17 to 25, 19 to 23, and 19 to 21 nucleotides in length. Exemplified iRNA agents include those that comprise 15 or more nucleotides from one of the agents Table 1 and Table 5.

The double stranded portion of an iRNA agent should be equal to or at least, 15, 16 17, 18, 19, 20, 21, 22, 23, 24, 25, 29, 40, or 50 nucleotide pairs in length. It should be equal to or less than 50, 40, or 30 nucleotides pairs in length. Preferred ranges are 15-30, 17 to 25, 19 to 23, and 19 to 21 nucleotides pairs in length.

The agents provided in Table 1 and Table 5 are 21 nucleotides in length for each strand. The iRNA agents contain a 19 nucleotide double stranded region with a 2 nucleotide overhang on each of the 3' ends of the agent. These agents can be modified as described herein to obtain equivalent agents comprising at least a portion of these sequences (15 or more contiguous nucleotides) and or modifications to the oligonucleotide bases and linkages.

Generally, the iRNA agents of the instant invention include a region of sufficient complementarity to the TGF-beta gene, and are of sufficient length in terms of nucleotides, that the iRNA agent, or a fragment thereof, can mediate down regulation of the specific TGF-beta gene. The antisense strands of the iRNA agents of the present invention are preferably fully complementary to the mRNA sequences of TGF-beta gene. However, it is not necessary that there be perfect complementarity between the iRNA agent and the target, but the correspondence must be sufficient to enable the iRNA agent, or a cleavage product thereof, to direct sequence specific silencing, e.g., by RNAi cleavage of an TGF-beta mRNA.

Therefore, the iRNA agents of the instant invention include agents comprising a sense strand and antisense strand each comprising a sequence of at least 16, 17 or 18 nucleotides which is essentially identical, as defined below, to one of the sequences of a TGF-beta gene such as those agent provided in Table 1 and Table 5, except that not more than 1, 2 or 3 nucleotides per strand, respectively, have been substituted by other nucleotides (e.g. adenosine replaced by uracil), while essentially retaining the ability to inhibit TGF-beta expression in cultured human cells, as defined below. These agents will therefore possess at least 15 or more nucleotides identical to one of the sequences of a TGF-beta gene but 1, 2 or 3 base mismatches with respect to either the target TGF-beta mRNA sequence or between the sense and antisense strand are introduced. Mismatches to the target TGF-beta mRNA sequence, particularly in the antisense strand, are most tolerated in the terminal regions and if present are preferably in a terminal region or regions, e.g., within 6, 5, 4, or 3 nucleotides of a 5' and/or 3' terminus, most preferably within 6, 5, 4, or 3 nucleotides of the 5'-terminus of the sense strand or the 3'-terminus of the antisense strand. The sense strand need only be sufficiently complementary with the antisense strand to maintain the overall double stranded character of the molecule.

It is preferred that the sense and antisense strands be chosen such that the iRNA agent includes a single strand or unpaired region at one or both ends of the molecule, such as those exemplified in Table 1 and Table 5. Thus, an iRNA agent contains sense and antisense strands, preferably paired to contain an overhang, e.g., one or two 5' or 3' overhangs but preferably a 3' overhang of 2-3 nucleotides. Most embodiments will have a 3' overhang. Preferred siRNA agents will have single-stranded overhangs, preferably 3' overhangs, of 1 to 6, preferably 1 to 4, or more preferably 2 or 3 nucleotides, in length, on one or both ends of the iRNA agent. The overhangs can be the result of one strand being longer than the other, or the result of two strands of the same length being staggered. 5'-ends are preferably phosphorylated.

Moreover, the present inventors have discovered that the presence of only one nucleotide overhang strengthens the interference activity of the dsRNA, without affecting its overall stability. dsRNA having only one overhang has proven particularly stable and effective in vivo, as well as in a variety of cells, cell culture mediums, blood, and serum. Preferably, the single-stranded overhang is located at the 3'-terminal end of the antisense strand or, alternatively, at the 3'-terminal end of the sense strand. The dsRNA may also have a blunt end, preferably located at the 5'-end of the antisense strand. Such dsRNAs have improved stability and inhibitory activity, thus allowing administration at low dosages, i.e., less than 5 mg/kg body weight of the recipient per day. Preferably, the antisense strand of the dsRNA has a nucleotide overhang at the 3'-end, and the 5'-end is blunt. In another embodiment, one or more of the nucleotides in the overhang is replaced with a nucleoside thiophosphate.

Preferred lengths for the duplexed region is between 15 and 30, most preferably 18, 19, 20, 21, 22, and 23 nucleotides in length, e.g., in the siRNA agent range discussed above. Embodiments in which the two strands of the siRNA agent are linked, e.g., covalently linked are also included. Hairpin, or other single strand structures which provide the required double stranded region, and preferably a 3' overhang are also within the invention.

Evaluation of Candidate iRNA Agents

A candidate iRNA agent can be evaluated for its ability to down regulate target gene expression. For example, a candidate iRNA agent can be provided, and contacted with a cell, e.g. a human cell that expresses TGF-beta. Alternatively, the cell can be transfected with a construct from which a target TGF-beta gene is expressed, thus preventing the need for endogenous TGF-beta expression. The level of target gene expression prior to and following contact with the candidate iRNA agent can be compared, e.g. on an mRNA or protein level. If it is determined that the amount of RNA or protein expressed from the target gene is lower following contact with the iRNA agent, then it can be concluded that the iRNA agent down-regulates target gene expression. The level of target TGF-beta mRNA or TGF-beta protein in the cell or tissue can be determined by any method desired. For example, the level of target RNA can be determined by Northern blot analysis, reverse transcription coupled with polymerase chain reaction (RT-PCR), bDNA analysis, or RNAse protection assay. The level of protein can be determined, for example, by Western blot analysis or immunofluorescence.

Stability Testing, Modification, and Retesting of iRNA Agents

A candidate iRNA agent can be evaluated with respect to stability, e.g., its susceptibility to cleavage by an endonuclease or exonuclease, such as when the iRNA agent is introduced into the body of a subject. Methods can be employed to identify sites that are susceptible to modification, particularly cleavage, e.g., cleavage by a component found in the body of a subject.

When sites susceptible to cleavage are identified, a further iRNA agent can be designed and/or synthesized wherein the potential cleavage site is made resistant to cleavage, e.g. by introduction of a 2'-modification on the site of cleavage, e.g. a 2'-O-methyl group. This further iRNA agent can be retested for stability, and this process may be iterated until an iRNA agent is found exhibiting the desired stability. Table 1 provides a variety of sequence modifications as exemplars, which are nevertheless not to be understood as limiting.

In Vivo Testing

An iRNA agent identified as being capable of inhibiting TGF-beta gene expression can be tested for functionality in vivo in an animal model (e.g., in a mammal, such as in mouse or rat) as shown in the examples. For example, the iRNA agent can be administered to an animal, and the iRNA agent evaluated with respect to its biodistribution, stability, and its ability to inhibit TGF-beta, e.g. lower TGF-beta protein or gene expression.

The iRNA agent can be administered directly to the target tissue, such as by injection, or the iRNA agent can be administered to the animal model in the same manner that it would be administered to a human, e.g. by inhalation, injection or infusion.

The iRNA agent can also be evaluated for its intracellular distribution. The evaluation can include determining whether the iRNA agent was taken up into the cell. The evaluation can also include determining the stability (e.g., the half-life) of the iRNA agent. Evaluation of an iRNA agent in vivo can be facilitated by use of an iRNA agent conjugated to a traceable marker (e.g., a fluorescent marker such as fluorescein; a radioactive label, such as $^{35}$S, $^{32}$P, $^{33}$P, or $^{3}$H; gold particles; or antigen particles for immunohistochemistry).

The iRNA agent can be evaluated with respect to its ability to down regulate TGF-beta gene expression. Levels of TGF-beta gene expression in vivo can be measured, for example, by in situ hybridization, or by the isolation of RNA from tissue prior to and following exposure to the iRNA agent. Where the animal needs to be sacrificed in order to harvest the tissue, an untreated control animal will serve for comparison. Target TGF-beta mRNA can be detected by any desired method, including but not limited to RT-PCR, Northern blot, branched-DNA assay, or RNAase protection assay. Alternatively, or additionally, TGF-beta gene expression can be monitored by performing Western blot analysis on tissue extracts treated with the iRNA agent.

iRNA Chemistry

Described herein are isolated iRNA agents, e.g., ds RNA agents, that mediate RNAi to inhibit expression of a TGF-beta gene.

RNA agents discussed herein include otherwise unmodified RNA as well as RNA which have been modified, e.g., to improve efficacy, and polymers of nucleoside surrogates. Unmodified RNA refers to a molecule in which the components of the nucleic acid, namely sugars, bases, and phosphate moieties, are the same or essentially the same as that which occur in nature, preferably as occur naturally in the human body. The art has referred to rare or unusual, but naturally occurring, RNAs as modified RNAs, see, e.g., Limbach et al., (1994) *Nucleic Acids Res.* 22: 2183-2196. Such rare or unusual RNAs, often termed modified RNAs (apparently because these are typically the result of a post-transcriptional modification) are within the term unmodified RNA, as used herein. Modified RNA as used herein refers to a molecule in which one or more of the components of the nucleic acid, namely sugars, bases, and phosphate moieties, are different from that which occurs in nature, preferably different from that which occurs in the human body. While they are referred to as modified "RNAs," they will of course, because of the modification, include molecules which are not RNAs. Nucleoside surrogates are molecules in which the ribophosphate backbone is replaced with a non-ribophosphate construct that allows the bases to be presented in the correct spatial relationship such that hybridization is substantially similar to what is seen with a ribophosphate backbone, e.g., non-charged mimics of the ribophosphate backbone. Examples of each of the above are discussed herein.

Modifications described herein can be incorporated into any double-stranded RNA and RNA-like molecule described herein, e.g., an iRNA agent. It may be desirable to modify one or both of the antisense and sense strands of an iRNA agent. As nucleic acids are polymers of subunits or monomers, many of the modifications described below occur at a position which is repeated within a nucleic acid, e.g., a modification of a base, or a phosphate moiety, or the non-linking O of a phosphate moiety. In some cases the modification will occur at all of the subject positions in the nucleic acid but in many, and in fact in most, cases it will not. By way of example, a modification may only occur at a 3' or 5' terminal position, may only occur in a terminal region, e.g. at a position on a terminal nucleotide or in the last 2, 3, 4, 5, or 10 nucleotides of a strand. A modification may occur in a double strand region, a single strand region, or in both. E.g., a phosphorothioate modification at a non-linking O position may only occur at one or both termini, may only occur in a terminal regions, e.g., at a position on a terminal nucleotide or in the last 2, 3, 4, 5, or 10 nucleotides of a strand, or may occur in double strand and single strand regions, particularly at termini. Similarly, a modification may occur on the sense strand, antisense strand, or both. In some cases, the sense and antisense strand will have the same modifications or the same class of modifications, but in other cases the sense and antisense strand will have different modifications, e.g., in some cases it may be desirable to modify only one strand, e.g. the sense strand.

Two prime objectives for the introduction of modifications into iRNA agents is their stabilization towards degradation in biological environments and the improvement of pharmacological properties, e.g. pharmacodynamic properties, which are further discussed below. Other suitable modifications to a sugar, base, or backbone of an iRNA agent are described in co-owned PCT Application No. PCT/US2004/01193, filed Jan. 16, 2004. An iRNA agent can include a non-naturally occurring base, such as the bases described in co-owned PCT Application No. PCT/US2004/011822, filed Apr. 16, 2004. An iRNA agent can include a non-naturally occurring sugar, such as a non-carbohydrate cyclic carrier molecule. Exemplary features of non-naturally occurring sugars for use in iRNA agents are described in co-owned PCT Application No. PCT/US2004/11829 filed Apr. 16, 2003.

An iRNA agent can include an internucleotide linkage (e.g., the chiral phosphorothioate linkage) useful for increasing nuclease resistance. In addition, or in the alternative, an iRNA agent can include a ribose mimic for increased nuclease resistance. Exemplary internucleotide linkages and ribose mimics for increased nuclease resistance are described in co-owned PCT Application No. PCT/US2004/07070 filed on Mar. 8, 2004.

An iRNA agent can include ligand-conjugated monomer subunits and monomers for oligonucleotide synthesis. Exemplary monomers are described in co-owned U.S. application Ser. No. 10/916,185, filed on Aug. 10, 2004.

An iRNA agent can have a ZXY structure, such as is described in co-owned PCT Application No. PCT/US2004/07070 filed on Mar. 8, 2004.

An iRNA agent can be complexed with an amphipathic moiety. Exemplary amphipathic moieties for use with iRNA agents are described in co-owned PCT Application No. PCT/US2004/07070 filed on Mar. 8, 2004.

In another embodiment, the iRNA agent can be complexed to a delivery agent that features a modular complex. The complex can include a carrier agent linked to one or more of (preferably two or more, more preferably all three of): (a) a condensing agent (e.g., an agent capable of attracting, e.g., binding, a nucleic acid, e.g., through ionic or electrostatic interactions); (b) a fusogenic agent (e.g., an agent capable of fusing and/or being transported through a cell membrane); and (c) a targeting group, e.g., a cell or tissue targeting agent, e.g., a lectin, glycoprotein, lipid or protein, e.g., an antibody, that binds to a specified cell type. iRNA agents complexed to a delivery agent are described in co-owned PCT Application No. PCT/US2004/07070 filed on Mar. 8, 2004.

An iRNA agent can have non-canonical pairings, such as between the sense and antisense sequences of the iRNA duplex. Exemplary features of non-canonical iRNA agents are described in co-owned PCT Application No. PCT/US2004/07070 filed on Mar. 8, 2004.

Enhanced Nuclease Resistance

An iRNA agent, e.g., an iRNA agent that targets TGF-beta, can have enhanced resistance to nucleases.

For increased nuclease resistance and/or binding affinity to the target, an iRNA agent, e.g., the sense and/or antisense strands of the iRNA agent, can include, for example, 2'-modified ribose units and/or phosphorothioate linkages. E.g., the 2' hydroxyl group (OH) can be modified or replaced with a number of different "oxy" or "deoxy" substituents.

Examples of "oxy"-2' hydroxyl group modifications include alkoxy or aryloxy (OR, e.g., R=H, alkyl, cycloalkyl, aryl, aralkyl, heteroaryl or sugar); polyethyleneglycols (PEG), $O(CH_2CH_2O)_nCH_2CH_2OR$; "locked" nucleic acids (LNA) in which the 2' hydroxyl is connected, e.g., by a methylene bridge, to the 4' carbon of the same ribose sugar; O-AMINE and aminoalkoxy, $O(CH_2)_n$AMINE, (e.g., AMINE=$NH_2$; alkylamino, dialkylamino, heterocyclyl amino, arylamino, diaryl amino, heteroaryl amino, or diheteroaryl amino, ethylene diamine, polyamino). It is noteworthy that oligonucleotides containing only the methoxyethyl group (MOE), ($OCH_2CH_2OCH_3$, a PEG derivative), exhibit nuclease stabilities comparable to those modified with the robust phosphorothioate modification.

"Deoxy" modifications include hydrogen (i.e. deoxyribose sugars, which are of particular relevance to the overhang portions of partially ds RNA); halo (e.g., fluoro); amino (e.g. $NH_2$; alkylamino, dialkylamino, heterocyclyl, arylamino, diaryl amino, heteroaryl amino, diheteroaryl amino, or amino acid); $NH(CH_2CH_2NH)_nCH_2CH_2$-AMINE (AMINE=$NH_2$; alkylamino, dialkylamino, heterocyclyl amino, arylamino, diaryl amino, heteroaryl amino, or diheteroaryl amino), —NHC(O)R(R=alkyl, cycloalkyl, aryl, aralkyl, heteroaryl or sugar), cyano; mercapto; alkyl-thio-alkyl; thioalkoxy; and alkyl, cycloalkyl, aryl, alkenyl and alkynyl, which may be optionally substituted with e.g., an amino functionality.

Preferred substituents are 2'-methoxyethyl, 2'-OCH3, 2'-O-allyl, 2'-C-allyl, and 2'-fluoro.

One way to increase resistance is to identify cleavage sites and modify such sites to inhibit cleavage, as described in co-owned U.S. Application No. 60/559,917, filed on May 4, 2004. For example, the dinucleotides 5'-ua-3', 5'-ca-3',5'-ug-3',5'-uu-3', or 5'-cc-3' can serve as cleavage sites. In certain embodiments, all the pyrimidines of an iRNA agent carry a 2'-modification in either the sense strand, the antisense strand, or both strands, and the iRNA agent therefore has enhanced resistance to endonucleases. Enhanced nuclease resistance can also be achieved by modifying the 5' nucleotide, resulting, for example, in at least one 5'-uridine-adenine-3' (5'-ua-3') dinucleotide wherein the uridine is a 2'-modified nucleotide; at least one 5'-cytidine-adenine-3' (5'-ca-3') dinucleotide, wherein the 5'-cytidine is a 2'-modified nucleotide; at least one 5'-uridine-guanine-3' (5'-ug-3') dinucleotide, wherein the 5'-uridine is a 2'-modified nucleotide; at least one 5'-uridine-uridine-3' (5'-uu-3') dinucleotide, wherein the 5'-uridine is a 2'-modified nucleotide; or at least one 5'-cytidine-cytidine-3' (5'-cc-3') dinucleotide, wherein the 5'-cytidine is a 2'-modified nucleotide, as described in co-owned International Application No. PCT/US2005/018931, filed on May 27, 2005. The iRNA agent can include at least 2, at least 3, at least 4 or at least 5 of such dinucleotides. In a particularly preferred embodiment, the 5' nucleotide in all occurrences of the sequence motifs 5'-ua-3' and 5'-ca-3' in either the sense strand, the antisense strand, or both strands is a modified nucleotide. Preferably, the 5' nucleotide in all occurrences of the sequence motifs 5'-ua-3',5'-ca-3' and 5'-ug-3' in either the sense strand, the antisense strand, or both strands is a modified nucleotide. More preferably, all pyrimidine nucleotides in the sense strand are modified nucleotides, and the 5' nucleotide in all occurrences of the sequence motifs 5'-ua-3' and 5'-ca-3' in the antisense strand are modified nucleotides, or where the antisense strand does comprise neither of a 5'-ua-3' and a 5'-ca-3' motif, in all occurrences of the sequence motif 5'-ug-3'. Preferably, sites particularly prone to nuclease degradation are first determined, e.g. by mass spectrometry of degradation products, and only those sites are sequentially modified until a desired level of stability is attained.

To maximize nuclease resistance, the 2' modifications can be used in combination with one or more phosphate linker modifications (e.g., phosphorothioate), as further described below. The so-called "chimeric" oligonucleotides are those that contain two or more different modifications. Preferably, phosphate linker modifications are located near the 3'- and/or 5'-end of either or both strands, or at or near sites particularly prone to degradative attack.

The inclusion of furanose sugars in the oligonucleotide backbone can also decrease endonucleolytic cleavage. An iRNA agent can be further modified by including a 3' cationic group, or by inverting the nucleoside at the 3'-terminus with a 3'-3' linkage. In another alternative, the 3'-terminus can be blocked with an aminoalkyl group, e.g., a 3' C5-aminoalkyl dT. Other 3' conjugates can inhibit 3'-5' exonucleolytic cleavage. While not being bound by theory, a 3' conjugate, such as naproxen or ibuprofen, may inhibit exonucleolytic cleavage by sterically blocking the exonuclease from binding to the 3'-end of oligonucleotide. Even small alkyl chains, aryl groups, or heterocyclic conjugates or modified sugars (D-ribose, deoxyribose, glucose etc.) can block 3'-5'-exonucleases.

Similarly, 5' conjugates can inhibit 5'-3' exonucleolytic cleavage. While not being bound by theory, a 5' conjugate, such as naproxen or ibuprofen, may inhibit exonucleolytic cleavage by sterically blocking the exonuclease from binding to the 5'-end of oligonucleotide. Even small alkyl chains, aryl groups, or heterocyclic conjugates or modified sugars (D-ribose, deoxyribose, glucose etc.) can block 3'-5'-exonucleases.

An iRNA agent can have increased resistance to nucleases when a duplexed iRNA agent includes a single-stranded nucleotide overhang on at least one end. In preferred embodiments, the nucleotide overhang includes 1 to 4, preferably 2 to 3, unpaired nucleotides. In a preferred embodiment, the unpaired nucleotide of the single-stranded overhang that is directly adjacent to the terminal nucleotide pair contains a purine base, and the terminal nucleotide pair is a G-C pair, or at least two of the last four complementary nucleotide pairs are G-C pairs. In further embodiments, the nucleotide overhang may have 1 or 2 unpaired nucleotides, and in an exemplary embodiment the nucleotide overhang is 5'-GC-3'. In preferred embodiments, the nucleotide overhang is on the 3'-end of the antisense strand. In one embodiment, the iRNA agent includes the motif 5'-CGC-3' on the 3'-end of the antisense strand, such that a 2-nt overhang 5'-GC-3' is formed.

Thus, an iRNA agent can include modifications so as to inhibit degradation, e.g., by nucleases, e.g., endonucleases or exonucleases, found in the body of a subject. These monomers are referred to herein as NRMs, or Nuclease Resistance promoting Monomers, the corresponding modifications as NRM modifications. In many cases these modifications will modulate other properties of the iRNA agent as well, e.g., the ability to interact with a protein, e.g., a transport protein, e.g., serum albumin, or a member of the RISC, or the ability of the first and second sequences to form a duplex with one another or to form a duplex with another sequence, e.g., a target molecule.

One or more different NRM modifications can be introduced into an iRNA agent or into a sequence of an iRNA agent. An NRM modification can be used more than once in a sequence or in an iRNA agent.

NRM modifications include some which can be placed only at the terminus and others which can go at any position. Some NRM modifications that can inhibit hybridization are preferably used only in terminal regions, and more preferably not at the cleavage site or in the cleavage region of a sequence which targets a subject sequence or gene, particularly on the antisense strand. They can be used anywhere in a sense strand, provided that sufficient hybridization between the two strands of the ds iRNA agent is maintained. In some embodiments it is desirable to put the NRM at the cleavage site or in the cleavage region of a sense strand, as it can minimize off-target silencing.

In most cases, the NRM modifications will be distributed differently depending on whether they are comprised on a sense or antisense strand. If on an antisense strand, modifications which interfere with or inhibit endonuclease cleavage should not be inserted in the region which is subject to RISC mediated cleavage, e.g., the cleavage site or the cleavage region (As described in Elbashir et al., 2001, Genes and Dev. 15: 188, hereby incorporated by reference). Cleavage of the target occurs about in the middle of a 20 or 21 nt antisense strand, or about 10 or 11 nucleotides upstream of the first nucleotide on the target mRNA which is complementary to the antisense strand. As used herein cleavage site refers to the nucleotides on either side of the site of cleavage, on the target mRNA or on the iRNA agent strand which hybridizes to it. Cleavage region means the nucleotides within 1, 2, or 3 nucleotides of the cleavage site, in either direction.

Such modifications can be introduced into the terminal regions, e.g., at the terminal position or with 2, 3, 4, or 5 positions of the terminus, of a sequence which targets or a sequence which does not target a sequence in the subject.

In a particular embodiment, the 5'-end of the antisense strand and the 3'-end of the sense strand are chemically linked via a hexaethylene glycol linker. In another embodiment, at least one nucleotide of the dsRNA comprises a phosphorothioate or phosphorodithioate groups. The chemical bond at the ends of the dsRNA is preferably formed by triple-helix bonds.

In certain embodiments, a chemical bond may be formed by means of one or several bonding groups, wherein such bonding groups are preferably poly-(oxyphosphinicooxy-1, 3-propandiol)- and/or polyethylene glycol chains. In other embodiments, a chemical bond may also be formed by means of purine analogs introduced into the double-stranded structure instead of purines. In further embodiments, a chemical bond may be formed by azabenzene units introduced into the double-stranded structure. In still further embodiments, a chemical bond may be formed by branched nucleotide analogs instead of nucleotides introduced into the double-stranded structure. In certain embodiments, a chemical bond may be induced by ultraviolet light.

Teachings regarding the synthesis of particular modified oligonucleotides may be found in the following U.S. patents: U.S. Pat. Nos. 5,138,045 and 5,218,105, drawn to polyamine conjugated oligonucleotides; U.S. Pat. No. 5,212,295, drawn to monomers for the preparation of oligonucleotides having chiral phosphorus linkages; U.S. Pat. Nos. 5,378,825 and 5,541,307, drawn to oligonucleotides having modified backbones; U.S. Pat. No. 5,386,023, drawn to backbone-modified oligonucleotides and the preparation thereof through reductive coupling; U.S. Pat. No. 5,457,191, drawn to modified nucleobases based on the 3-deazapurine ring system and methods of synthesis thereof; U.S. Pat. No. 5,459,255, drawn to modified nucleobases based on N-2 substituted purines; U.S. Pat. No. 5,521,302, drawn to processes for preparing oligonucleotides having chiral phosphorus linkages; U.S. Pat. No. 5,539,082, drawn to peptide nucleic acids; U.S. Pat. No. 5,554,746, drawn to oligonucleotides having β-lactam backbones; U.S. Pat. No. 5,571,902, drawn to methods and materials for the synthesis of oligonucleotides; U.S. Pat. No. 5,578,718, drawn to nucleosides having alkylthio groups, wherein such groups may be used as linkers to other moieties attached at any of a variety of positions of the nucleoside; U.S. Pat. Nos. 5,587,361 and 5,599,797, drawn to oligonucleotides having phosphorothioate linkages of high chiral purity; U.S. Pat. No. 5,506,351, drawn to processes for the preparation of 2'-O-alkyl guanosine and related compounds, including 2,6-diaminopurine compounds; U.S. Pat. No. 5,587,469, drawn to oligonucleotides having N-2 substituted purines; U.S. Pat. No. 5,587,470, drawn to oligonucleotides having 3-deazapurines; U.S. Pat. No. 5,223,168, and U.S. Pat. No. 5,608,046, both drawn to conjugated 4'-desmethyl nucleoside analogs; U.S. Pat. Nos. 5,602,240, and 5,610,289, drawn to backbone-modified oligonucleotide analogs; U.S. Pat. Nos. 6,262,241, and 5,459,255, drawn to, inter alia, methods of synthesizing 2'-fluoro-oligonucleotides.

In some preferred embodiments, functionalized nucleoside sequences of the invention possessing an amino group at the 5'-terminus are prepared using a DNA synthesizer, and then reacted with an active ester derivative of a selected ligand. Active ester derivatives are well known to those skilled in the art. Representative active esters include N-hydrosuccinimide esters, tetrafluorophenolic esters, pentafluorophenolic esters and pentachlorophenolic esters. The reaction of the amino group and the active ester produces an oligonucleotide in which the selected ligand is attached to the 5'-position through a linking group. The amino group at the 5'-terminus can be prepared utilizing a 5'-Amino-Modifier C6 reagent. In a preferred embodiment, ligand molecules may be conjugated to oligonucleotides at the 5'-position by the use of a ligand-nucleoside phosphoramidite wherein the ligand is linked to the 5'-hydroxy group directly or indirectly via a linker. Such ligand-nucleoside phosphoramidites are typically used at the end of an automated synthesis procedure to provide a ligand-conjugated oligonucleotide bearing the ligand at the 5'-terminus.

In many cases, protecting groups are used during the preparation of the compounds of the invention. As used herein, the term "protected" means that the indicated moiety has a protecting group appended thereon. In some preferred embodiments of the invention, compounds contain one or more protecting groups. A wide variety of protecting groups can be employed in the methods of the invention. In general, protecting groups render chemical functionalities inert to specific reaction conditions, and can be appended to and removed from such functionalities in a molecule without substantially damaging the remainder of the molecule.

Representative hydroxyl protecting groups, for example, are disclosed by Beaucage et al. (*Tetrahedron*, 1992, 48:2223-23.11). Further hydroxyl protecting groups, as well as other representative protecting groups, are disclosed in Greene and Wuts, *Protective Groups in Organic Synthesis*, Chapter 2, 2d ed., John Wiley & Sons, New York, 1991, and *Oligonucleotides And Analogues A Practical Approach*, Ekstein, F. Ed., IRL Press, N.Y, 1991.

Examples of hydroxyl protecting groups include, but are not limited to, t-butyl, t-butoxymethyl, methoxymethyl, tetrahydropyranyl, 1-ethoxyethyl, 1-(2-chloroethoxy)ethyl, 2-trimethylsilylethyl, p-chlorophenyl, 2,4-dinitrophenyl, benzyl, 2,6-dichlorobenzyl, diphenylmethyl, p,p'-dinitrobenzhydryl, p-nitrobenzyl, triphenylmethyl, trimethylsilyl, triethylsilyl, t-butyldimethylsilyl, t-butyldiphenylsilyl, triphenylsilyl, benzoylformate, acetate, chloroacetate, trichloroacetate, trifluoroacetate, pivaloate, benzoate, p-phenylbenzoate, 9-fluorenylmethyl carbonate, mesylate and tosylate.

Amino-protecting groups stable to acid treatment are selectively removed with base treatment, and are used to make reactive amino groups selectively available for substitution. Examples of such groups are the Fmoc (E. Atherton and R. C. Sheppard in *The Peptides*, S. Udenfriend, J. Meienhofer, Eds., Academic Press, Orlando, 1987, volume 9, p. 1) and various substituted sulfonylethyl carbamates exemplified by the Nsc group (Samukov et al., *Tetrahedron Lett.*, 1994, 35:7821; Verhart and Tesser, *Rec. Trav. Chim. Pays-Bas*, 1987, 107:621).

Additional amino-protecting groups include, but are not limited to, carbamate protecting groups, such as 2-trimethylsilylethoxycarbonyl (Teoc), 1-methyl-1-(4-biphenylyl) ethoxycarbonyl (Bpoc), t-butoxycarbonyl (BOC), allyloxycarbonyl (Alloc), 9-fluorenylmethyloxycarbonyl (Fmoc), and benzyloxycarbonyl (Cbz); amide protecting groups, such as formyl, acetyl, trihaloacetyl, benzoyl, and nitrophenylacetyl; sulfonamide protecting groups, such as 2-nitrobenzenesulfonyl; and imine and cyclic imide protecting groups, such as phthalimido and dithiasuccinoyl. Equivalents of these amino-protecting groups are also encompassed by the compounds and methods of the invention.

Many solid supports are commercially available and one of ordinary skill in the art can readily select a solid support to be used in the solid-phase synthesis steps. In certain embodiments, a universal support is used. A universal support allows for preparation of oligonucleotides having unusual or modified nucleotides located at the 3'-terminus of the oligonucleotide. Universal Support 500 and Universal Support II are universal supports that are commercially available from Glen Research, 22825 Davis Drive, Sterling, Va. For further details about universal supports see Scott et al., *Innovations and Perspectives in solid-phase Synthesis*, 3rd *International Symposium*, 1994, Ed. Roger Epton, Mayflower Worldwide, 115-124]; Azhayev, A. V. *Tetrahedron* 1999, 55, 787-800; and Azhayev and Antopolsky *Tetrahedron* 2001, 57, 4977-4986. In addition, it has been reported that the oligonucleotide can be cleaved from the universal support under milder reaction conditions when oligonucleotide is bonded to the solid support via a syn-1,2-acetoxyphosphate group which more readily undergoes basic hydrolysis. See Guzaev, A. I.; Manoharan, M. *J. Am. Chem. Soc.* 2003, 125, 2380.

Ligand Conjugates

The properties of an iRNA agent, including its pharmacological properties, can be influenced and tailored, for example, by the introduction of ligands, e.g. tethered ligands.

A wide variety of entities, e.g., ligands, can be tethered to an iRNA agent, e.g., to the carrier of a ligand-conjugated monomer subunit. Examples are described below in the context of a ligand-conjugated monomer subunit but that is only preferred, entities can be coupled at other points to an iRNA agent.

Preferred moieties are ligands, which are coupled, preferably covalently, either directly or indirectly via an intervening tether, to the carrier. In preferred embodiments, the ligand is attached to the carrier via an intervening tether. The ligand or tethered ligand may be present on the ligand-conjugated monomer when the ligand-conjugated monomer is incorporated into the growing strand. In some embodiments, the ligand may be incorporated into a "precursor" ligand-conjugated monomer subunit after a "precursor" ligand-conjugated monomer subunit has been incorporated into the growing strand. For example, a monomer having, e.g., an amino-terminated tether, e.g., TAP—$(CH_2)_n NH_2$ may be incorporated into a growing sense or antisense strand. In a subsequent operation, i.e., after incorporation of the precursor monomer subunit into the strand, a ligand having an electrophilic group, e.g., a pentafluorophenyl ester or aldehyde group, can subsequently be attached to the precursor ligand-conjugated monomer by coupling the electrophilic group of the ligand with the terminal nucleophilic group of the precursor ligand-conjugated monomer subunit tether.

In preferred embodiments, a ligand alters the distribution, targeting or lifetime of an iRNA agent into which it is incorporated. In preferred embodiments a ligand provides an enhanced affinity for a selected target, e.g., molecule, cell or cell type, compartment, e.g., a cellular or organ compartment, tissue, organ or region of the body, as, e.g., compared to a species absent such a ligand.

Preferred ligands can improve transport, hybridization, and specificity properties and may also improve nuclease resistance of the resultant natural or modified oligoribonucleotide, or a polymeric molecule comprising any combination of monomers described herein and/or natural or modified ribonucleotides.

Ligands in general can include therapeutic modifiers, e.g., for enhancing uptake; diagnostic compounds or reporter groups e.g., for monitoring distribution; cross-linking agents; nuclease-resistance conferring moieties; and natural or unusual nucleobases. General examples include lipophilic moleculeses, lipids, lectins, steroids (e.g., uvaol, hecigenin, diosgenin), terpenes (e.g., triterpenes, e.g., sarsasapogenin, Friedelin, epifriedelanol derivatized lithocholic acid), vitamins, carbohydrates (e.g., a dextran, pullulan, chitin, chitosan, inulin, cyclodextrin or hyaluronic acid), proteins, protein binding agents, integrin targeting molecules, polycationics, peptides, polyamines, and peptide mimics.

The ligand may be a naturally occurring or recombinant or synthetic molecule, such as a synthetic polymer, e.g., a synthetic polyamino acid. Examples of polyamino acids include polyamino acid is a polylysine (PLL), poly L-aspartic acid, poly L-glutamic acid, styrene-maleic acid anhydride copolymer, poly(L-lactide-co-glycolied) copolymer, divinyl ether-maleic anhydride copolymer, N-(2-hydroxypropyl)methacrylamide copolymer (HMPA), polyethylene glycol (PEG), polyvinyl alcohol (PVA), polyurethane, poly(2-ethylacrylic acid), N-isopropylacrylamide polymers, or polyphosphazine. Example of polyamines include: polyethylenimine, polylysine (PLL), spermine, spermidine, polyamine, pseudopeptide-polyamine, peptidomimetic polyamine, dendrimer polyamine, arginine, amidine, protamine, cationic moieties, e.g., cationic lipid, cationic porphyrin, quaternary salt of a polyamine, or an alpha helical peptide.

Ligands can also include targeting groups, e.g., a cell or tissue targeting agent, e.g., a thyrotropin, melanotropin, surfactant protein A, Mucin carbohydrate, a glycosylated polyaminoacid, transferrin, bisphosphonate, polyglutamate, polyaspartate, or an RGD peptide or RGD peptide mimetic.

Ligands can be proteins, e.g., glycoproteins, lipoproteins, e.g. low density lipoprotein (LDL), or albumins, e.g. human serum albumin (HSA), or peptides, e.g., molecules having a specific affinity for a co-ligand, or antibodies e.g., an antibody, that binds to a specified cell type such as a cancer cell, endothelial cell, or bone cell. Ligands may also include hormones and hormone receptors. They can also include non-peptidic species, such as cofactors, multivalent lactose, multivalent galactose, N-acetyl-galactosamine, N-acetylglucosamine, multivalent mannose, or multivalent fucose. The ligand can be, for example, a lipopolysaccharide, an activator of p38 MAP kinase, or an activator of NF-κB.

The ligand can be a substance, e.g, a drug, which can increase the uptake of the iRNA agent into the cell, for example, by disrupting the cell's cytoskeleton, e.g., by disrupting the cell's microtubules, microfilaments, and/or intermediate filaments. The drug can be, for example, taxon, vincristine, vinblastine, cytochalasin, nocodazole, japlakinolide, latrunculin A, phalloidin, swinholide A, indanocine, or myoservin.

In one aspect, the ligand is a lipid or lipid-based molecule. Such a lipid or lipid-based molecule preferably binds a serum protein, e.g., human serum albumin (HSA). An HSA binding ligand allows for distribution of the conjugate to a target tissue, e.g., liver tissue, including parenchymal cells of the liver. Other molecules that can bind HSA can also be used as ligands. For example, neproxin or aspirin can be used. A lipid or lipid-based ligand can (a) increase resistance to degradation of the conjugate, (b) increase targeting or transport into a target cell or cell membrane, and/or (c) can be used to adjust binding to a serum protein, e.g., HSA.

A lipid based ligand can be used to modulate, e.g., control the binding of the conjugate to a target tissue. For example, a lipid or lipid-based ligand that binds to HSA more strongly will be less likely to be targeted to the kidney and therefore less likely to be cleared from the body. A lipid or lipid-based ligand that binds to HSA less strongly can be used to target the conjugate to the kidney.

In a preferred embodiment, the lipid based ligand binds HSA. Preferably, it binds HSA with a sufficient affinity such that the conjugate will be preferably distributed to a non-kidney tissue. However, it is preferred that the affinity not be so strong that the HSA-ligand binding cannot be reversed.

In another aspect, the ligand is a moiety, e.g., a vitamin or nutrient, which is taken up by a target cell, e.g., a proliferating cell. These are particularly useful for treating disorders characterized by unwanted cell proliferation, e.g., of the malignant or non-malignant type, e.g., cancer cells. Exemplary vitamins include vitamin A, E, and K. Other exemplary vitamins include the B vitamins, e.g., folic acid, B12, riboflavin, biotin, pyridoxal or other vitamins or nutrients taken up by cancer cells.

In another aspect, the ligand is a cell-permeation agent, preferably a helical cell-permeation agent. Preferably, the agent is amphipathic. An exemplary agent is a peptide such as that or antennapedia. If the agent is a peptide, it can be modified, including a peptidylmimetic, invertomers, non-peptide or pseudo-peptide linkages, and use of D-amino acids. The helical agent is preferably an alpha-helical agent, which preferably has a lipophilic and a lipophobic phase.

Backbone Modifications

Specific examples of preferred modified oligonucleotides envisioned for use in the ligand-conjugated oligonucleotides of the invention include oligonucleotides containing modified backbones or non-natural internucleoside linkages. As defined here, oligonucleotides having modified backbones or internucleoside linkages include those that retain a phosphorus atom in the backbone and those that do not have a phosphorus atom in the backbone. For the purposes of the invention, modified oligonucleotides that do not have a phosphorus atom in their intersugar backbone can also be considered to be oligonucleosides.

Specific oligonucleotide chemical modifications are described below. It is not necessary for all positions in a given compound to be uniformly modified. Conversely, more than one modifications may be incorporated in a single dsRNA compound or even in a single nucleotide thereof.

Preferred modified internucleoside linkages or backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, salts and free-acid forms are also included.

Representative United States Patents relating to the preparation of the above phosphorus-atom-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,625,050; and 5,697,248, each of which is herein incorporated by reference.

Preferred modified internucleoside linkages or backbones that do not include a phosphorus atom therein (i.e., oligonucleosides) have backbones that are formed by short chain alkyl or cycloalkyl intersugar linkages, mixed heteroatom and alkyl or cycloalkyl intersugar linkages, or one or more short chain heteroatomic or heterocyclic intersugar linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, 0, S and $CH_2$ component parts.

Representative United States patents relating to the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference.

5'-Terminal Modifications

In preferred embodiments, iRNA agents are 5' phosphorylated or include a phosphoryl analog at the 5' prime terminus, e.g. 5' prime terminus of the antisense strand. 5'-phosphate modifications of the antisense strand include those which are compatible with RISC mediated gene silencing. Suitable modifications include: 5'-monophosphate ((HO)2(O)P—O—5'); 5'-diphosphate ((HO)2(O)P—O—P(HO)(O)—O-5'); 5'-triphosphate ((HO)2(O)P—O—(HO)(O)P—O—P(HO)(O)—O-5'); 5'-guanosine cap (7-methylated or non-methylated) (7m-G-O-5'-(HO)(O)P—O—(HO)(O)P—O—P(HO)(O)—O-5'); 5'-adenosine cap (Appp), and any modified or unmodified nucleotide cap structure. Other suitable 5'-phosphate modifications will be known to the skilled person.

The sense strand can be modified in order to inactivate the sense strand and prevent formation of an active RISC, thereby potentially reducing off-target effects. This can be accomplished by a modification which prevents 5'-phosphorylation of the sense strand, e.g., by modification with a 5'-O-methyl ribonucleotide (see Nykänen et al., (2001) ATP requirements and small interfering RNA structure in the RNA interference pathway. Cell 107, 309-321.) Other modifications which prevent phosphorylation can also be used, e.g., simply substituting the 5'-OH by H rather than O-Me. Alternatively, a large bulky group may be added to the 5'-phosphate turning it into a phosphodiester linkage.

Disorders and Diseases Associated with Undesired TGF-Beta Signaling

Diseases that can be treated in accordance with the present invention include, without limitation, kidney disorders associated with undesired TGF-beta signaling and excessive fibrosis and/or sclerosis, such as glomerulonephritis (GN) of all etiologies, e.g., mesangial proliferative GN, immune GN, and crescentic GN; diabetic nephropathy; renal interstitial fibrosis and all causes of renal interstitial fibrosis, including hypertension; renal fibrosis resulting from complications of drug exposure, including cyclosporin treatment of transplant recipients, e.g. cyclosporin treatment; HIV-associated nephropathy, transplant necropathy. The invention further includes the treatment of hepatic diseases associated with excessive scarring and progressive sclerosis, including cirrhosis due to all etiologies, disorders of the biliary tree, and hepatic dysfunction attributable to infections such as infection with hepatitis virus or parasites; pulmonary fibrosis and symptoms associates with pulmonary fibrosis with consequential loss of gas exchange or ability to efficiently move air into and out of the lungs, including adult respiratory distress syndrome (ARDS), chronic obstructive pulmonary disease (COPD); idiopathic pulmonary fibrosis (IPF), acute lung injury (ALI), or pulmonary fibrosis due to infectious or toxic agents such as smoke, chemicals, allergens, or autoimmune diseases, such as systemic lupus erythematosus and scleroderma, chemical contact, or allergies. Fibroproliferative diseases targeted by the agents, pharmaceutical compositions, and treatment methods herein further include cardiovascular diseases, such as congestive heart failure, dilated cardiomyopathy, myocarditis, or vascular stenosis associated with atherosclerosis, angioplasty treatment, or surgical incisions or mechanical trauma. The invention also includes the treatment of all collagen vascular disorders of a chronic or persistent nature including progressive systemic sclerosis, polymyositis, scleroderma, dermatomyositis, fascists, or Raynaud's syndrome, or arthritic conditions such as rheumatoid arthritis; eye diseases associated with fibroproliferative states, including proliferative vitreoretinopathy of any etiology or fibrosis associated with ocular surgery such as treatment of glaucoma, retinal reattachment, cataract extraction, or drainage procedures of any kind; excessive or hypertrophic scar formation in the dermis occurring during wound healing resulting from trauma or surgical wounds.

While the above list is not meant in any way limiting, the treatment of all the above disorders and diseases are contemplated by the invention.

Delivery of iRNA Agents to Tissues and Cells

Formulation

For ease of exposition, the formulations, compositions, and methods in this section are discussed largely with regard to unmodified iRNA agents. It should be understood, however, that these formulations, compositions, and methods can be practiced with other iRNA agents, e.g., modified iRNA agents, and such practice is within the invention.

The term "therapeutically effective amount" is the amount present in the composition that is needed to provide the desired level of drug in the subject to be treated to give the anticipated physiological response.

The term "physiologically effective amount" is that amount delivered to a subject to give the desired palliative or curative effect.

The term "co-administration" refers to administering to a subject two or more agents, and in particular two or more iRNA agents. The agents can be contained in a single pharmaceutical composition and be administered at the same time, or the agents can be contained in separate formulation and administered serially to a subject. So long as the two agents can be detected in the subject at the same time, the two agents are said to be co-administered.

In the present methods, the iRNA agent can be administered to the subject either as naked iRNA agent, in conjunction with a delivery reagent, or as a recombinant plasmid or viral vector which expresses the iRNA agent. Preferably, the iRNA agent is administered as naked iRNA.

The iRNA agents described herein can be formulated for administration to a subject, preferably for administration locally to a site of fibrosis or sclerosis, or parenterally, e.g. via injection.

A formulated iRNA agent composition can assume a variety of states. In some examples, the composition is at least partially crystalline, uniformly crystalline, and/or anhydrous (e.g., less than 80, 50, 30, 20, or 10% water). In other examples, the composition is amorphous, such as a wax. In another example, the iRNA agent is in an aqueous phase, e.g., in a solution that includes water, this form being the preferred form for administration via inhalation. The aqueous phase may contain other solvents or excipients, e.g. ethanol.

The aqueous phase or the crystalline compositions can be incorporated into a delivery vehicle, e.g., a liposome (particularly for the aqueous phase), or a particle (e.g., a microparticle as can be appropriate for a crystalline composition). Generally, the iRNA agent composition is formulated in a manner that is compatible with the intended method of administration.

Formulations for direct injection and parenteral administration are well known in the art. Such formulation may include sterile aqueous solutions which may also contain buffers, diluents and other suitable additives. For intravenous use, the total concentration of solutes should be controlled to render the preparation isotonic.

The nucleic acid molecules of the present invention can also be co-administered to a subject in combination with other therapeutic compounds to increase the overall therapeutic effect. The use of multiple compounds to treat an indication can increase the beneficial effects while reducing the presence of side effects.

An iRNA agent preparation can be formulated in combination with another agent, e.g., another therapeutic agent or an agent that stabilizes an iRNA agent, e.g., a protein that complexes with the iRNA agent to form an iRNP. Still other agents include chelators, e.g., EDTA (e.g., to remove divalent cations such as $Mg^{2+}$), salts, RNAse inhibitors (e.g., a broad specificity RNAse inhibitor such as RNAsin) and so forth.

In one embodiment, the iRNA agent preparation includes another iRNA agent, e.g., a second iRNA agent that can mediate RNAi with respect to a second gene. Still other preparations can include at least three, five, ten, twenty, fifty, or a hundred or more different iRNA species. In some embodiments, the agents are directed to the same gene but different target sequences. In another embodiment, each iRNA agent is directed to a different gene, e.g. TGF-beta.

An iRNA agent can be incorporated into pharmaceutical compositions suitable for administration. For example, compositions can include one or more iRNA agents and a pharmaceutically acceptable carrier.

The iRNA agents featured by the invention are preferably formulated as pharmaceutical compositions prior to administering to a subject, according to techniques known in the art. Pharmaceutical compositions of the present invention are characterized as being at least sterile and pyrogen-free. As used herein, "pharmaceutical formulations" include formulations for human and veterinary use. Methods for preparing pharmaceutical compositions of the invention are within the skill in the art, for example as described in *Remington's Pharmaceutical Science,* 18th ed., Mack Publishing Company, Easton, Pa. (1990), and *The Science and Practice of Pharmacy,* 2003, Gennaro et al., the entire disclosures of which are herein incorporated by reference.

The present pharmaceutical formulations comprise an iRNA agent of the invention (e.g., 0.1 to 90% by weight), or a physiologically acceptable salt thereof, mixed with a physiologically acceptable carrier medium. Preferred physiologically acceptable carrier media are water, buffered water, normal saline, 0.4% saline, 0.3% glycine, hyaluronic acid and the like.

Pharmaceutical compositions of the invention can also comprise conventional pharmaceutical excipients and/or additives. Suitable pharmaceutical excipients include stabilizers, antioxidants, osmolality adjusting agents, buffers, and pH adjusting agents. Suitable additives include physiologically biocompatible buffers (e.g., tromethamine hydrochloride), additions of chelants (such as, for example, DTPA or DTPA-bisamide) or calcium chelate complexes (as for example calcium DTPA, CaNaDTPA-bisamide), or, optionally, additions of calcium or sodium salts (for example, calcium chloride, calcium ascorbate, calcium gluconate or calcium lactate). Pharmaceutical compositions of the invention can be packaged for use in liquid form, or can be lyophilized.

For solid compositions, conventional non-toxic solid carriers can be used; for example, pharmaceutical grades of mannitol, lactose, starch, magnesium stearate, sodium saccharin, talcum, cellulose, glucose, sucrose, magnesium carbonate, and the like.

For example, a solid pharmaceutical composition for oral administration can comprise any of the carriers and excipients listed above and 10-95%, preferably 25%-75%, of one or more iRNA agents of the invention.

By "pharmaceutically acceptable formulation" is meant a composition or formulation that allows for the effective distribution of the nucleic acid molecules of the instant invention in the physical location most suitable for their desired activity. Non-limiting examples of agents suitable for formulation with the nucleic acid molecules of the instant invention include: P-glycoprotein inhibitors (such as PluronicP85), which can enhance entry of drugs into the CNS (Jolliet-Riant and Tillement, *Fundam. Clin. Pharmacol.* 13:16, 1999); biodegradable polymers, such as poly (DL-lactide-coglycolide) microspheres for sustained release delivery. Other non-limiting examples of delivery strategies for the nucleic acid molecules of the instant invention include material described in Boado et al., *J. Pharm. Sci.* 87:1308, 1998; Tyler et al., *FEBS Lett.* 421:280, 1999; Pardridge et al., *PNAS USA.* 92:5592, 1995; Boado, *Adv. Drug Delivery Rev.* 15:73, 1995; Aldrian-Herrada et al., *Nucleic Acids Res.* 26:4910, 1998; and Tyler et al., *PNAS USA* 96:7053, 1999.

The invention also features the use of the composition comprising surface-modified liposomes containing poly (ethylene glycol) lipids (PEG-modified, or long-circulating liposomes or stealth liposomes). These formulations offer a method for increasing the accumulation of drugs in target tissues. This class of drug carriers resists opsonization and elimination by the mononuclear phagocytic system (WPS or RES), thereby enabling longer blood circulation times and enhanced tissue exposure for the encapsulated drug (Lasic et al., *Chem. Rev.* 95:2601, 1995; Ishiwata et al., *Chem. Phare. Bull.* 43:1005, 1995).

Such liposomes have been shown to accumulate selectively in tumors, presumably by extravasation and capture in the neovascularized target tissues (Lasic et al., *Science* 267:1275, 1995; Oku et al., *Biochim. Biophys. Acta* 1238:86, 1995). The long-circulating liposomes enhance the pharmacokinetics and pharmacodynamics of DNA and RNA, particularly compared to conventional cationic liposomes which are known to accumulate in tissues of the MPS (Liu et al., *J. Biol. Chem.* 42:24864, 1995; Choi et al., International PCT Publication No. WO 96/10391; Ansell et al., International PCT Publication No. WO 96/10390; Holland et al., International PCT Publication No. WO 96/10392). Long-circulating liposomes are also likely to protect drugs from nuclease degradation to a greater extent compared to cationic liposomes, based on their ability to avoid accumulation in metabolically aggressive MPS tissues such as the liver and spleen.

Alternatively, certain iRNA agents of the instant invention can be expressed within cells from eukaryotic promoters (e.g., Izant and Weintraub, *Science* 229:345, 1985; McGarry and Lindquist, *Proc. Natl. Acad. Sci. USA* 83:399, 1986; Scanlon et al., *Proc. Natl. Acad. Sci. USA* 88:10591, 1991; Kashani-Sabet et al., *Antisense Res. Dev.* 2:3, 1992; Dropulic et al., *J. Virol.* 66:1432, 1992; Weerasinghe et al., *J. Virol.* 65:5531, 1991; Ojwang et al., *Proc. Natl. Acad. Sci. USA* 89:10802, 1992; Chen et al., *Nucleic Acids Res.* 20:4581, 1992; Sarver et al., *Science* 247:1222, 1990; Thompson et al., *Nucleic Acids Res.* 23:2259, 1995; Good et al., *Gene Therapy* 4:45, 1997). Those skilled in the art realize that any nucleic acid can be expressed in eukaryotic cells from the appropriate DNA/RNA vector. The activity of such nucleic acids can be augmented by their release from the primary transcript by a enzymatic nucleic acid (Draper et al., PCT WO 93/23569, and Sullivan et al., PCT WO 94/02595; Ohkawa et al., *Nucleic Acids Symp. Ser.* 27:156, 1992; Taira et al., *Nucleic Acids Res.* 19:5125, 1991; Ventura et al., *Nucleic Acids Res.* 21:3249, 1993; Chowrira et al., *J. Biol. Chem.* 269:25856, 1994).

In another aspect of the invention, RNA molecules of the present invention can be expressed from transcription units (see for example Couture et al., *Trends in Genetics* 12:510, 1996) inserted into DNA or RNA vectors. The recombinant vectors can be DNA plasmids or viral vectors. iRNA agent-expressing viral vectors can be constructed based on, but not limited to, adeno-associated virus, retrovirus, adenovirus, or alphavirus. In another embodiment, pol III based constructs are used to express nucleic acid molecules of the invention (see for example Thompson, U.S. Pats. Nos. 5,902,880 and 6,146,886). The recombinant vectors capable of expressing the iRNA agents can be delivered as described above, and persist in target cells. Alternatively, viral vectors can be used that provide for transient expression of nucleic acid molecules. Such vectors can be repeatedly administered as necessary. Once expressed, the iRNA agent interacts with the target mRNA and generates an RNAi response. Delivery of iRNA agent-expressing vectors can be systemic, such as by intravenous or intramuscular administration, by administration to target cells ex-planted from a subject followed by reintroduction into the subject, or by any other means that would allow for introduction into the desired target cell (for a review see Couture et al., *Trends in Genetics* 12:510, 1996).

The present invention also includes compositions prepared for storage or administration that include a pharmaceutically effective amount of the desired compounds in a pharmaceutically acceptable carrier. The term "pharmaceutically acceptable carrier" means that the carrier can be taken into the subject with no significant adverse toxicological effects on the subject. Acceptable carriers for therapeutic use are well known in the pharmaceutical art, and are described, for example, in *Remington's Pharmaceutical Sciences*, Mack Publishing Co. (A. R. Gennaro edit. 1985), hereby incorporated by reference herein. The term is intended to include any and all solvents, dispersion media, coatings, preservatives, e.g. antibacterial and antifungal agents, isotonic and absorption delaying agents, stabilizers, antioxidants, suspending agents, dyes, flavoring agents, and the like, compatible with pharmaceutical administration. Except insofar as any conventional media or agent is incompatible with the active compound, use thereof in the compositions is contemplated. Supplementary active compounds can also be incorporated into the compositions.

The types of pharmaceutical excipients that are useful as carrier include stabilizers such as human serum albumin (HSA), bulking agents such as carbohydrates, amino acids and polypeptides; pH adjusters or buffers; salts such as sodium chloride; and the like. These carriers may be in a crystalline or amorphous form or may be a mixture of the two.

Preservatives include, for example, without limitation, sodium benzoate, sorbic acid and esters of p-hydroxybenzoic acid.

Bulking agents that are particularly valuable include compatible carbohydrates, polypeptides, amino acids or combinations thereof. Suitable carbohydrates include monosaccharides such as galactose, D-mannose, sorbose, and the like; disaccharides, such as lactose, trehalose, and the like; cyclodextrins, such as 2-hydroxypropyl-beta-cyclodextrin; and polysaccharides, such as raffinose, maltodextrins, dextrans, and the like; alditols, such as mannitol, xylitol, and the like. A preferred group of carbohydrates includes lactose, threhalose, raffinose maltodextrins, and mannitol. Suitable polypeptides include aspartame. Amino acids include alanine and glycine, with glycine being preferred.

Suitable pH adjusters or buffers include organic salts prepared from organic acids and bases, such as sodium citrate, sodium ascorbate, and the like; sodium citrate is preferred.

Treatment Methods and Delivery

Administration of the iRNA Agents A patient who has been diagnosed with a disorder characterized by undesired TGF-beta signaling can be treated by administration of an iRNA agent described herein to block the negative effects of TGF-beta, thereby alleviating the symptoms associated with undesired TGF-beta signaling. For example, the iRNA agent can alleviate symptoms associated with a disease of the lung, such as a fibrotic disorder. In other examples, the iRNA agent can be administered to treat a patient who has a fibrotic or sclerotic disease of the kidney or liver; a fibroproliferative cardiovascular disease; a collagen vascular disorder; or any other fibroproliferative disorder associated with undesired TGF-beta signaling.

A composition that includes an iRNA agent of the present invention, e.g., an iRNA agent that targets TGF-beta, can be delivered to a subject by a variety of routes, depending upon whether local or systemic treatment is desired and upon the area to be treated. In general, the delivery of the iRNA agents of the present invention is done to achieve delivery into the subject to the site of undesired TGF-beta signaling. The preferred means of administering the iRNA agents of the present invention is through either a local administration to the site of fibrosis or sclerosis, such as the lung, e.g. by inhalation, or systemically through enteral or parenteral administration.

Suitable enteral administration routes include oral delivery.

Suitable parenteral administration routes include intravascular administration (e.g., intravenous bolus injection, intravenous infusion, intra-arterial bolus injection, intra-arterial infusion and catheter instillation into the vasculature); peri- and intra-tissue injection; subcutaneous injection, deposition including subcutaneous infusion (such as by osmotic pumps), or transdermal application; intraperitoneal or intramuscular injection; intrathecal or intraventricular administration; intraocular, intraotic, intranasal, or intrapulmonary administration; or direct application to the area at or near the site of undesired TGF-beta signaling, for example by a catheter or other placement device (e.g., a pellet or implant comprising a porous, non-porous, or gelatinous material). It is preferred that injections or infusions of the iRNA agent be given at or near the site of undesired TGF-beta signaling.

The anti-TGF-beta iRNA agents can be administered systemically, e.g., orally or by intramuscular injection or by intravenous injection, in admixture with a pharmaceutically acceptable carrier adapted for the route of administration. Methods for the delivery of nucleic acid molecules are described in Akhtar et al., *Trends in Cell Bio.* 2:139, 1992; *Delivery Strategies for Antisense Oligonucleotide Therapeutics*, ed. Akhtar, 1995; Maurer et al., *Mol. Membr. Biol.*, 16:129, 1999; Hofland and Huang, *Handb. Exp. Pharmacol.* 137:165, 1999; and Lee et al., *ACS Symp. Ser.* 752:184, 2000, all of which are incorporated herein by reference. Beigelman et al., U.S. Pat. No. 6,395,713 and Sullivan et al., PCT WO 94/02595 further describe the general methods for delivery of nucleic acid molecules. Nucleic acid molecules can be administered to cells by a variety of methods known to those of skill in the art, including, but not restricted to, encapsulation in liposomes, by iontophoresis, or by incorporation into other vehicles, such as hydrogels, cyclodextrins (see for example Gonzalez et al., *Bioconjugate Chem.* 10:1068, 1999), biodegradable nanocapsules, and bioadhesive microspheres, or by proteinaceous vectors (O'Hare and Normand, International PCT Publication No. WO 00/53722).

Another aspect of the invention provides for the delivery of iRNA agents to the respiratory tract. The respiratory tract includes the upper airways, including the oropharynx and larynx, followed by the lower airways, which include the trachea followed by bifurcations into the bronchi and bronchioli. The upper and lower airways are called the conductive airways. The terminal bronchioli then divide into respiratory bronchioli which then lead to the ultimate respiratory zone, the alveoli, or deep lung. The deep lung, or alveoli, are the primary target of inhaled therapeutic aerosols for systemic delivery of iRNA agents.

Pulmonary delivery compositions can be delivered by inhalation by the patient of a dispersion so that the composition, preferably the iRNA agent, within the dispersion can reach the lung where it can, for example, be readily absorbed through the alveolar region directly into blood circulation. Pulmonary delivery can be effective both for systemic delivery and for localized delivery to treat diseases of the lungs.

Pulmonary delivery can be achieved by different approaches, including the use of nebulized, aerosolized, micellular and dry powder-based formulations; administration by inhalation may be oral and/or nasal. Delivery can be achieved with liquid nebulizers, aerosol-based inhalers, and dry powder dispersion devices. Metered-dose devices are preferred. One of the benefits of using an atomizer or inhaler is that the potential for contamination is minimized because the devices are self contained. Dry powder dispersion devices, for example, deliver drugs that may be readily formulated as dry powders. An iRNA composition may be stably stored as lyophilized or spray-dried powders by itself or in combination with suitable powder carriers. The delivery of a composition for inhalation can be mediated by a dosing timing element which can include a timer, a dose counter, time measuring device, or a time indicator which when incorporated into the device enables dose tracking, compliance monitoring, and/or dose triggering to a patient during administration of the aerosol medicament.

Examples of pharmaceutical devices for aerosol delivery include metered dose inhalers (MDIs), dry powder inhalers (DPIs), and air-jet nebulizers. Exemplary delivery systems by inhalation which can be readily adapted for delivery of the subject iRNA agents are described in, for example, U.S. Pat. Nos. 5,756,353; 5,858,784; and PCT applications WO98/31346; WO98/10796; WO00/27359; WO01/54664; WO02/060412. Other aerosol formulations that may be used for delivering the iRNA agents are described in U.S. Pat. Nos. 6,294,153; 6,344,194; 6,071,497, and PCT applications WO02/066078; WO02/053190; WO01/60420; WO00/66206. Further, methods for delivering iRNA agents can be adapted from those used in delivering other oligonucleotides (e.g., an antisense oligonucleotide) by inhalation, such as described in Templin et al., Antisense Nucleic Acid Drug Dev, 2000, 10:359-68; Sandrasagra et al., Expert Opin Biol Ther, 2001, 1:979-83; Sandrasagra et al., Antisense Nucleic Acid Drug Dev, 2002, 12:177-81.

The delivery of the inventive agents may also involve the administration of so called "pro-drugs", i.e. formulations or chemical modifications of a therapeutic substance that require some form of processing or transport by systems innate to the subject organism to release the therapeutic substance, preferably at the site where its action is desired. For example, the human lungs can remove or rapidly degrade hydrolytically cleavable deposited aerosols over periods ranging from minutes to hours. In the upper airways, ciliated epithelia contribute to the "mucociliary excalator" by which particles are swept from the airways toward the mouth. Pavia, D., "Lung Mucociliary Clearance," in Aerosols and the Lung: Clinical and Experimental Aspects, Clarke, S. W. and Pavia, D., Eds., Butterworths, London, 1984. In the deep lungs, alveolar macrophages are capable of phagocytosing particles soon after their deposition. Warheit et al. Microscopy Res. Tech., 26: 412-422 (1993); and Brain, J. D., "Physiology and Pathophysiology of Pulmonary Macrophages," in The Reticuloendothelial System, S. M. Reichard and J. Filkins, Eds., Plenum, New. York., pp. 315-327, 1985.

In preferred embodiments, particularly where systemic dosing with the iRNA agent is desired, the aerosoled iRNA agents are formulated as microparticles. Microparticles having a diameter of between 0.5 and ten microns can penetrate the lungs, passing through most of the natural barriers. A diameter of less than ten microns is required to bypass the throat; a diameter of 0.5 microns or greater is required to avoid being exhaled.

The iRNA agent of the invention can be delivered using an implant. Such implants can be biodegradable and/or biocompatible implants, or may be non-biodegradable implants. The implants may be permeable or impermeable to the active agent.

The iRNA agent of the invention can also be administered topically, e.g. to the skin, for example by patch or by direct application to the dermis, or by iontophoresis. Ointments, sprays, or droppable liquids can be delivered by delivery systems known in the art such as applicators or droppers.

The iRNA agent of the invention may be provided in sustained release compositions, such as those described in, for example, U.S. Pat. Nos. 5,672,659 and 5,595,760. The use of immediate or sustained release compositions depends on the nature of the condition being treated. If the condition consists of an acute or over-acute disorder, treatment with an immediate release form will be preferred over a prolonged release composition. Alternatively, for certain preventative or long-term treatments, a sustained release composition may be appropriate.

In addition to treating pre-existing disorders or diseases associated with undesired TGF-beta signaling, iRNA agents of the invention can be administered prophylactically in order to prevent or slow the onset of these and related disorders or diseases. In prophylactic applications, an iRNA of the invention is administered to a patient susceptible to or otherwise at risk of a particular disorder or disease associated with undesired TGF-beta signaling.

The iRNA agent of the invention can be administered in a single dose or in multiple doses. Where the administration of the iRNA agent of the invention is by infusion, the infusion can be a single sustained dose or can be delivered by multiple infusions. Injection of the agent directly into the tissue is at or near the site of undesired TGF-beta signaling is preferred. Multiple injections of the agent into the tissue at or near the site of undesired TGF-beta signaling are also preferred.

Dosage. The dosage can be an amount effective to treat or prevent a disorder or disease associated with undesired TGF-beta signaling.

One skilled in the art can readily determine an appropriate dosage regimen for administering the iRNA agent of the invention to a given subject. For example, the iRNA agent can be administered to the subject once, e.g., as a single injection or deposition at or near the site of undesired TGF-beta signaling. Alternatively, the unit dose is administered less frequently than once a day, e.g., less than every 2, 4, 8 or 30 days. In another embodiment, the unit dose is not administered with a frequency (e.g., not a regular frequency). Because iRNA agent mediated silencing can persist for several days after administering the iRNA agent composition, in many instances, it is possible to administer the composition with a frequency of less than once per day, or, for some instances, only once for the entire therapeutic regimen, or only upon the reoccurrence of a symptom or disease state. Alternatively, the iRNA agent can be administered once or twice daily to a subject for a period of from about three to about twenty-eight days, more preferably from about seven to about ten days. In a preferred dosage regimen, the iRNA agent is injected at or near a site of unwanted TGF-beta expression (such as near a site of fibrosis or sclerosis) once a day for seven days. Where a dosage regimen comprises multiple administrations, it is understood that the effective amount of iRNA agent administered to the subject can comprise the total amount of iRNA agent administered over the entire dosage regimen.

In one embodiment, a subject is administered an initial dose, and one or more maintenance doses of an iRNA agent, e.g., a double-stranded iRNA agent, or siRNA agent, (e.g., a precursor, e.g., a larger iRNA agent which can be processed into an siRNA agent, or a DNA which encodes an iRNA agent, e.g., a double-stranded iRNA agent, or siRNA agent, or precursor thereof). The maintenance doses are preferably administered no more than once every 5, 10, or 30 days. Further, the treatment regimen may last for a period of time which will vary depending upon the nature of the particular disease, its severity and the overall condition of the patient. In preferred embodiments the dosage may be delivered no more than once per day, e.g., no more than once per 24, 36, 48, or more hours, e.g., no more than once every 5 or 8 days. Following treatment, the patient can be monitored for changes in his condition and for alleviation of the symptoms of the disease state. The dosage of the compound may either be increased in the event the patient does not respond significantly to current dosage levels, or the dose may be decreased if an alleviation of the symptoms of the disease state is observed, if the disease state has been ablated, or if undesired side-effects are observed.

The effective dose can be administered in a single dose or in two or more doses, as desired or considered appropriate under the specific circumstances. If desired to facilitate repeated or frequent infusions, implantation of a delivery device, e.g., a pump, semi-permanent stent (e.g., intravenous, intraperitoneal, intracistemal or intracapsular), or reservoir may be advisable.

The concentration of the iRNA agent composition is an amount sufficient to be effective in treating or preventing a disorder or to regulate a physiological condition in humans. The concentration or amount of iRNA agent administered will depend on the parameters determined for the agent and the method of administration, e.g. administration to the lung. For example, inhalable formulations may require lower concentrations of some ingredients in order to avoid irritation or discomfort compared to oral formulations. It is sometimes desirable to dilute an oral formulation up to 10-100 times in order to provide a suitable inhalable formulation.

Certain factors may influence the dosage required to effectively treat a subject, including but not limited to the severity and responsiveness of the disease or disorder, previous treatments, the general health and/or age of the subject, and other diseases present. It will also be appreciated that the effective dosage of an iRNA agent such as an siRNA agent used for treatment may increase or decrease over the course of a particular treatment. Changes in dosage may result and become apparent from the results of diagnostic assays. For example, the subject can be monitored after administering an iRNA agent composition. Based on information from the monitoring, an additional amount of the iRNA agent composition can be administered.

Moreover, depending on the above factors, the course of treatment may last from several days to several months, or until a cure is effected or a diminution of disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual compounds, and can generally be estimated based on EC50s found to be effective in in vitro and in vivo animal models.

Dosage levels on the order of about 1 µg/kg to 100 mg/kg of body weight per administration are useful in the treatment of the disorders or diseases associated with undesired TGF-beta signaling. The preferred dosage range is about 0.00001 mg to about 3 mg per kg body weight of the subject to be treated, or preferably about 0.0001-0.001 mg per kg body weight, about 0.03-3.0 mg per kg body weight, about 0.1-3.0 mg per kg body weight or about 0.3-3.0 mg per kg body weight.

An iRNA agent can be administered at a unit dose less than about 75 mg per kg of bodyweight, or less than about 70, 60, 50, 40, 30, 20, 10, 5, 2, 1, 0.5, 0.1, 0.05, 0.01, 0.005, 0.001, or 0.0005 mg per kg of bodyweight, and less than 200 nmol of iRNA agent (e.g., about $4.4 \times 10^{16}$ copies) per kg of bodyweight, or less than 1500, 750, 300, 150, 75, 15, 7.5, 1.5, 0.75, 0.15, 0.075, 0.015, 0.0075, 0.0015, 0.00075, 0.00015 nmol of iRNA agent per kg of bodyweight. The unit dose, for example, can be administered by injection (e.g., intravenous or intramuscular, intrathecally, or directly into an organ), an inhaled dose, or a topical application.

Delivery of an iRNA agent directly to an organ (e.g., directly to the liver or lung) can be at a dosage on the order of about 0.00001 mg to about 3 mg per organ, or preferably about 0.0001-0.001 mg per organ, about 0.03-3.0 mg per organ, about 0.1-3.0 mg per kg body weight or about 0.3-3.0 mg per organ.

Where an initial dose/maintenance dose regimen is followed, the maintenance dose or doses are generally lower than the initial dose, e.g., one-half less of the initial dose. A maintenance regimen can include treating the subject with a dose or doses ranging from 0.01 µg to 75 mg/kg of body weight per day, e.g., 70, 60, 50, 40, 30, 20, 10, 5, 2, 1, 0.5, 0.1, 0.05, 0.01, 0.005, 0.001, or 0.0005 mg per kg of bodyweight per day.

The invention is further illustrated by the following examples, which should not be construed as further limiting.

EXAMPLES

Example 1

Selection for the Targeting of TGF-Beta by Short Interfering siRNAs siRNA design was carried out to identify siRNAs targeting human and mouse TGF-beta 1 genes. The siRNA in silico selection resulted in 28 siRNAs satisfying our selection criteria.

Human (NM_000660.3; May 4, 2005) and mouse (NM_011577.1; Dec. 17, 2003) mRNA sequences to TGF-beta were downloaded from NCBI resource on the worldwide web at ncbi.nlm.nih.gov/entrez/query.fcgi?CMD= search& DB=nucleotide.

To setup an environment for sequence analysis, BioEdit Sequence Alignment Editor software (Version 7.0.4.1; Hall, T. A., Nucl. Acids. Symp. Ser., 1999, 41:95-98) was downloaded from the worldwide web at mbio.ncsu.edu/BioEdit/bioedit.html and installed on a windows 2000 computer.

The siRNA selection process was run as follows: ClustalW multiple alignment (Thompson J D, et al., Nucleic Acids Res. 1994, 22:4673-80) function of the software was used to generate a global alignment of human and mouse mRNA sequences. Conserved regions were identified by embedded sequence analysis function of the software. For this, conserved regions were defined as sequence stretches with a minimum length of 19 bases for all aligned sequences containing no internal gaps. In order to have a reference sequence available for positions of conserved stretches and finally siRNA target region coordination, a mapping file with positions of consensus sequence relative to human mRNA sequence was generated by the software and analyzed by a perl script.

The siRNA design web interface available at the Whitehead Institute for Biomedical Research (on the worldwide web at jura.wi.mit.edu/siRNAext) was used to identify all candidate siRNAs targeting the conserved regions as well as their predicted off-target hits to human and mouse sequences. For this purpose, candidate siRNAs proposed by the tool were subjected to the software embedded off-target analysis by running the NCBI blast algorithm against the NCBI human and mouse RefSeq database.

Blast results were downloaded and analyzed by a perl script in order to extract an off-target score for each candidate siRNA that was used for siRNA ranking. Final goal for ranking and selection was to prefer siRNAs with high specificity. We defined an off-target score to express off-target potential of each siRNA based on the following assumptions:

1) high specificity can be predicted by weak identity to off-target hits
2) positions 2 to 9 (counting 5' to 3') of a strand (seed region) may contribute more to off-target potential than rest of sequence (non-seed region)

Thus, the identity score of the antisense strand calculated by blast was considered as well as the positions of occurring mismatches. The off-target score was defined as the highest score out of all scores for an siRNA calculated for each off-target hit obtained by blast.

The off-target score was calculated as follows: identity score−0.2*mismatches in seed region.

siRNAs were sorted according to off-target score (ascending). The top 28 siRNAs according to the above criteria were selected and synthesized.

Designing siRNAs Against TGF-Beta mRNA siRNA against TGF-beta mRNA were synthesized chemically using procedures established in the art. Two different designs of siRNAs were synthesized and tested for each base sequence obtained in the selection step described above, for a total of 56 siRNAs. The first group consisted of unmodified ribonucleotides, except that the unpaired 3'-overhangs on both strands consisted of 2'-deoxy thymidines. The second group further included a phosphorothioate linkage between the two unpaired 2'-deoxy thymidines at the end of each strand, 2'O-methyl modifications at every pyrimidine base in the sense strand, and 2'O-methyl modifications at every uridine occurring in a sequence context of 5'-ua-3' and every cytidine occurring in a sequence context of 5'-ca-3'. Modifications in the oligonucleotide strands were accomplished by using the appropriate modified monomer phosphoramidite. The siRNA sequences of those siRNAs synthesized are listed in Table 1, together with the position of the target sequence for each siRNA in NM_000660.3.

Example 2

TGF-Beta siRNA In Vitro Screening Protocol

Human lung epithelial A549 carcinoma cells were transfected with unstabilized and phosphorothioate/O-methyl exo-/endonuclease stabilized siRNAs to select a set of most active siRNAs for further development as potential drug candidates in preclinical and clinical studies.

For transfections, A549 cells (ATCC, Manassas, USA, ATCC #: CCL-185) were seeded at $1.5 \times 10^4$ cells/well on 96-well cell culture plates (Greiner Bio-One GmbH, Frickenhausen, Germany) in 100 µl growth medium (RPMI 1640, 10% fetal calf serum, 100 u/ml penicillin 100 µg/ml streptomycin, 2 mM L-glutamine; Biochrom AG, Berlin, Germany). Transfection of each siRNA was performed 24 h post-seeding at 100 nM and 10 nM final concentration of siRNA duplex in quadruplets using Lipofectamine 2000 (Invitrogen GmbH, Karlsruhe, Germany). For each well, 0.5 µl Lipofectamine 2000 were mixed with 12.5 µl Opti-MEM (Invitrogen) and incubated for 5 min at room temperature. To achieve a final siRNA concentration of 100 nM in the incubation mixture, 2.5 µl of a 5 µM solution of siRNA in annealing buffer per well were mixed with 10 µl Opti-MEM, per well. To achieve a final siRNA concentration of 10 nM, 2.5 µl of a 0.5 µM solution of siRNA in annealing buffer were mixed with 10 µl Opti-MEM, per well. The siRNA solution was combined with the diluted Lipofectamine 2000 solution, gently mixed and incubated for 20 minutes at room temperature to allow complex formation. In the meantime, growth medium was removed from cells and replaced by 100 µl/well of fresh medium. 25 µl of the siRNA-Lipofectamine2000-complex solution were applied to the cells to a final volume of 125 µl per well and cells were incubated for 24 h at 37° C. and 5% $CO_2$ in a humidified incubator (Heraeus GmbH, Hanau).

Following incubation, TGF-beta mRNA levels were determined by QuantiGene bDNA-kit (Genospectra, Fremont, USA). The incubation mixture was replaced by 100 µl fresh growth medium and cells were lysed by applying 50 µl of lysis mixture from the QuantiGene bDNA-kit and incubation for 30 min at 53° C. Cell lysates were incubated in parallel with bDNA probes specific to hGAPDH (10 µl lysate) and hTGF-beta (40 µl lysate) on QuantiGene Capture Plates and processed according to the manufacturer's protocol for the QuantiGene bDNA kit. The nucleotide sequences of the bDNA probes used for hTGF-beta and hGAPDH are given in Table 2 and Table 3 below, respectively. Finally, chemoluminescence was measured in a Victor2-Light (Perkin Elmer, Wiesbaden, Germany) as relative light units (RLU) and values obtained with hGAPDH and hTGF-beta probesets were normalized to the respective GAPDH values for each well. TGF-beta/GAPDH ratios obtained with siRNAs directed against TGF-beta finally were related to the value obtained with the same concentration (100 nM or 10 nM) of an unspecific siRNA (directed against ApoB) which was set to 100%.

Effective siRNAs from the screen were further characterized by dose response curves (DRC). Transfections for dose response curves were performed at the following concentrations: 100 nM, 25 nM, 6.3 nM, 1.6 nM, 0.4 nM, 0.1 nM, 25 pM according to the above protocol. The % TGF-beta mRNA knockdown again was related to a 100% value obtained from a control siRNA transfection. The dsRNA concentrations at which 50% of their maximal activity was achieved (Inhibitory concentration 50%, IC50) were calculated by curve fitting with the computer software Xlfit, (ID Business Solutions Ltd., Guildford, Surrey, UK) using the following parameters: Dose Response One Site, 4 Parameter Logistic Model, fit= $(A+((B-A)/(1+(((10^\wedge C)/x)^\wedge D))))$, inv=$((10^\wedge C)/((((B-A)/(y-A))-1)^\wedge(1/D)))$, res=$(y-\text{fit})$.

bDNA Probes Used in bDNA Assay for TGF-β (Generated with Bayer QuantiGene Probeset Software):

TABLE 2

TGF-β-specific probes detecting hsTGF-β1
(Genbank accession no. NM_000660.3)

| FPL Name | Function | Sequence | SEQ ID NO |
|---|---|---|---|
| hsTGFb 001 | CE | GGGCTCCGGTTCTGCACTCTTTTT TCTCTTGGAAAGAAAGT | 113 |
| hsTGFb 002 | CE | CGCGGGTGACCTCCTTGGTTTTTC TCTTGGAAAGAAAGT | 114 |
| hsTGFb 003 | CE | GCAGCTCTGCCCGGGAGATTTTTC TCTTGGAAAGAAAGT | 115 |
| hsTGFb 004 | CE | TTTTAACTTGAGCCTCAGCAGACT TTTTCTCTTGGAAAGAAAGT | 116 |
| hsTGFb 005 | CE | GGTTGCTGAGGTATCGCCAGTTTT TCTCTTGGAAAGAAAGT | 117 |
| hsTGFb 006 | CE | GCTGGGTGCCAGCAGCCTTTTTCT CTTGGAAAGAAAGT | 118 |
| hsTGFb 007 | LE | CGTAGTAGTCGGCCTCAGGCTCTT TTTAGGCATAGGACCCGTGTCT | 119 |
| hsTGFb 008 | LE | TGTGGGTTTCCACCATTAGCATTT TTAGGCATAGGACCCGTGTCT | 120 |
| hsTGFb 009 | LE | GCTTCTCGGAGCTCTGATGTGTTT TTTAGGCATAGGACCCGTGTCT | 121 |
| hsTGFb 010 | LE | GCAACACGGGTTCAGGTACCTTTT TAGGCATAGGACCCGTGTCT | 122 |
| hsTGFb 011 | LE | GAATTGTTGCTGTATTTCTGGTAC ATTTTTAGGCATAGGACCCGTGTC T | 123 |
| hsTGFb 012 | BL | TGCTTGAACTTGTCATAGATTTCG T | 124 |
| hsTGFb 013 | BL | TGAAGAACATATATATGCTGTGTG TACTC | 125 |
| hsTGFb 014 | BL | GCTCCACGTGCTGCTCCAC | 126 |

TABLE 3

GAPDH-specific probes detecting hsGAPDH
(Genbank accession no. NM_002046.2):

| FPL Name | Function | Sequence | SEQ ID NO |
|---|---|---|---|
| hGAP001 | CE | GAATTTGCCATGGGTGGAATTTTTCT CTTGGAAAGAAAGT | 127 |
| hGAP002 | CE | GGAGGGATCTCGCTCCTGGATTTTCT CTTGGAAAGAAAGT | 128 |
| hGAP003 | CE | CCCCAGCCTTCTCCATGGTTTTTCTC TTGGAAAGAAAGT | 129 |
| hGAP004 | CE | GCTCCCCCCTGCAAATGAGTTTTCTC TTGGAAAGAAAGT | 130 |
| hGAP005 | LE | AGCCTTGACGGTGCCATGTTTTTAGGC ATAGGACCCGTGTCT | 131 |
| hGAP006 | LE | GATGACAAGCTTCCCGTTCTCTTTTTA GGCATAGGACCCGTGTCT | 132 |
| hGAP007 | LE | AGATGGTGATGGGATTTCCATTTTTTT AGGCATAGGACCCGTGTCT | 133 |
| hGAP008 | LE | GCATCGCCCCACTTGATTTTTTTTAG GCATAGGACCCGTGTCT | 134 |
| hGAP009 | LE | CACGACGTACTCAGCGCCATTTTTAGG CATAGGACCCGTGTCT | 135 |
| hGAP010 | LE | GGCAGAGATGATGACCCTTTTGTTTTT AGGCATAGGACCCGTGTCT | 136 |
| hGAP011 | BL | GGTGAAGACGCCAGTGGACTC | 137 |

Table 4 shows the relative activity of the dsRNA duplexes of Table 1 towards reducing TGF-beta mRNA in A549 cells after incubation with the respective dsRNA at 100 nM or 10 nM concentration, expressed as % of the TGF-beta mRNA concentration found in A549 cells that were similarly treated except for incubation with the same concentration of a dsRNA specific for ApoB. In addition, IC50 are given for select duplexes.

TABLE 4

Activity of siRNAs in lowering TGF-beta mRNA in A549 cells compared to A549 cells treated with a control siRNA specific for ApoB

| Duplex identifier | remaining TGF-beta RNA in % of control | | IC(50) [nM] |
|---|---|---|---|
| | at 100 nM duplex conc. | at 10 nM duplex conc. | |
| AL-DP-6837 | 29 ± 5% | 47 ± 19% | |
| AL-DP-6140 | 84 ± 7% | 88 ± 9% | |
| AL-DP-6838 | 22 ± 12% | 34 ± 8% | 0.67 |
| AL-DP-6141 | 81 ± 16% | 118 ± 13% | |
| AL-DP-6839 | 99 ± 10% | 105 ± 5% | |
| AL-DP-6142 | 87 ± 3% | 115 ± 18% | |
| AL-DP-6840 | 31 ± 6% | 37 ± 1% | |
| AL-DP-6143 | 48 ± 3% | 86 ± 7% | 23 |
| AL-DP-6841 | 75 ± 13% | 65 ± 29% | |
| AL-DP-6144 | 80 ± 7% | 94 ± 12% | |
| AL-DP-6842 | 28 ± 10% | 27 ± 4% | 0.12 |
| AL-DP-6145 | 78 ± 9% | 100 ± 22% | |
| AL-DP-6843 | 77 ± 9% | 69 ± 13% | |
| AL-DP-6146 | 81 ± 3% | 102 ± 4% | |
| AL-DP-6844 | 48 ± 7% | 45 ± 20% | |
| AL-DP-6147 | 71 ± 18% | 99 ± 12% | |
| AL-DP-6845 | 20 ± 17% | 29 ± 5% | 0.16 |
| AL-DP-6148 | 87 ± 20% | 98 ± 11% | |
| AL-DP-6846 | 40 ± 14% | 49 ± 29% | |
| AL-DP-6149 | 90 ± 13% | 96 ± 13% | |
| AL-DP-6847 | 36 ± 22% | 46 ± 27% | |
| AL-DP-6150 | 66 ± 22% | 75 ± 9% | |
| AL-DP-6848 | 14 ± 5% | 20 ± 6% | 0.31 |
| AL-DP-6151 | 95 ± 5% | 122 ± 20% | |
| AL-DP-6849 | 33 ± 12% | 31 ± 9% | |
| AL-DP-6262 | 75 ± 5% | 113 ± 4% | |
| AL-DP-6850 | 68 ± 30% | 74 ± 6% | |
| AL-DP-6263 | 102 ± 27% | 142 ± 19% | |
| AL-DP-6851 | 26 ± 11% | 52 ± 11% | |
| AL-DP-6264 | 23 ± 3% | 59 ± 9% | 4.4 |
| AL-DP-6852 | 21 ± 9% | 32 ± 18% | |
| AL-DP-6265 | 86 ± 15% | 79 ± 16% | |
| AL-DP-6853 | 41 ± 12% | 52 ± 14% | |
| AL-DP-6266 | 83 ± 3% | 97 ± 32% | |
| AL-DP-6854 | 92 ± 12% | 118 ± 33% | |

TABLE 4-continued

Activity of siRNAs in lowering TGF-beta mRNA in A549 cells compared to A549 cells treated with a control siRNA specific for ApoB

| Duplex identifier | remaining TGF-beta RNA in % of control | | IC(50) [nM] |
|---|---|---|---|
| | at 100 nM duplex conc. | at 10 nM duplex conc. | |
| AL-DP-6267 | 79 ± 12% | 83 ± 11% | |
| AL-DP-6855 | 22 ± 2% | 28 ± 6% | |
| AL-DP-6268 | 88 ± 15% | 107 ± 46% | |
| AL-DP-6856 | 43 ± 4% | 54 ± 3% | |
| AL-DP-6269 | 70 ± 11% | 92 ± 24% | |
| AL-DP-6857 | 13 ± 5% | 35 ± 24% | 0.04 |
| AL-DP-6270 | 71 ± 15% | 89 ± 30% | |
| AL-DP-6858 | 11 ± 3% | 28 ± 17% | 0.13 |
| AL-DP-6271 | 34 ± 12% | 51 ± 15% | 0.68 |
| AL-DP-6859 | 14 ± 2% | 26 ± 11% | 0.15 |
| AL-DP-6272 | 33 ± 5% | 56 ± 6% | 2.2 |
| AL-DP-6860 | 31 ± 1% | 45 ± 11% | |
| AL-DP-6273 | 118 ± 29% | 161 ± 17% | |
| AL-DP-6861 | 32 ± 7% | 65 ± 37% | |
| AL-DP-6274 | 76 ± 4% | 111 ± 11% | |
| AL-DP-6862 | 16 ± 3% | 27 ± 14% | 0.19 |
| AL-DP-6275 | 93 ± 41% | 96 ± 20% | |
| AL-DP-6863 | 36 ± 17% | 37 ± 15% | |
| AL-DP-6276 | 56 ± 12% | 74 ± 32% | |
| AL-DP-6864 | 46 ± 26% | 62 ± 19% | |
| AL-DP-6277 | 110 ± 18% | 83 ± 40% | |

From Table 4, it can be seen that, at 100 nM concentration, AL-DP-6858, AL-DP-6857, AL-DP-6859, AL-DP-6848, and AL-DP-6862 reduced TGF-beta mRNA in A549 cells by more than 80%. Additionally, under these circumstances, AL-DP-6845, AL-DP-6852, AL-DP-6838, AL-DP-6855, AL-DP-6264, AL-DP-6851, AL-DP-6842, and AL-DP-6837 reduced TGF-beta mRNA in A549 cells by more than 70%. Additionally, AL-DP-6840, AL-DP-6860, AL-DP-6861, AL-DP-6849, AL-DP-6272, AL-DP-6271, AL-DP-6847, AL-DP-6863 reduced TGF-beta mRNA in A549 cells by more than 60%. Additionally, AL-DP-6846, AL-DP-6853, AL-DP-6856, AL-DP-6864, AL-DP-6844, AL-DP-6143 reduced TGF-beta mRNA in A549 cells by more than 50%. Additionally, AL-DP-6276 reduced TGF-beta mRNA in A549 cells by more than 40%. Additionally, AL-DP-6150 and AL-DP-6850 reduced TGF-beta mRNA in A549 cells by more than 30%. Finally, AL-DP-6269, AL-DP-6270, AL-DP-6147, AL-DP-6262, AL-DP-6841, AL-DP-6274, AL-DP-6843, AL-DP-6145, and AL-DP-6267 reduced TGF-beta mRNA in A549 cells by more than 20%.

Example 3

Screening of Additional siRNA for Activity in Inhibiting TGF-Beta Expression

In order to identify as many RNAi agents with suitable activity as possible, the above screen was extended to further target sequences. For the selection of an expanded screening set we re-calculated the predicted specificity based on the newly available human RefSeq database (Human mRNA sequences in RefSeq release version 21 (downloaded Jan. 12, 2007)) and selected only those 220 non-poly-G siRNAs (no occurrence of 3 or more consecutive guanosines) targeting 19 mer target sequences in NM_000660.3 with off-target scores of 3 or more for the antisense strand. These agents were then screened for their activity in lowering the amount of TGF-beta mRNA present in A549 cells treated with the agents as described above, except that transfection with the agents was performed directly after seeding, rather than 24 h after seeding, and that the concentration of the agents in the transfection mixture was 30 nM.

As may be concluded from the results shown in Table 5, AD-14501, AD-14503, AD-14507, AD-14554, AD-14594, AD-14597, and AD-14633 reduced TGF-beta mRNA in A549 cells by more than 90%. Additionally, under these circumstances, AD-14419, AD-14420, AD-14421, AD-14422, AD-14423, AD-14428, AD-14430, AD-14434, AD-14438, AD-14449, AD-14453, AD-14459, AD-14460, AD-14464, AD-14469, AD-14470, AD-14473, AD-14474, AD-14476, AD-14486, AD-14490, AD-14495, AD-14496, AD-14497, AD-14509, AD-14515, AD-14522, AD-14526, AD-14540, AD-14552, AD-14555, AD-14557, AD-14565, AD-14567, AD-14568, AD-14582, AD-14588, AD-14590, AD-14592, AD-14598, AD-14600, AD-14601, AD-14603, AD-14604, AD-14608, AD-14610, AD-14612, AD-14614, AD-14622, AD-14634, and AD-14635 reduced TGF-beta mRNA in A549 cells by more than 80%. Additionally, under these circumstances, AD-14425, AD-14426, AD-14427, AD-14429, AD-14431, AD-14436, AD-14437, AD-14441, AD-14448, AD-14458, AD-14463, AD-14467, AD-14477, AD-14482, AD-14483, AD-14491, AD-14502, AD-14505, AD-14508, AD-14512, AD-14513, AD-14519, AD-14524, AD-14537, AD-14546, AD-14548, AD-14549, AD-14559, AD-14563, AD-14564, AD-14569, AD-14578, AD-14579, AD-14587, AD-14595, AD-14599, AD-14607, AD-14609, AD-14629, AD-14631, and AD-14637 reduced TGF-beta mRNA in A549 cells by more than 70%. Additionally, under these circumstances, AD-14447, AD-14451, AD-14471, AD-14484, AD-14487, AD-14498, AD-14523, AD-14527, AD-14529, AD-14539, AD-14541, AD-14558, AD-14561, AD-14573, AD-14589, AD-14596, AD-14605, AD-14615, AD-14626, and AD-14630 reduced TGF-beta mRNA in A549 cells by more than 60%. Additionally, under these circumstances, AD-14432, AD-14480, AD-14485, AD-14488, AD-14499, AD-14504, AD-14516, AD-14518, AD-14520, AD-14547, AD-14572, AD-14577, AD-14580, AD-14583, AD-14584, AD-14618, AD-14621, and AD-14625 reduced TGF-beta mRNA in A549 cells by more than 50%. Additionally, under these circumstances, AD-14435, AD-14445, AD-14450, AD-14456, AD-14466, AD-14475, AD-14489, AD-14492, AD-14511, AD-14535, AD-14536, AD-14538, AD-14553, AD-14560, AD-14562, AD-14576, AD-14581, AD-14586, and AD-14627 reduced TGF-beta mRNA in A549 cells by more than 40%. Additionally, under these circumstances, AD-14433, AD-14472, AD-14478, AD-14493, AD-14510, AD-14544, AD-14566, AD-14570, AD-14575, AD-14593, and AD-14613 reduced TGF-beta mRNA in A549 cells by more than 30%. Additionally, under these circumstances, AD-14424, AD-14442, AD-14444, AD-14446, AD-14454, AD-14525, AD-14543, AD-14571, AD-14606, AD-14611, AD-14616, AD-14617, AD-14619, and AD-14638 reduced TGF-beta mRNA in A549 cells by more than 20%.

TABLE 5

Additional RNAi agents targeting hTGF-beta

| Duplex identifier | 19 mer target sequence | target sequence in NM_000660.3 | Sense strand sequence | SEQ ID NO: | Antisense strand sequence | SEQ ID NO: | Remaining TGF-beta mRNA in % of controls ± stand. dev. |
|---|---|---|---|---|---|---|---|
| AD-14419 | aauuccuggcgauaccuca | 1396-1414 | aauuccuggcgauaccucaTT | 138 | ugagguaucgccaggaauuTT | 139 | 16 ± 1 |
| AD-14420 | ucgcgcccaucuagguuau | 654-672 | ucgcgcccaucuagguuauTT | 140 | auaaccuagaugggcgcgaTT | 141 | 19 ± 2 |
| AD-14421 | ggucacccgcgugcuaaug | 1188-1206 | ggucacccgcgugcuaaugTT | 142 | cauuagcacgcgggugaccTT | 143 | 19 ± 2 |
| AD-14422 | aggucacccgcgugcuaau | 1187-1205 | aggucacccgcgugcuaauTT | 144 | auuagcacgcgggugaccuTT | 145 | 10 ± 1 |
| AD-14423 | cacccgcgugcuaauggug | 1191-1209 | cacccgcgugcuaauggugTT | 146 | caccauuagcacgcgggugTT | 147 | 18 ± 1 |
| AD-14424 | uacaaccagcauaacccgg | 1894-1912 | uacaaccagcauaacccggTT | 148 | ccggguuaugcugguuguaTT | 149 | 79 ± 5 |
| AD-14425 | aucgcgcccaucuagguua | 653-671 | aucgcgcccaucuagguuaTT | 150 | uaaccuagaugggcgcgauTT | 151 | 24 ± 1 |
| AD-14426 | guaccagaucgcgcccauc | 646-664 | guaccagaucgcgcccaucTT | 152 | gaugggcgcgaucugguacTT | 153 | 21 ± 1 |
| AD-14427 | agacggaucucucuccgac | 589-607 | agacggaucucucuccgacTT | 154 | gucggagagagauccgucuTT | 155 | 26 ± 4 |
| AD-14428 | cgcgcccaucuagguuauu | 655-673 | cgcgcccaucuagguuauuTT | 156 | aauaaccuagaugggcgcgTT | 157 | 19 ± 1 |
| AD-14429 | cccgcgcauccuagacccu | 558-576 | cccgcgcauccuagacccuTT | 158 | agggucuaggaugcgcgggTT | 159 | 24 ± 3 |
| AD-14430 | gcgcccaucuagguuauuu | 656-674 | gcgcccaucuagguuauuuTT | 160 | aaauaaccuagaugggcgcTT | 161 | 18 ± 1 |
| AD-14431 | uccgugggauacugagaca | 674-692 | uccgugggauacugagacaTT | 162 | ugucucaguaucccacggaTT | 163 | 25 ± 3 |
| AD-14432 | cuuucgccuuagcgcccac | 1515-1533 | cuuucgccuuagcgcccacTT | 164 | gugggcgcuaaggcgaaagTT | 165 | 41 ± 2 |
| AD-14433 | acccgcgugcuaauggugg | 1192-1210 | acccgcgugcuaaugguggTT | 166 | ccaccauuagcacgcggguTT | 167 | 60 ± 4 |
| AD-14434 | gcaacaauuccuggcgaua | 1391-1409 | gcaacaauuccuggcgauaTT | 168 | uaucgccaggaauuguugcTT | 169 | 10 ± 0 |
| AD-14435 | aacggguucacuaccggcc | 1576-1594 | aacggguucacuaccggccTT | 170 | ggccgguagugaacccguuTT | 171 | 57 ± 4 |
| AD-14436 | cggguucacuaccggccgc | 1578-1596 | cggguucacuaccggccgcTT | 172 | gcggccgguagugaacccgTT | 173 | 28 ± 3 |
| AD-14437 | cuguauuuaaggacacccg | 2117-2135 | cuguauuuaaggacacccgTT | 174 | cgggugaccuuaaauacagTT | 175 | 21 ± 1 |
| AD-14438 | agguuauuccgugggaua | 666-684 | agguuauuccgugggauaTT | 176 | uaucccacggaaauaaccuTT | 177 | 19 ± 1 |
| AD-14439 | cccucgggagucgccgacc | 458-476 | cccucgggagucgccgaccTT | 178 | ggucggcgacucccgagggTT | 179 | 90 ± 4 |
| AD-14440 | ugugcggcagugguugagc | 1476-1494 | ugugcggcagugguugagcTT | 180 | gcucaaccacugccgcacaTT | 181 | 375 ± 34 |
| AD-14441 | caaccagcauaacccgggc | 1896-1914 | caaccagcauaacccgggcTT | 182 | gcccggguuaugcugguugTT | 183 | 28 ± 4 |
| AD-14442 | uuuugagacuuuuccguug | 281-299 | uuuugagacuuuuccguugTT | 184 | caacggaaaagucucaaaaTT | 185 | 75 ± 2 |
| AD-14443 | uuugagacuuuuccguugc | 282-300 | uuugagacuuuuccguugcTT | 186 | gcaacggaaaagucucaaaTT | 187 | 98 ± 9 |
| AD-14444 | cucuuggcgcgacgcugcc | 326-344 | cucuuggcgcgacgcugccTT | 188 | ggcagcgucgcgccaagagTT | 189 | 70 ± 4 |
| AD-14445 | ucugguaccagaucgcgcc | 642-660 | ucugguaccagaucgcgccTT | 190 | ggcgcgaucugguaccagaTT | 191 | 50 ± 2 |
| AD-14446 | acaccagcccuguucgcgc | 817-835 | acaccagcccuguucgcgcTT | 192 | gcgcgaacagggcuggugu TT | 193 | 71 ± 4 |
| AD-14447 | cggccggccgcgggacuau | 940-958 | cggccggccgcgggacuauTT | 194 | auagucccgcggccggccgTT | 195 | 38 ± 1 |
| AD-14448 | gguaccugaacccguguug | 1296-1314 | gguaccugaacccguguugTT | 196 | caacacggguucagguaccTT | 197 | 21 ± 1 |
| AD-14449 | guaccugaacccguguugc | 1297-1315 | guaccugaacccguguugcTT | 198 | gcaacacggguucagguacTT | 199 | 17 ± 1 |
| AD-14450 | auuccuggcgauaccucag | 1397-1415 | auuccuggcgauaccucagTT | 200 | cugagguaucgccaggaauTT | 201 | 58 ± 6 |
| AD-14451 | auugagggcuuucgccuua | 1507-1525 | auugagggcuuucgccuuaTT | 202 | uaaggcgaaagcccucaauTT | 203 | 31 ± 3 |
| AD-14452 | acaaccagcauaacccggg | 1895-1913 | acaaccagcauaacccgggTT | 204 | cccggguuaugcugguuguTT | 205 | 87 ± 8 |
| AD-14453 | uguauuuaaggacacccgu | 2118-2136 | uguauuuaaggacacccguTT | 206 | acggguguccuuaaauacaTT | 207 | 16 ± 2 |

TABLE 5-continued

Additional RNAi agents targeting hTGF-beta

| Duplex identifier | 19 mer target sequence | target sequence in NM_000660.3 | Sense strand sequence | SEQ ID NO: | Antisense strand sequence | SEQ ID NO: | Remaining TGF-beta mRNA in % of controls ± stand. dev. |
|---|---|---|---|---|---|---|---|
| AD-14454 | gaggacugcggaucucugu | 2174-2192 | gaggacugcggaucucuguTT | 208 | acagagauccgcaguccucTT | 209 | 77 ± 5 |
| AD-14455 | gggaacacuacuguaguua | 2324-2342 | gggaacacuacuguaguuaTT | 210 | uaacuacaguaguguucccTT | 211 | 86 ± 4 |
| AD-14456 | accagcccuguucgcgcuc | 819-837 | accagcccuguucgcgcucTT | 212 | gagcgcgaacagggcugguTT | 213 | 59 ± 0 |
| AD-14457 | agaggacugcggaucucug | 2173-2191 | agaggacugcggaucucugTT | 214 | cagagauccgcaguccucuTT | 215 | 91 ± 3 |
| AD-14458 | guacuacgugggccgcaag | 1968-1986 | guacuacgugggccgcaagTT | 216 | cuugcggcccacguaguacTT | 217 | 24 ± 1 |
| AD-14499 | gaucgcgcccaucuagguu | 652-670 | gaucgcgcccaucuagguuTT | 218 | aaccuagaugggcgcgaucTT | 219 | 13 ± 1 |
| AD-14460 | aacgaaaucuaugacaagu | 1219-1237 | aacgaaaucuaugacaaguTT | 220 | acuugucauagauuucguuTT | 221 | 16 ± 2 |
| AD-14461 | uucgccuuagcgcccacug | 1517-1535 | uucgccuuagcgcccacugTT | 222 | cagugggcgcuaaggcgaaTT | 223 | 107 ± 6 |
| AD-14462 | aucaacgggguucacuaccg | 1573-1591 | aucaacggguucacuaccgTT | 224 | cgguagugaacccguugauTT | 225 | 107 ± 3 |
| AD-14463 | ccgcgcauccuagacccuu | 559-577 | ccgcgcauccuagacccuuTT | 226 | aagggucuaggaugcgcgguTT | 227 | 24 ± 3 |
| AD-14464 | gcgcauccuagacccuuuc | 561-579 | gcgcauccuagacccuuucTT | 228 | gaaagggucuaggaugcgcTT | 229 | 15 ± 1 |
| AD-14465 | uuucgccuuagcgcccacu | 1516-1534 | uuucgccuuagcgcccacuTT | 230 | agugggcgcuaaggcgaaaTT | 231 | 85 ± 6 |
| AD-14466 | cugguaccagaucgcgccc | 643-661 | cugguaccagaucgcgcccTT | 232 | gggcgcgaucugguaccagTT | 233 | 54 ± 3 |
| AD-14467 | cagaucgcgcccaucuagg | 650-668 | cagaucgcgcccaucuaggTT | 234 | ccuagaugggcgcgaucugTT | 235 | 25 ± 1 |
| AD-14468 | uccuaccuuugccgggag | 763-781 | uccuaccuuugccgggagTT | 236 | cucccggcaaaagguaggaTT | 237 | 93 ± 5 |
| AD-14469 | cccuguucgcgcucucggc | 824-842 | cccuguucgcgcucucggcTT | 238 | gccgagagcgcgaacagggTT | 235 | 16 ± 2 |
| AD-14470 | ccuguucgcgcucucggca | 825-843 | ccuguucgcgcucucggcaTT | 240 | ugccgagagcgcgaacaggTT | 241 | 16 ± 3 |
| AD-14471 | cuguucgcgcucucggcag | 826-844 | cuguucgcgcucucggcagTT | 242 | cugccgagagcgcgaacagTT | 243 | 32 ± 3 |
| AD-14472 | aagacuaucgacauggagc | 967-985 | aagacuaucgacauggagcTT | 244 | gcuccaugucgauagucuuTT | 245 | 63 ± 9 |
| AD-14473 | cccgcgugcuaauggugga | 1193-1211 | cccgcgugcuaaugguggaTT | 246 | uccaccauuagcacgcgggTT | 247 | 12 ± 2 |
| AD-14474 | cgugcuaauggugaaacc | 1157-1215 | cgugcuaauggugaaaccTT | 248 | gguuuccaccauuagcacgTT | 249 | 13 ± 1 |
| AD-14475 | ccggaguugugcggcagug | 1469-1487 | ccggaguugugcggcagugTT | 250 | cacugccgcacaacucggTT | 251 | 52 ± 6 |
| AD-14476 | gcuuucgccuuagcgccca | 1514-1532 | gcuuucgccuuagcgcccaTT | 252 | ugggcgcuaaggcgaaagcTT | 253 | 16 ± 0 |
| AD-14477 | agggauaacacacugcaag | 1549-1567 | agggauaacacacugcaagTT | 254 | cuugcagugguuauccccTT | 255 | 22 ± 1 |
| AD-14478 | caucaacggguucacuacc | 1572-1590 | caucaacggguucacuaccTT | 256 | gguagugaacccguugaugTT | 257 | 68 ± 1 |
| AD-14479 | uuuaaggacacccgugccc | 2122-2140 | uuuaaggacacccgugcccTT | 258 | gggcacggguguccuuaaaTT | 259 | 92 ± 5 |
| AD-14480 | gacuuuccguugccgcug | 287-305 | gacuuuccguugccgcugTT | 260 | cagcggcaacggaaaagucTT | 261 | 41 ± 5 |
| AD-14481 | uuuuccguugccgcuggga | 290-308 | uuuuccguugccgcugggaTT | 262 | ucccagcggcaacggaaaaTT | 263 | 81 ± 3 |
| AD-14482 | gggaccucuuggcgcgacg | 321-339 | gggaccucuuggcgcgacgTT | 264 | cgucgcgccaagagguccTT | 265 | 26 ± 1 |
| AD-14483 | ggaccucuuggcgcgacgc | 322-340 | ggaccucuuggcgcgacgcTT | 266 | gcgucgcgccaagaggucTT | 267 | 28 ± 3 |
| AD-14484 | gaccucuuggcgcgacgcu | 323-341 | gaccucuuggcgcgacgcuTT | 268 | agcgucgcgccaagaggucTT | 269 | 33 ± 1 |
| AD-14485 | ccuacacggcgucccucag | 419-437 | ccuacacggcgucccucagTT | 270 | cugagggacgccguguaggTT | 271 | 49 ± 1 |
| AD-14486 | cgcgcauccuagacccuuu | 560-578 | cgcgcauccuagacccuuuTT | 272 | aaagggucuaggaugcgcgTT | 273 | 15 ± 2 |
| AD-14487 | cauccuagacccuuucucc | 564-582 | cauccuagacccuuucuccTT | 274 | ggagaaagggucuaggaugTT | 275 | 33 ± 7 |

TABLE 5-continued

Additional RNAi agents targeting hTGF-beta

| Duplex identifier | 19 mer target sequence | target sequence in NM_000660.3 | Sense strand sequence | SEQ ID NO: | Antisense strand sequence | SEQ ID NO: | Remaining TGF-beta mRNA in % of controls ± stand. dev. |
|---|---|---|---|---|---|---|---|
| AD-14488 | ugguaccagaucgcgccca | 644-662 | ugguaccagaucgcgcccaTT | 276 | ugggcgcgaucugguaccaTT | 277 | 49 ± 5 |
| AD-14489 | uaccagaucgcgcccaucu | 647-665 | uaccagaucgcgcccaucuTT | 278 | agaugggcgcgaucugguaTT | 279 | 59 ± 6 |
| AD-14490 | agaucgcgcccaucuaggu | 651-669 | agaucgcgcccaucuagguTT | 280 | accuagaugggcgcgaucuTT | 281 | 19 ± 3 |
| AD-14491 | gcccaucuagguuauuucc | 658-676 | gcccaucuagguuauuuccTT | 282 | ggaaauaaccuagaugggcTT | 283 | 25 ± 1 |
| AD-14492 | cuaccuuugccgggagac | 765-783 | cuaccuuugccgggagacTT | 284 | gucucccgcaaaagguagTT | 285 | 55 ± 2 |
| AD-14493 | guucgcgcucucggcagug | 828-846 | guucgcgcucucggcagugTT | 286 | cacugccgagagcgcgaacTT | 287 | 66 ± 9 |
| AD-14494 | uucgcgcucucggcagugc | 829-847 | uucgcgcucucggcagugcTT | 288 | gcacugccgagagcgcgaaTT | 289 | 102 ± 12 |
| AD-14495 | accugcaagacuaucgaca | 961-979 | accugcaagacuaucgacaTT | 290 | ugucgauagucuugcagguTT | 291 | 19 ± 1 |
| AD-14496 | cugcaagacuaucgacaug | 963-981 | cugcaagacuaucgacaugTT | 292 | caugucgauagucuugcagTT | 293 | 14 ± 1 |
| AD-14497 | gcaagacuaucgacaugga | 965-983 | gcaagacuaucgacauggaTT | 294 | uccaugucgauagucuugcTT | 295 | 15 ± 1 |
| AD-14498 | caagacuaucgacauggag | 966-984 | caagacuaucgacauggagTT | 296 | cuccaugucgauagucuugTT | 297 | 37 ± 3 |
| AD-14499 | uguacaacagcaccgcga | 1106-1124 | uguacaacagcacccgcgaTT | 298 | ucgcgggugcuguuguacaTT | 299 | 42 ± 2 |
| AD-14500 | ugaggccgacuacuacgcc | 1164-1182 | ugaggccgacuacuacgccTT | 300 | ggcguaguagucggccucaTT | 301 | 122 ± 7 |
| AD-14501 | aaacccacaacgaaaucua | 1211-1229 | aaacccacaacgaaaucuaTT | 302 | uagauuucguugugggwuuTT | 303 | 9 ± 1 |
| AD-14502 | ccacaacgaaaucuaugac | 1215-1233 | ccacaacgaaaucuaugacTT | 304 | gucauagauuucguuguggTT | 305 | 24 ± 2 |
| AD-14503 | aguacacacagcauauaua | 1246-1264 | aguacacacagcauauauaTT | 306 | uauauaugcuguguguacuTT | 307 | 8 ± 0 |
| AD-14504 | cgguaccugaacccguguu | 1295-1313 | cgguaccugaacccguguuTT | 308 | aacacgggwucagguaccgTT | 309 | 45 ± 4 |
| AD-14505 | uaccugaacccguguugcu | 1298-1316 | uaccugaacccguguugcuTT | 310 | agcaacacgggwucagguaTT | 311 | 29 ± 2 |
| AD-14506 | cccguguugcucucccggg | 1306-1324 | cccguguugcucucccgggTT | 312 | cccgggagagcaacacgggTT | 313 | 107 ± 5 |
| AD-14507 | cugcgucugcugaggcuca | 1330-1348 | cugcgucugcugaggcucaTT | 314 | ugagccucagcagacgcagTT | 315 | 9 ± 1 |
| AD-14508 | aggcucaaguuaaaagugg | 1342-1360 | aggcucaaguuaaaaguggTT | 316 | ccacuuuuaacuugagccuTT | 317 | 20 ± 1 |
| AD-14509 | caacaauuccggcgauac | 1392-1410 | caacaauuccggcgauacTT | 318 | guaucgccaggaauuguugTT | 319 | 14 ± 1 |
| AD-14510 | aacaauuccggcgauacc | 1393-1411 | aacaauuccggcgauaccTT | 320 | gguaucgccaggaauuguTT | 321 | 65 ± 3 |
| AD-14511 | uggcgauaccucagcaacc | 1402-1420 | uggcgauaccucagcaaccTT | 322 | gguugcugagguaucgccaTT | 323 | 58 ± 5 |
| AD-14512 | cgauaccucagcaaccggc | 1405-1423 | cgauaccucagcaaccggcTT | 324 | gccgguugcugagguaucgTT | 32S | 20 ± 0 |
| AD-14513 | gauaccucagcaaccggcu | 1406-1424 | gauaccucagcaaccggcuTT | 326 | agccgguugcugagguaucTT | 327 | 24 ± 1 |
| AD-14514 | cuggcacccagcgacucgc | 1426-1444 | cuggcacccagcgacucgcTT | 328 | gcgagucgcugggugccagTT | 329 | 86 ± 13 |
| AD-14515 | gacucgccagaguggwuau | 1438-1456 | gacucgccagaguggwuauTT | 330 | auaaccacucuggcgagucTT | 331 | 11 ± 1 |
| AD-14516 | acucgccagaguggwuauc | 1439-1457 | acucgccagaguggwuaucTT | 332 | gauaaccacucuggcgaguTT | 333 | 47 ± 2 |
| AD-14517 | ugucaccggaguugugcgg | 1464-1482 | ugucaccggaguugugcggTT | 334 | ccgcacaacuccggugacaTT | 335 | 115 ± 7 |
| AD-14518 | caccggaguugugcggcag | 1467-1485 | caccggaguugugcggcagTT | 336 | cugccgcacaacuccggugTT | 337 | 44 ± 3 |
| AD-14519 | accggaguugugcggcagu | 1468-1486 | accggaguugugcggcaguTT | 338 | acugccgcacaacuccgguTT | 339 | 28 ± 2 |
| AD-14520 | aaauugagggcuuucgccu | 1505-1523 | aaauugagggcuuucgccuTT | 340 | aggcgaaagcccucaauuuTT | 341 | 46 ± 2 |
| AD-14521 | uugagggcuuucgccuuag | 1508-1526 | uugagggcuuucgccuuagTT | 342 | cuaaggcgaaagcccucaaTT | 343 | 130 ± 15 |
| AD-14522 | gggcuuucgccuuagcgcc | 1512-1530 | gggcuuucgccuuagcgccTT | 344 | ggcgcuaaggcgaaagcccTT | 345 | 14 ± 1 |

TABLE 5-continued

Additional RNAi agents targeting hTGF-beta

| Duplex identifier | 19 mer target sequence | target sequence in NM_000660.3 | Sense strand sequence | SEQ ID NO: | Antisense strand sequence | SEQ ID NO: | Remaining TGF-beta mRNA in % of controls ± stand. dev. |
|---|---|---|---|---|---|---|---|
| AD-14523 | ccuuagcgcccacugcucc | 1521-1539 | ccuuagcgcccacugcuccTT | 346 | ggagcagugggcgcuaaggTT | 347 | 30 ± 1 |
| AD-14524 | aaguggacaucaacggguu | 1565-1583 | aaguggacaucaacgggu uTT | 348 | aacccguugauguccacuuTT | 349 | 20 ± 1 |
| AD-14525 | caacgghuucacuaccggc | 1575-1593 | caacgghuucacuaccggcTT | 350 | gccgguagugaacccguugTT | 351 | 73 ± 6 |
| AD-14526 | cuaccggccgccgagguga | 1586-1604 | cuaccggccgccgaggugaTT | 352 | ucaccucggcggccgguagTT | 353 | 18 ± 1 |
| AD-14527 | caucugcaaagcucccggc | 1675-1693 | caucugcaaagcucccggcTT | 354 | gccgggagcuuugcagaugTT | 355 | 37 ± 2 |
| AD-14528 | cguguacuacgugggccgc | 1965-1983 | cguguacuacgugggccgcTT | 356 | gcggcccacguaguacacgTT | 357 | 80 ± 4 |
| AD-14529 | caacaugaucgugcgcucc | 2007-2025 | caacaugaucgugcgcuccTT | 358 | ggagcgcacgaucauguugTT | 359 | 35 ± 2 |
| AD-14530 | cugugucauugggcgccug | 2189-2207 | cugugucauugggcgccugTl | 360 | caggcgcccaaugacacagTT | 361 | 89 ± 6 |
| AD-14531 | ugccugucugcacuauucc | 2273-2291 | ugccugucugcacuauuccTT | 362 | ggaauagugcagacaggcaTT | 363 | 97 ± 4 |
| AD-14532 | cacuauuccuuugcccggc | 2283-2301 | cacuauuccuuugcccggcTT | 364 | gccgggcaaaggaauagugTT | 365 | 98 ± 8 |
| AD-14533 | aacacuacuguaguuagau | 2327-2345 | aacacuacuguaguuagauTT | 366 | aucuaacuacaguaguguuTT | 367 | 89 ± 8 |
| AD-14534 | acacuacuguaguuagauc | 2328-2346 | acacuacuguaguuagaucTT | 368 | gaucuaacuacaguaguguTT | 369 | 80 ± 2 |
| AD-14535 | gucugagacgagccgccgc | 185-203 | gucugagacgagccgccgcTT | 370 | gcggcggcucgucucagacTT | 371 | 57 ± 4 |
| AD-14536 | cccuacacggcgucccuca | 418-436 | cccuacacggcgucccucaTT | 372 | ugagggacgccguguagggTT | 373 | 50 ± 4 |
| AD-14537 | acggaucucucuccgaccu | 591-609 | acggaucucucuccgaccuTT | 374 | aggucggagagagauccguTT | 375 | 23 ± 3 |
| AD-14538 | ggccggccgcgggacuauc | 941-959 | ggccggccgcgggacuaucTT | 376 | gauagucccgcggccggccTT | 377 | 50 ± 2 |
| AD-14539 | cgcggccagauccugucca | 1015-1033 | cgcggccagauccuguccaTT | 378 | uggacaggaucuggccgcgTT | 379 | 34 ± 3 |
| AD-14540 | ggaaacccacaacgaaauc | 1209-1227 | ggaaacccacaacgaaaucTT | 380 | gauuucguugugggguuccTT | 381 | 11 ± 0 |
| AD-14541 | acaauuccuggcgauaccu | 1394-1412 | acaauuccuggcgauaccuTT | 382 | agguaucgccaggaauuguTT | 383 | 31 ± 2 |
| AD-14542 | agucugagacgagccgccg | 184-202 | agucugagacgagccgccgTT | 384 | cggcggcucgucucagacuTT | 385 | 87 ± 1 |
| AD-14543 | cacggcgucccucaggcgc | 423-441 | cacggcgucccucaggcgcTT | 386 | gcgccugagggacgccgugTT | 387 | 76 ± 3 |
| AD-14544 | acggcgucccucaggcgcc | 424-442 | acggcgucccucaggcgccTT | 388 | ggcgccugagggacgccguTT | 389 | 68 ± 3 |
| AD-14545 | accagcccucgggagucgc | 453-471 | accagcccucgggagucgcTT | 390 | gcgacucccgagggcugguTT | 391 | 96 ± 7 |
| AD-14546 | gcauccuagacccuuucuc | 563-S81 | gcauccuagacccuuucucTT | 392 | gagaaagggucuaggaugcTT | 393 | 22 ± 2 |
| AD-14547 | gacggaucucucuccgacc | 590-608 | gacggaucucucuccgaccTT | 394 | ggucggagagagauccgucTT | 395 | 43 ± 2 |
| AD-14548 | gguaccagaucgcgcccau | 645-663 | gguaccagaucgcgcccauTT | 396 | augggcgcgaucugguaccTT | 397 | 27 ± 3 |
| AD-14549 | uagguuauuuccguggau | 665-683 | uagguuauuuccguggauTT | 398 | aucccacggaaauaaccuaTT | 399 | 22 ± 1 |
| AD-14550 | accuuugccgggagaccc | 767-785 | accuuugccgggagacccTT | 400 | gggucucccggcaaaagguTT | 401 | 89 ± 2 |
| AD-14551 | ucgcgcucucggcagugcc | 830-848 | ucgcgcucucggcagugccTT | 402 | ggcacugccgagagcgcgaTT | 403 | 95 ± 3 |
| AD-14552 | uauccaccugcaagacuau | 956-974 | uauccaccugcaagacuauTT | 404 | auagucuugcaggggauaTT | 405 | 15 ± 1 |
| AD-14553 | ccgcggccagauccugucc | 1014-1032 | ccgcggccagauccuguccTT | 406 | ggacaggaucuggccgcggTT | 407 | 53 ± 5 |
| AD-14554 | aacccacaacgaaaucuau | 1212-1230 | aacccacaacgaaaucuauTT | 408 | auagauuucguuguggguuTT | 409 | 8 ± 1 |
| AD-14555 | agcgguaccugaacccgug | 1293-1311 | agcgguaccugaacccgugTT | 410 | cacggguucagguaccgcuTT | 411 | 14 ± 2 |
| AD-14556 | uggcacccagcgacucgcc | 1427-1445 | uggcacccagcgacucgccTT | 412 | ggcgagucgcugggugccaTT | 413 | 88 ± 9 |
| AD-14557 | cucgccagagugguuaucu | 1440-1458 | cucgccagagugguuaucuTT | 414 | agauaaccacucuggcgagTT | 415 | 18 ± 2 |

TABLE 5-continued

Additional RNAi agents targeting hTGF-beta

| Duplex identifier | 19 mer target sequence | target sequence in NM_000660.3 | Sense strand sequence | SEQ ID NO: | Antisense strand sequence | SEQ ID NO: | Remaining TGF-beta mRNA in % of controls ± stand. dev. |
|---|---|---|---|---|---|---|---|
| AD-14558 | cggcagugguugagccgug | 1480-1498 | cggcagugguugagccgugTT | 416 | cacggcucaaccacugccgTT | 417 | 32 ± 2 |
| AD-14559 | gugguugagccguggaggg | 1485-1503 | gugguugagccguggagggTT | 418 | cccuccacggcucaaccacTT | 419 | 24 ± 1 |
| AD-14560 | gagggcuuucgccuuagcg | 1510-1528 | gagggcuuucgccuuagcgTT | 420 | cgcuaaggcgaaagcccucTT | 421 | 51 ± 2 |
| AD-14561 | agggcuuucgccuuagcgc | 1511-1529 | agggcuuucgccuuagcgcTT | 422 | gcgcuaaggcgaaagcccuTT | 423 | 37 ± 1 |
| AD-14562 | ggugaccuggccaccauuc | 1600-1618 | ggugaccuggccaccauucTT | 424 | gaaugguggccaggucaccTT | 425 | 51 ± 5 |
| AD-14563 | accauucauggcaugaacc | 1612-1630 | accauucauggcaugaaccTT | 426 | gguucaugccaugaaugguTT | 427 | 29 ± 2 |
| AD-14564 | cauggcaugaaccggccuu | 1618-1636 | cauggcaugaaccggccuuTT | 428 | aaggccgguucaugccaugTT | 429 | 25 ± 2 |
| AD-14565 | ccaacuauugcuucagcuc | 1712-1730 | ccaacuauugcuucagcucTT | 430 | gagcugaagcaauaguuggTT | 431 | 11 ± 1 |
| AD-14566 | gaacugcugcgugcggcag | 1740-1758 | gaacugcugcgugcggcagTT | 432 | cugccgcacgcagcaguucTT | 433 | 62 ± 3 |
| AD-14567 | gcccuguacaaccagcaua | 1888-1906 | gcccuguacaaccagcauaTT | 434 | uaugcugguuguacagggcTT | 435 | 10 ± 0 |
| AD-14568 | cuguacaaccagcauaacc | 1891-1909 | cuguacaaccagcauaaccTT | 436 | gguuaugcugguuguacagTT | 437 | 19 ± 0 |
| AD-14569 | guacaaccagcauaacccg | 1893-1911 | guacaaccagcauaacccgTT | 438 | cggguuaugcugguuguacTT | 439 | 21 ± 1 |
| AD-14570 | cuauuccuuugcccggcau | 2285-2303 | cuauuccuuugcccggcauTT | 440 | augccgggcaaaggaauagTT | 441 | 65 ± 2 |
| AD-14571 | agcggaggaaggagucgcc | 143-161 | agcggaggaaggagucgccTT | 442 | ggcgacuccuuccuccgcuTT | 443 | 75 ± 2 |
| AD-14572 | ggaggaaggagucgccgag | 146-164 | ggaggaaggagucgccgagTT | 444 | cucggcgacuccuuccuccTT | 445 | 43 ± 2 |
| AD-14573 | acuuugagacuuuuccgu | 279-297 | acuuugagacuuuuccguTT | 446 | acggaaaagucucaaaguTT | 447 | 32 ± 2 |
| AD-14574 | uugagacuuuuccguugcc | 283-301 | uugagacuuuuccguugccTT | 448 | ggcaacggaaaagucucaaTT | 449 | 96 ± 4 |
| AD-14575 | accucuuggcgcgacgcug | 324-342 | accucuuggcgcgacgcugTT | 450 | cagcgucgcgccaagagguTT | 451 | 67 ± 3 |
| AD-14576 | gacccggccucccgcaaag | 473-491 | gacccggccucccgcaaagTT | 452 | cuuugcgggaggccgggucTT | 453 | 54 ± 3 |
| AD-14577 | cccggccucccgcaaagac | 475-493 | cccggccucccgcaaagacTT | 454 | gucuuugcgggaggccgggTT | 455 | 48 ± 4 |
| AD-14578 | cuccuccaggagacggauc | 579-597 | cuccuccaggagacggaucTT | 456 | gauccgucuccuggaggagTT | 457 | 25 ± 1 |
| AD-14579 | caccuucugguaccagauc | 637-655 | caccuucugguaccagaucTT | 458 | gaucugguaccagaaggugTT | 459 | 25 ± 1 |
| AD-14580 | cuucugguaccagaucgcg | 640-658 | cuucugguaccagaucgcgTT | 460 | cgcgaucugguaccagaagTT | 461 | 42 ± 2 |
| AD-14581 | uucugguaccagaucgcgc | 641-659 | uucugguaccagaucgcgcTT | 462 | gcgcgaucugguaccagaaTT | 463 | 56 ± 2 |
| AD-14582 | gguuauuccgugggauac | 667-685 | gguuauuccgugggauacTT | 464 | guaucccacggaaauaaccTT | 465 | 19 ± 2 |
| AD-14583 | accucagcuuucccucgag | 740-758 | accucagcuuucccucgagTT | 466 | cucgagggaaagcugagguTT | 467 | 40 ± 4 |
| AD-14584 | ccucagcuuucccucgagg | 741-759 | ccucagcuuucccucgaggTT | 468 | ccucgagggaaagcugaggTT | 469 | 47 ± 5 |
| AD-14585 | uaccuuuugccgggagacc | 766-784 | uaccuuuugccgggagaccTT | 470 | ggucucccggcaaaagguaTT | 471 | 102 ± 7 |
| AD-14586 | ccaugccgcccuccgggcu | 866-884 | ccaugccgcccuccgggcuTT | 472 | agcccggagggcggcauggTT | 473 | 54 ± 3 |
| AD-14587 | acuauccaccugcaagacu | 954-972 | acuauccaccugcaagacuTT | 474 | agucuugcagguggauagTT | 475 | 22 ± 2 |
| AD-14588 | cuauccaccugcaagacua | 955-973 | cuauccaccugcaagacuaTT | 476 | uagucuugcagguggauagTT | 477 | 14 ± 1 |
| AD-14589 | guccaagcugcggcucgcc | 1029-1047 | guccaagcugcggcucgccTT | 478 | ggcgagccgcagcuuggacTT | 479 | 31 ± 2 |
| AD-14590 | cgagccugaggccgacuac | 1158-1176 | cgagccugaggccgacuacTT | 480 | guagucggccucaggcucgTT | 481 | 16 ± 1 |
| AD-14591 | uggugaaacccacaacga | 1205-1223 | uggugaaacccacaacgaTT | 482 | ucguugugggguuccaccaTT | 483 | 98 ± 4 |
| AD-14592 | acccacaacgaaaucuaug | 1213-1231 | acccacaacgaaaucuaugTT | 484 | cauagauuucguugugggTT | 485 | 14 ± 1 |

TABLE 5-continued

Additional RNAi agents targeting hTGF-beta

| Duplex identifier | 19 mer target sequence | target sequence in NM_000660.3 | Sense strand sequence | SEQ ID NO: | Antisense strand sequence | SEQ ID NO: | Remaining TGF-beta mRNA in % of controls ± stand. dev. |
|---|---|---|---|---|---|---|---|
| AD-14593 | ucaagcagaguacacacag | 1238-1256 | ucaagcagaguacacacagTT | 486 | cuguguguacucugcuugaTT | 487 | 67 ± 8 |
| AD-14594 | cagaguacacacagcauau | 1243-1261 | cagaguacacacagcauauTT | 488 | auaugcugugugutacucugTT | 485 | 9 ± 1 |
| AD-14595 | ucuucaacacaucagagcu | 1268-1286 | ucuucaacacaucagagcuTT | 490 | agcucugaugugutugaagaTT | 491 | 23 ± 3 |
| AD-14596 | gcgguaccugaacccgugu | 1294-1312 | gcgguaccugaacccguguTT | 492 | acacggguucagguaccgcTT | 493 | 33 ± 2 |
| AD-14597 | cugcugaggcucaaguuaa | 1336-1354 | cugcugaggcucaaguuaaTT | 494 | uuaacuugagccucagcagTT | 495 | 8 ± 1 |
| AD-14598 | gcgauaccucagcaaccgg | 1404-1422 | gcgauaccucagcaaccggTT | 496 | ccgguugcugagguaucgcTT | 497 | 15 ± 0 |
| AD-14599 | ggcacccagcgacucgcca | 1428-1446 | ggcacccagcgacucgccaTT | 498 | uggcgagucgcuggggugccTT | 499 | 20 ± 2 |
| AD-14600 | ccagcgacucgccagagug | 1433-1451 | ccagcgacucgccagaguguTT | 500 | cacucuggcgagucgcuggTT | 501 | 17 ± 2 |
| AD-14601 | gagugguuaucuuuugaug | 1447-1465 | gagugguuaucuuuugaugTT | 502 | caucaaaagauaaccacucTT | 503 | 13 ± 1 |
| AD-14602 | uugugcggcaguugguugag | 1475-1493 | uugugcggcaguugguugagTT | 504 | cucaaccacugccgcacaaTT | 505 | 132 ± 9 |
| AD-14603 | ugugacagcagggauaaca | 1540-1558 | ugugacagcagggauaacaTT | 506 | uguuaucccugcugucacaTT | 507 | 16 ± 3 |
| AD-14604 | acagcagggauaacacacu | 1544-1562 | acagcagggauaacacacuTT | 508 | aguguguuauccugcuguTT | 509 | 19 ± 1 |
| AD-14605 | cagcagggauaacacacug | 1545-1563 | cagcagggauaacacacugTT | 510 | caguguguuauccugcuTT | 511 | 34 ± 2 |
| AD-14606 | uaacacacugcaaguggac | 1554-1572 | uaacacacugcaaguggacTT | 512 | guccacuugcaguguguuaTT | 513 | 76 ± 2 |
| AD-14607 | guucacuaccggccgccga | 1581-1599 | guucacuaccggccgccgaTT | 514 | ucggcggccgguagugaacTT | 515 | 23 ± 1 |
| AD-14608 | uggccaccauucauggcau | 1607-1625 | uggccaccauucauggcauTT | 516 | augccaugaaugguggccaTT | 517 | 19 ± 1 |
| AD-14609 | cauucauggcaugaaccgg | 1614-1632 | cauucauggcaugaaccggTT | 518 | ccgguucaugccaugaauTT | 519 | 24 ± 2 |
| AD-14610 | cagcaucugcaaagcuccc | 1672-1690 | cagcaucugcaaagcucccTT | 520 | gggagcuuugcagaugcugTT | 521 | 17 ± 2 |
| AD-14611 | gcaaagcucccggcaccgc | 1680-1698 | gcaaagcucccggcaccgcTT | 522 | gcggugccgggagcuuugcTT | 523 | 73 ± 5 |
| AD-14612 | ggagaagaacugcugcgug | 1734-1752 | ggagaagaacugcugcgugTT | 524 | cacgcagcaguucuucuccTT | 525 | 13 ± 0 |
| AD-14613 | gaagaacugcugcgugcgg | 1737-1755 | gaagaacugcugcgugcggTT | 526 | ccgcacgcagcaguucuucTT | 527 | 62 ± 4 |
| AD-14614 | gcuggaaguggauccacga | 1787-1805 | gcuggaaguggauccacgaTT | 528 | ucgugauccacuuccagcTT | 529 | 12 ± 1 |
| AD-14615 | uuuggagccuggacacgca | 1853-1871 | uuuggagccuggacacgcaTT | 530 | ugcguguccaggcuccaaaTT | 531 | 35 ± 1 |
| AD-14616 | uuggagccuggacacgcag | 1854-1872 | uuggagccuggacacgcagTT | 532 | cugcguguccaggcuccaaTT | 533 | 76 ± 7 |
| AD-14617 | gccgugcugcgugccgcag | 1926-1944 | gccgugcugcgugccgcagTT | 534 | cugcggcacgcagcacggcTT | 535 | 71 ± 5 |
| AD-14618 | uguccaacaugaucgugcg | 2003-2021 | uguccaacaugaucgugcgTT | 536 | cgcacgaucauguuggacaTT | 537 | 41 ± 2 |
| AD-14619 | cugcggaucucuguGucau | 2179-2197 | cugcggaucucuguGucauTT | 538 | augacacagagauccgcagTT | 539 | 76 ± 7 |
| AD-14620 | gcacuauuccuuugcccgg | 2282-2300 | gcacuauuccuuugcccggTT | 540 | ccgggcaaaggaauagugcTT | 541 | 89 ± 9 |
| AD-14621 | ccggccucccgcaaagacu | 476-494 | ccggccucccgcaaagacuTT | 542 | agucuuugcgggaggccggTT | 543 | 48 ± 3 |
| AD-14622 | cuacuggugcugacgccug | 919-937 | cuacuggugcugacgccugTT | 544 | caggcgucagcaccaguagTT | 545 | 14 ± 1 |
| AD-14623 | auucauggcaugaaccggc | 1615-1633 | auucauggcaugaaccggcTT | 546 | gccgguucaugccaugaauTT | 547 | 103 ± 6 |
| AD-14624 | aacugcugcgugcggcagc | 1741-1759 | aacugcugcgugcggcagcTT | 548 | gcugccgcacgcagcaguuTT | 549 | 82 ± 3 |
| AD-14625 | cggaggaaggagucgccga | 145-163 | cggaggaaggagucgccgaTT | 550 | ucggcgacuccuuccuccgTT | 551 | 47 ± 3 |
| AD-14626 | ggagcggaggagggacga | 236-254 | ggagcggaggagggacgaTT | 552 | ucgucccuccuccgcuccTT | 553 | 31 ± 1 |
| AD-14627 | gcccucgggagucgccgac | 457-475 | gcccucgggagucgccgacTT | 554 | gucggcgacucccgagggcTT | 555 | 56 ± 6 |

TABLE 5-continued

Additional RNAi agents targeting hTGF-beta

| Duplex identifier | 19 mer target sequence | target sequence in NM_000660.3 | Sense strand sequence | SEQ ID NO: | Antisense strand sequence | SEQ ID NO: | Remaining TGF-beta mRNA in % of controls ± stand. dev. |
|---|---|---|---|---|---|---|---|
| AD-14628 | uuucuccuccaggagacgg | 576-594 | uuucuccuccaggagacggTT | 556 | ccgucuccuggaggagaaaTT | 557 | 90 ± 3 |
| AD-14629 | ucgaggcccuccuaccuuu | 754-772 | ucgaggcccuccuaccuuuTT | 558 | aaagguaggagggccucgaTT | 559 | 25 ± 2 |
| AD-14630 | uacuggugcugacgccugg | 920-938 | uacuggugcugacgccuggTT | 560 | ccaggcgucagcaccaguaTT | 561 | 34 ± 2 |
| AD-14631 | gacuauccaccugcaagac | 953-971 | gacuauccaccugcaagacTT | 562 | gucuugcagguggauagucTT | 563 | 24 ± 3 |
| AD-14632 | uacaacagcacccgcgacc | 1108-1126 | uacaacagcacccgcgaccTT | 564 | ggucgcggugucguuguaTT | 565 | 113 ± 4 |
| AD-14633 | ugcugaggcucaaguuaaa | 1337-1355 | ugcugaggcucaaguuaaaTT | 566 | uuuaacuugagccucagcaTT | 567 | 8 ± 1 |
| AD-14634 | ccugugacagcagggauaa | 1538-1556 | ccugugacagcagggauaaTT | 568 | uuaucccgcugucucacaggTT | 569 | 14 ± 1 |
| AD-14635 | auaacacacugcaagugga | 1553-1571 | auaacacacugcaaguggaTT | 570 | uccacuugcaguguguuauTT | 571 | 18 ± 1 |
| AD-14636 | uauugcuucagcuccacgg | 1717-1735 | uauugcuucagcuccacggTT | 572 | ccguggagcugaagcaauaTT | 573 | 109 ± 5 |
| AD-14637 | gcuguccaacaugaucgug | 2001-2019 | gcuguccaacaugaucgugTT | 574 | cacgaucauguuggacagcTT | 575 | 29 ± 1 |
| AD-14638 | gucuccaucccugacguuc | 2214-2232 | gucuccaucccugacguucTT | 576 | gaacgucagggauggagacTT | 577 | 75 ± 11 |

[1] a, g, c, u: ribonucleotide 5'-monophosphates (except where in 5'-most position, see below); T: deoxythymidine 5'-monophosphate; all sequences given 5' → 3'; due to synthesis procedures, the 5'-most nucleic acid is a nucleoside, i.e. does not bear a 5'-monophosphate group

---

What is claimed is:

1. An isolated iRNA agent, comprising an antisense strand and a sense strand complementary to said antisense strand, wherein the antisense strand comprises SEQ ID NO:88 (cmaaugumacmagcugccgcmacTT*), wherein cm is 2'-O-methylcytidine-5'-monophosphate, wherein um is 2'-O-methyl-uridine-5'-monophosphate, and wherein T* is deoxythymidine 5'-monothiophosphate.

2. The iRNA agent of claim 1, wherein said iRNA agent mediates the cleavage of a TGF-beta mRNA within the target sequence iRNA agent AL-DP-6858.

3. The iRNA agent of claim 1, wherein the iRNA agent further comprises a non-nucleotide moiety.

4. The iRNA of claim 1, wherein the sense and/or antisense strand is further stabilized against nucleolytic degradation.

5. The iRNA agent of claim 1, wherein the sense strand further comprises at least one 3'-overhang wherein said 3'-overhang comprises from 1 to 6 nucleotides.

6. The iRNA agent of claim 1, further comprising a phosphorothioate at the first internucleotide linkage at the 5' end of the sense strand.

7. The iRNA agent of claim 6, further comprising a phosphorothioate at the first internucleotide linkage at the 3' end of the sense strand.

8. The iRNA agent of claim 1, further comprising a 2'-modified nucleotide in the sense strand.

9. The iRNA agent of claim 8, wherein the 2'-modified nucleotide comprises a modification selected from the group consisting of: 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), and 2'-O—N-methylacetamido (2'-O—NMA).

10. The iRNA agent of claim 1, wherein said sense strand is 21 contiguous nucleotides of the sense sequence of iRNA agent AL-DP-6858 (SEQ ID NO:85).

11. The iRNA agent of claim 1, wherein said sense strand comprises SEQ ID NO:85.

12. The iRNA agent of claim 1, wherein said sense strand consists of SEQ ID NO:85.

13. The iRNA agent of claim 1, wherein the iRNA agent is AL-DP-6271.

14. The iRNA agent of claim 1, wherein the antisense consists of SEQ ID NO:88 (cmaaugumacmagcugccgcmacTT*), wherein cm is 2'-O-methylcytidine-5'-monophosphate, wherein um is 2'-O-methyl-uridine-5'-monophosphate, and wherein T* is deoxythymidine 5'-monothiophosphate.

15. The iRNA agent of claim 1, wherein the iRNA agent comprises AL-DP-6271.

16. An isolated iRNA agent, comprising an antisense strand and a sense strand complementary to said antisense strand, wherein the sense strand comprises SEQ ID NO:87 (gumgcmggcmagcmumgumacmaumumgTT*), wherein cm is 2'-O-methylcytidine-5'-monophosphate, wherein um is 2'-O-methyl-uridine-5'-monophosphate, and wherein T* is deoxythymidine 5'-monothiophosphate.

17. The iRNA agent of claim 16, wherein the sense strand consists of SEQ ID NO:87 (gumgcmggcmagcmumgumacmaumumgTT*), wherein cm is 2'-O-methylcytidine-5'-monophosphate, wherein um is 2'-O-methyl-uridine-5'-monophosphate, and wherein T* is deoxythymidine 5'-monothiophosphate.

18. An isolated iRNA agent, comprising an antisense strand and a sense strand complementary to said antisense strand, wherein the sense strand comprises SEQ ID NO:87 (gumgcmggcmagcmumgumacmaumumgTT*) and the antisense strand comprises SEQ ID NO:88 (cmaaugumacmagcugccgcmacTT*), wherein cm is 2'-O-methylcytidine-5'-monophosphate, wherein um is 2'-O-methyl-uridine-5'-monophosphate, and wherein T* is deoxythymidine 5'-monothiophosphate.

19. The iRNA agent of claim 18, wherein the sense strand consists of SEQ ID NO:87 (gumgcmggcmagcmumgumacmaumumgTT*) and the antisense strand consists of SEQ ID NO:88 (cmaaugumacmagcugccgcmacTT*), wherein cm is 2'-O-methylcytidine-5'-monophosphate, wherein um is 2'-O-methyl-uridine-5'-monophosphate, and wherein T* is deoxythymidine 5'-monothiophosphate.

20. A vector encoding the iRNA agent of claim 1.

21. A cell comprising the iRNA agent of claim 1 or the vector of claim 20.

22. A method of making the iRNA agent of claim 1, the method comprising the synthesis of the iRNA agent, wherein the sense and antisense strands comprise at least one modification that stabilizes the iRNA agent against nucleolytic degradation.

23. A pharmaceutical composition comprising the iRNA agent of claim 1 and a pharmaceutically acceptable carrier.

24. A method of treating a human diagnosed as having a disease or disorder associated with undesired TGF-beta signaling, comprising administering to a subject in need of such treatment a therapeutically effective amount of the iRNA agent of claim 1.

25. The method of claim 24, wherein the human is diagnosed as having idiopathic pulmonary fibrosis, diabetic nephropathy or chronic liver disease.

26. A method of reducing the levels of a TGF-beta mRNA in a cell of a subject, or of TGF-beta protein secreted by a cell of a subject, comprising the step of administering the iRNA agent of claim 1 to said subject.

27. The method of claim 26 wherein said iRNA agent mediates the cleavage of a TGF-beta mRNA within the target sequence of iRNA agent AL-DP-6858.

28. The method of claim 26, wherein said iRNA agent is administered to the subject.

29. The method of claim 28, wherein said administration comprises pulmonary administration.

30. The method of claim 26, wherein the level of TGF-beta protein and/or TGF-beta mRNA is reduced by at least 20%.

31. The method of claim 26, wherein said sense strand is 21 contiguous nucleotides of the sense sequence of iRNA agent AL-DP-6858 (SEQ ID NO:85).

32. A method of reducing the levels of a TGF-beta mRNA in a cell, or of TGF-beta protein secreted by a cell, comprising contacting the cell with the iRNA agent of claim 1.

* * * * *